United States Patent [19]

Huff et al.

[11] Patent Number: 5,760,054

[45] Date of Patent: Jun. 2, 1998

[54] ALPHA IC ADRENERGIC RECEPTOR ANTAGONISTS

[75] Inventors: Joel R. Huff, Gwynedd Valley, Pa.; Hee-Yoon Lee, Yusung-Gu, Rep. of Korea; Jennie B. Nerenberg, Maple Glen, Pa.; Wayne J. Thompson, Lansdale, Pa.; Ian M. Bell, Harleysville, Pa.

[73] Assignee: Merck & Co., Inc., Rahway, N.J.

[21] Appl. No.: 722,001

[22] PCT Filed: Apr. 13, 1995

[86] PCT No.: PCT/US95/04590

§ 371 Date: Oct. 1, 1996

§ 102(e) Date: Oct. 1, 1996

[87] PCT Pub. No.: WO95/28397

PCT Pub. Date: Oct. 26, 1995

Related U.S. Application Data

[63] Continuation-in-part of Ser. No. 229,276, Apr. 13, 1994, abandoned.

[51] Int. Cl.$^6$ .................. A61K 31/445; C07D 401/04; C07D 471/04; C07D 471/10

[52] U.S. Cl. .................. 514/302; 514/321; 514/322; 514/324; 546/114; 546/198; 546/199; 546/202

[58] Field of Search .................. 514/322, 324, 514/321, 302; 546/114, 198, 199, 202, 115

[56] References Cited

FOREIGN PATENT DOCUMENTS

| | | |
|---|---|---|
| 2621588 A | 10/1987 | France . |
| WO 93/19758 | 10/1993 | WIPO . |
| WO 94/10989 | 5/1994 | WIPO . |

*Primary Examiner*—Alan L. Rotman
*Attorney, Agent, or Firm*—Melvin Winokur

[57] ABSTRACT

This invention relates to certain novel compounds and derivatives thereof, their synthesis, and their use as selective alpha-1C adrenergic receptor antagonists. One application of these compounds is in the treatment of benign prostatic hypertrophy. These compounds are selective in their ability to relax smooth muscle tissue enriched in the alpha1C receptor subtype without at the same time inducing orthostatic hypotension. One such tissue is found surrounding the urethral lining. Therefore, one utility of the instant compounds is to provide acute relief to males suffering from benign prostatic hyperplasia, by permitting less hindered urine flow. Another utility of the instant compounds is provided by combination with a human 5-alpha reductase inhibitory compound, such that both acute and chronic relief from the effects of benign prostatic hyperplasia are achieved.

13 Claims, No Drawings

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

TTTTCTAGAT TRTTNARRTA NCCNAGCC ( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:2:

```
TTTACTAGTA TCSTNGTNAT GTAYTG                                        26
```

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

```
TTTTCTAGAG AARAANGGNA RCCARC                                        26
```

( 2 ) INFORMATION FOR SEQ ID NO:4:

( i ) SEQUENCE CHARACTERISTICS:
        ( A ) LENGTH: 235 base pairs
        ( B ) TYPE: nucleic acid
        ( C ) STRANDEDNESS: both
        ( D ) TOPOLOGY: both ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:4:

```
GCCGCGTCTA CGTGGTGGCC AAGAGGGAGA GCCGGGGCCT CAAGTCTGGC CTCAAGACCG    60
ACAAGTCGGA CTCGGAGCAA GTGACGCTCC GCATCCATCG GAAAAACGCC CCGGCAGGAG   120
GCAGCGGGAT GGCCAGCGCC AAGACCAAGA CGCACTTCTC AGTGAGGCTC CTCAAGTTCT   180
CCCGGGAGAA GAAAGCGGCC AAAACGCTGG GCATCGTGGT CGGCTGCTTC GTCCT        235
```

( 2 ) INFORMATION FOR SEQ ID NO:5:

( i ) SEQUENCE CHARACTERISTICS:
        ( A ) LENGTH: 78 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:5:

```
Arg  Val  Tyr  Val  Val  Ala  Lys  Arg  Glu  Ser  Arg  Gly  Leu  Lys  Ser  Gly
 1              5                        10                       15

Leu  Lys  Thr  Asp  Lys  Ser  Asp  Ser  Glu  Gln  Val  Thr  Leu  Arg  Ile  His
               20                        25                       30

Arg  Lys  Asn  Ala  Pro  Ala  Gly  Gly  Ser  Gly  Met  Ala  Ser  Ala  Lys  Thr
               35                        40                       45

Lys  Thr  His  Phe  Ser  Val  Arg  Leu  Leu  Lys  Phe  Ser  Arg  Glu  Lys  Lys
     50                        55                       60

Ala  Ala  Lys  Thr  Leu  Gly  Ile  Val  Val  Gly  Cys  Phe  Val  Leu
65                   70                       75
```

( 2 ) INFORMATION FOR SEQ ID NO:6:

( i ) SEQUENCE CHARACTERISTICS:
        ( A ) LENGTH: 93 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:6:

```
Leu  Val  Met  Tyr  Cys  Arg  Val  Tyr  Val  Val  Ala  Lys  Arg  Glu  Ser  Arg
 1              5                        10                       15

Gly  Leu  Lys  Ser  Gly  Leu  Lys  Thr  Asp  Lys  Ser  Asp  Ser  Glu  Gln  Val
               20                        25                       30

Thr  Leu  Arg  Ile  His  Arg  Lys  Asn  Ala  Gln  Val  Gly  Gly  Ser  Gly  Val
               35                        40                       45

Thr  Ser  Ala  Lys  Asn  Lys  Thr  His  Phe  Ser  Val  Arg  Leu  Leu  Lys  Phe
     50                        55                       60

Ser  Arg  Glu  Lys  Lys  Ala  Ala  Lys  Thr  Leu  Gly  Ile  Val  Val  Gly  Cys
65                   70                       75                            80

Phe  Val  Leu  Cys  Trp  Leu  Pro  Phe  Phe  Leu  Val  Met  Pro
               85                        90
```

( 2 ) INFORMATION FOR SEQ ID NO:7:

( i ) SEQUENCE CHARACTERISTICS:
        ( A ) LENGTH: 1601 base pairs
        ( B ) TYPE: nucleic acid
        ( C ) STRANDEDNESS: both
        ( D ) TOPOLOGY: both ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

```
GAATTCCCTC  CTAGAAGCTG  AGAGAGCAG   GAGCCTTCGG  TGGGGCAGCT  CAAAATGTAG    60

GTAACTGCGG  GCCAGGAGCA  GCGCCCAGAT  GCCATCGGTC  CCTGCCTTTG  AGCGTCGACG   120

GCTGATCTTT  TGGTTTGAGG  GAGAGACTGG  CGCTGGAGTT  TTGAATTCCG  AATCATGTGC   180

AGAATCGTGA  ATCTTCCCCC  AGCCAGGACG  AATAAGACAG  CGCGGAAAAG  CAGATTCTCG   240
```

-continued

| | | | | | |
|---|---|---|---|---|---|
|TAATTCTGGA|ATTGCATGTT|GCAAGGAGTC|TCCTGGATCT|TCGCACCCAG|CTTCGGGTAC|300|
|GGGAGGGAGT|CCGGGTCCCG|GCTAGGCCAG|CCCGCAGGTG|GAGAGGGTCC|CCGGCAGCCC|360|
|CGCGCGCCCC|TGGCCATGTC|TTTAATGCCC|TGCCCCTTCA|TGTGGCCTTC|TGAGGGTTCC|420|
|CAGGGCTGGC|CAGGGTTGTC|TCCCACCCGC|GCGCGCCGTC|TCACCCCCAG|CCAAACCCAC|480|
|CTGGCAGGGC|TCCCTCCAGA|AGAGACCTTT|TGATTCCCGG|CTCCCGCGCT|CCCGCCTCCG|540|
|CGCCAGCCCG|GGAGGTGGCC|CTGGACAGCC|GGACCTCGCC|CGGCCCCGGC|TGGGACCATG|600|
|GTGTTTCTCT|CGGGAAATGC|TTCCGACAGC|TCCAACTGCA|CCCAACCGCC|GGCACCGGTG|660|
|AACATTTCCA|AGGCCATTCT|GCTCGGGGTG|ATCTTGGGGG|GCCTCATTCT|TTTCGGGGTG|720|
|CTGGGTAACA|TCCTAGTGAT|CCTCTCCGTA|GCCTGTCACC|GACACCTGCA|CTCAGTCACG|780|
|CACTACTACA|TCGTCAACCT|GGCGGTGGCC|GACCTCCTGC|TCACCTCCAC|GGTGCTGCCC|840|
|TTCTCCGCCA|TCTTCGAGGT|CCTAGGCTAC|TGGGCCTTCG|GCAGGGTCTT|CTGCAACATC|900|
|TGGGCGGCAG|TGGATGTGCT|GTGCTGCACC|GCGTCCATCA|TGGGCCTCTG|CATCATCTCC|960|
|ATCGACCGCT|ACATCGGCGT|GAGCTACCCG|CTGCGCTACC|CAACCATCGT|CACCCAGAGG|1020|
|AGGGGTCTCA|TGGCTCTGCT|CTGCGTCTGG|GCACTCTCCC|TGGTCATATC|CATTGGACCC|1080|
|CTCTTCGGCT|GGAGGCAGCC|GGCCCCGAGA|GACGAGACCA|TCTGCCAGAT|CAACGAGGAG|1140|
|CCGGGCTACG|TGCTCTTCTC|GGCTCTGGGC|TCCTTCTACC|TGCCTCTGGC|CATCATCCTG|1200|
|GTCATGTACT|GCCGCGTCTA|CGTGGTGGCC|AAGAGGGAGA|GCCGGGCCT|CAAGTCTGGC|1260|
|CTCAAGACCG|ACAAGTCGGA|CTCGGAGCAA|GTGACGCTCC|GCATCCATCG|GAAAAACGCC|1320|
|CCGGCAGGAG|GCAGCGGGAT|GGCCAGCGCC|AAGACCAAGA|CGCACTTCTC|AGTGAGGCTC|1380|
|CTCAAGTTCT|CCCGGGAGAA|GAAAGCGGCC|AAAACGCTGG|GCATCGTGGT|CGGCTGCTTC|1440|
|GTCCTCTGCT|GGCTGCCTTT|TTTCTTAGTC|ATGCCCATTG|GGTCTTTCTT|CCCTGATTTC|1500|
|AAGCCCTCTG|AAACAGTTTT|TAAAATAGTA|TTTTGGCTCG|GATATCTAAA|CAGCTGCATC|1560|
|AACCCCATCA|TATACCCATG|CTCCAGCCAA|GAGGGAATTC|C||1601|

( 2 ) INFORMATION FOR SEQ ID NO:8:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

TTTGAATTCT GATTTCAAGC CCTCTG                                        26

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO (x i) SEQUENCE DESCRIPTION: SEQ ID NO:9:

TTTGAATTCT TANACYTCYT CNCCRTTYTC    30

(2) INFORMATION FOR SEQ ID NO:10:

(i) SEQUENCE CHARACTERISTICS:
      (A) LENGTH: 512 base pairs
      (B) TYPE: nucleic acid
      (C) STRANDEDNESS: both
      (D) TOPOLOGY: both (i i) MOLECULE TYPE: cDNA (i i i) HYPOTHETICAL: NO (i v) ANTI-SENSE: NO (x i) SEQUENCE DESCRIPTION: SEQ ID NO:10:

| | | | | | |
|---|---|---|---|---|---|
| CTGATTTCAA | GCCCTCTGAA | ACAGTTTTTA | AAATAGTATT | TTGGCTCGGA | TATCTAAACA | 60 |
| GCTGCATCAA | CCCCATCATA | TACCCATGCT | CCAGCCAAGA | GTTCAAAAAG | GCCTTTCAGA | 120 |
| ATGTCTTGAG | AATCCAGTGT | CTCCGCAGAA | AGCAGTCTTC | CAAACATGCC | CTGGGCTACA | 180 |
| CCCTGCACCC | GCCCAGCCAG | GCCGTGGAAG | GGCAACACAA | GGACATGGTG | CGCATCCCCG | 240 |
| TGGGATCAAG | AGAGACCTTC | TACAGGATCT | CCAAGACGGA | TGGCGTTTGT | GAATGGAAAT | 300 |
| TTTTCTCTTC | CATGCCCGT | GGATCTGCCA | GGATTACAGT | GTCCAAAGAC | CAATCCTCCT | 360 |
| GTACCACAGC | CCGGGTGAGA | AGTAAAAGCT | TTTTGCAGGT | CTGCTGCTGT | GTAGGGCCCT | 420 |
| CAACCCCCAG | CCTTGACAAG | AACCATCAAG | TTCCAACCAT | TAAGGTCCAC | ACCATCTCCC | 480 |
| TCAGTGAGAA | CGGCGAAGAG | GTTAAGAATT | TC | | | 512 |

(2) INFORMATION FOR SEQ ID NO:11:

(i) SEQUENCE CHARACTERISTICS:
      (A) LENGTH: 2004 base pairs
      (B) TYPE: nucleic acid
      (C) STRANDEDNESS: both
      (D) TOPOLOGY: both (i i) MOLECULE TYPE: cDNA (i i i) HYPOTHETICAL: NO (i v) ANTI-SENSE: NO (x i) SEQUENCE DESCRIPTION: SEQ ID NO:11:

| | | | | | |
|---|---|---|---|---|---|
| GAATTCCCTC | CTAGAAGCTG | GAGAGAGCAG | GAGCCTTCGG | TGGGGCAGCT | CAAAATGTAG | 60 |
| GTAACTGCGG | GCCAGGAGCA | GCGCCCAGAT | GCCATCGGTC | CCTGCCTTTG | AGCGTCGACG | 120 |
| GCTGATCTTT | TGGTTTGAGG | GAGAGACTGG | CGCTGGAGTT | TTGAATTCCG | AATCATGTGC | 180 |
| AGAATCGTGA | ATCTTCCCCC | AGCCAGGACG | AATAAGACAG | CGCGGAAAAG | CAGATTCTCG | 240 |
| TAATTCTGGA | ATTGCATGTT | GCAAGGAGTC | TCCTGGATCT | TCGCACCCAG | CTTCGGGTAC | 300 |
| GGGAGGGAGT | CCGGGTCCCG | GCTAGGCCAG | CCCGCAGGTG | GAGAGGGTCC | CCGGCAGCCC | 360 |
| CGCGCGCCCC | TGGCCATGTC | TTTAATGCCC | TGCCCCTTCA | TGTGGCCTTC | TGAGGGTTCC | 420 |
| CAGGGCTGGC | CAGGGTTGTC | TCCCACCCGC | GCGCGCCGTC | TCACCCCCAG | CCAAACCCAC | 480 |
| CTGGCAGGGC | TCCCTCCAGA | AGAGACCTTT | TGATTCCCGG | CTCCCGCGCT | CCCGCCTCCG | 540 |
| CGCCAGCCCG | GGAGGTGGCC | CTGGACAGCC | GGACCTCGCC | CGGCCCCGGC | TGGGACCATG | 600 |
| GTGTTTCTCT | CGGGAAATGC | TTCCGACAGC | TCCAACTGCA | CCCAACCGCC | GGCACCGGTG | 660 |
| AACATTTCCA | AGGCCATTCT | GCTCGGGGTG | ATCTTGGGGG | GCCTCATTCT | TTTCGGGGTG | 720 |

-continued

| | | | | | |
|---|---|---|---|---|---|
| CTGGGTAACA | TCCTAGTGAT | CCTCTCCGTA | GCCTGTCACC | GACACCTGCA | CTCAGTCACG | 780 |
| CACTACTACA | TCGTCAACCT | GGCGGTGGCC | GACCTCCTGC | TCACCTCCAC | GGTGCTGCCC | 840 |
| TTCTCCGCCA | TCTTCGAGGT | CCTAGGCTAC | TGGGCCTTCG | GCAGGGTCTT | CTGCAACATC | 900 |
| TGGGCGGCAG | TGGATGTGCT | GTGCTGCACC | GCGTCCATCA | TGGGCCTCTG | CATCATCTCC | 960 |
| ATCGACCGCT | ACATCGGCGT | GAGCTACCCG | CTGCGCTACC | CAACCATCGT | CACCCAGAGG | 1020 |
| AGGGGTCTCA | TGGCTCTGCT | CTGCGTCTGG | GCACTCTCCC | TGGTCATATC | CATTGGACCC | 1080 |
| CTCTTCGGCT | GGAGGCAGCC | GGCCCCGAG | GACGAGACCA | TCTGCCAGAT | CAACGAGGAG | 1140 |
| CCGGGCTACG | TGCTCTTCTC | GGCTCTGGGC | TCCTTCTACC | TGCCTCTGGC | CATCATCCTG | 1200 |
| GTCATGTACT | GCCGCGTCTA | CGTGGTGGCC | AAGAGGGAGA | GCCGGGCCT | CAAGTCTGGC | 1260 |
| CTCAAGACCG | ACAAGTCGGA | CTCGGAGCAA | GTGACGCTCC | GCATCCATCG | GAAAAACGCC | 1320 |
| CCGGCAGGAG | GCAGCGGGAT | GGCCAGCGCC | AAGACCAAGA | CGCACTTCTC | AGTGAGGCTC | 1380 |
| CTCAAGTTCT | CCCGGGAGAA | GAAAGCGGCC | AAAACGCTGG | CATCGTGGT | CGGCTGCTTC | 1440 |
| GTCCTCTGCT | GGCTGCCTTT | TTTCTTAGTC | ATGCCCATTG | GGTCTTTCTT | CCCTGATTTC | 1500 |
| AAGCCCTCTG | AAACAGTTTT | TAAAATAGTA | TTTTGGCTCG | GATATCTAAA | CAGCTGCATC | 1560 |
| AACCCCATCA | TATACCCATG | CTCCAGCCAA | GAGTTCAAAA | AGGCCTTTCA | GAATGTCTTG | 1620 |
| AGAATCCAGT | GTCTCCGCAG | AAAGCAGTCT | TCCAAACATG | CCCTGGGCTA | CACCCTGCAC | 1680 |
| CCGCCCAGCC | AGGCCGTGGA | AGGGCAACAC | AAGGACATGG | TGCGCATCCC | CGTGGGATCA | 1740 |
| AGAGAGACCT | TCTACAGGAT | CTCCAAGACG | GATGGCGTTT | GTGAATGGAA | ATTTTTCTCT | 1800 |
| TCCATGCCCC | GTGGATCTGC | CAGGATTACA | GTGTCCAAAG | ACCAATCCTC | CTGTACCACA | 1860 |
| GCCCGGGTGA | GAAGTAAAAG | CTTTTTGCAG | GTCTGCTGCT | GTGTAGGGCC | CTCAACCCCC | 1920 |
| AGCCTTGACA | AGAACCATCA | AGTTCCAACC | ATTAAGGTCC | ACACCATCTC | CCTCAGTGAG | 1980 |
| AACGGCGAAG | AGGTTTAAGA | ATTC | | | | 2004 |

( 2 ) INFORMATION FOR SEQ ID NO:12:

( i ) SEQUENCE CHARACTERISTICS:
        ( A ) LENGTH: 466 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:12:

```
Met Val Phe Leu Ser Gly Asn Ala Ser Asp Ser Ser Asn Cys Thr Gln
 1               5                  10                  15

Pro Pro Ala Pro Val Asn Ile Ser Lys Ala Ile Leu Leu Gly Val Ile
                20                  25                  30

Leu Gly Gly Leu Ile Leu Phe Gly Val Leu Gly Asn Ile Leu Val Ile
            35                  40                  45

Leu Ser Val Ala Cys His Arg His Leu His Ser Val Thr His Tyr Tyr
        50                  55                  60

Ile Val Asn Leu Ala Val Ala Asp Leu Leu Leu Thr Ser Thr Val Leu
65                  70                  75                  80

Pro Phe Ser Ala Ile Phe Glu Val Leu Gly Tyr Trp Ala Phe Gly Arg
                85                  90                  95
```

```
Val Phe Cys Asn Ile Trp Ala Ala Val Asp Val Leu Cys Cys Thr Ala
                100                 105                 110
Ser Ile Met Gly Leu Cys Ile Ile Ser Ile Asp Arg Tyr Ile Gly Val
        115                 120                 125
Ser Tyr Pro Leu Arg Tyr Pro Thr Ile Val Thr Gln Arg Arg Gly Leu
    130                 135                 140
Met Ala Leu Leu Cys Val Trp Ala Leu Ser Leu Val Ile Ser Ile Gly
145                 150                 155                 160
Pro Leu Phe Gly Trp Arg Gln Pro Ala Pro Glu Asp Glu Thr Ile Cys
                165                 170                 175
Gln Ile Asn Glu Glu Pro Gly Tyr Val Leu Phe Ser Ala Leu Gly Ser
            180                 185                 190
Phe Tyr Leu Pro Leu Ala Ile Ile Leu Val Met Tyr Cys Arg Val Tyr
        195                 200                 205
Val Val Ala Lys Arg Glu Ser Arg Gly Leu Lys Ser Gly Leu Lys Thr
    210                 215                 220
Asp Lys Ser Asp Ser Glu Gln Val Thr Leu Arg Ile His Arg Lys Asn
225                 230                 235                 240
Ala Pro Ala Gly Gly Ser Gly Met Ala Ser Ala Lys Thr Lys Thr His
                245                 250                 255
Phe Ser Val Arg Leu Leu Lys Phe Ser Arg Glu Lys Lys Ala Ala Lys
            260                 265                 270
Thr Leu Gly Ile Val Val Gly Cys Phe Val Leu Cys Trp Leu Pro Phe
        275                 280                 285
Phe Leu Val Met Pro Ile Gly Ser Phe Phe Pro Asp Phe Lys Pro Ser
    290                 295                 300
Glu Thr Val Phe Lys Ile Val Phe Trp Leu Gly Tyr Leu Asn Ser Cys
305                 310                 315                 320
Ile Asn Pro Ile Ile Tyr Pro Cys Ser Ser Gln Glu Phe Lys Lys Ala
                325                 330                 335
Phe Gln Asn Val Leu Arg Ile Gln Cys Leu Arg Arg Lys Gln Ser Ser
            340                 345                 350
Lys His Ala Leu Gly Tyr Thr Leu His Pro Pro Ser Gln Ala Val Glu
        355                 360                 365
Gly Gln His Lys Asp Met Val Arg Ile Pro Val Gly Ser Arg Glu Thr
    370                 375                 380
Phe Tyr Arg Ile Ser Lys Thr Asp Gly Val Cys Glu Trp Lys Phe Phe
385                 390                 395                 400
Ser Ser Met Pro Arg Gly Ser Ala Arg Ile Thr Val Ser Lys Asp Gln
                405                 410                 415
Ser Ser Cys Thr Thr Ala Arg Val Arg Ser Lys Ser Phe Leu Gln Val
            420                 425                 430
Cys Cys Cys Val Gly Pro Ser Thr Pro Ser Leu Asp Lys Asn His Gln
        435                 440                 445
Val Pro Thr Ile Lys Val His Thr Ile Ser Leu Ser Glu Asn Gly Glu
    450                 455                 460
Glu Val
465
```

( 2 ) INFORMATION FOR SEQ ID NO:13:

( i ) SEQUENCE CHARACTERISTICS:
        ( A ) LENGTH: 1621 base pairs
        ( B ) TYPE: nucleic acid
        ( C ) STRANDEDNESS: double (D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO:13:

| | | | | | | |
|---|---|---|---|---|---|---|
| CCCGTGCAGG | GGCCCTACGG | ACACCACCAG | GGCTACGACC | CAGAGCAGGG | CCAGGATGGC | 60 |
| GGCCGCCTTG | CGCTCGGTCA | TGATGGCTGG | GTACTTGAGT | GAGTGGCGCA | CGCCCACGTA | 120 |
| CCGGTCCACG | GAGATGGTGC | AGAGGCTGAG | GATGGAGGCC | GTGCAGCACA | GCACGTCCAC | 180 |
| GGCGGCCGTC | GGGGACTGG | TGGTGAGCGC | GCAGGGCGTG | GGCGTGGGCG | TCTTCCTGGC | 240 |
| AGCCTTCATC | CTTATGGCCG | TGGCAGGTAA | CCTGCTTGTC | ATCCTCTCAG | TGGCCTGCAA | 300 |
| CCGCCACCTG | CAGACCGTCA | CCAACTATTT | CATCGTGAAC | CTGGCCGTGG | CCGACCTGCT | 360 |
| GCTGAGCGCC | ACCGTACTGC | CCTTCTCGGC | CACCATGGAG | GTTCTGGGCT | TCTGGGCCTT | 420 |
| TGGCCGCGCC | TTCTGCGACG | TATGGGCCGC | CGTGGACGTG | CTGTGCTGCA | CGGCCTCCAT | 480 |
| CCTCAGCCTC | TGCACCATCT | CCGTGGACCG | GTACGTGGGC | GTGCGCCACT | CACTCAAGTA | 540 |
| CCCAGCCATC | ATGACCGAGC | GCAAGGCGGC | CGCCATCCTG | GCCCTGCTCT | GGGTCGTAGC | 600 |
| CCTGGTGGTG | TCCGTAGGGC | CCCTGCTGGG | CTGGAAGGAG | CCCGTGCCCC | CTGACGAGCG | 660 |
| CTTCTGCGGT | ATCACCGAGG | AGGCGGGCTA | CGCTGTCTTC | TCCTCCGTGT | GCTCCTTCTA | 720 |
| CCTGCCCATG | GCGGTCATCG | TGGTCATGTA | CTGCCGCGTG | TACGTGGTCG | CGCGCAGCAC | 780 |
| CACGCGCAGC | CTCGAGGCAG | GCGTCAAGCG | CGAGCGAGGC | AAGGCCTCCG | AGGTGGTGCT | 840 |
| GCGCATCCAC | TGTCGCGGCG | CGGCCACGGG | CGCCGACGGG | GCGCACGGCA | TGCGCAGCGC | 900 |
| CAAGGGCCAC | ACCTTCCGCA | GCTCGCTCTC | CGTGCGCCTG | CTCAAGTTCT | CCCGTGAGAA | 960 |
| GAAAGCGGCC | AAGACTCTGG | CCATCGTCGT | GGGTGTCTTC | GTGCTCTGCT | GGTTCCCTTT | 1020 |
| CTTCTTTGTC | CTGCCGCTCG | GCTCCTTGTT | CCCGCAGCTG | AAGCCATCGG | AGGGCGTCTT | 1080 |
| CAAGGTCATC | TTCTGGCTCG | GCTACTTCAA | CAGCTGCGTG | AACCCGCTCA | TCTACCCCTG | 1140 |
| TTCCAGCCGC | GAGTTCAAGC | GCGCCTTCCT | CCGTCTCCTG | CGCTGCCAGT | GCCGTCGTCG | 1200 |
| CCGGCGCCGC | CGCCCTCTCT | GGCGTGTCTA | CGGCCACCAC | TGGCGGGCCT | CCACCAGCGG | 1260 |
| CCTGCGCCAG | GACTGCGCCC | CGAGTTCGGG | CGACGCGCCC | CCGGAGCGC | CGCTGGCCCT | 1320 |
| CACCGCGCTC | CCCGACCCCG | ACCCCGAACC | CCCAGGCACG | CCCGAGATGC | AGGCTCCGGT | 1380 |
| CGCCAGCCGT | CGAAGCCACC | CAGCGCCTTC | CGCGAGTGGA | GGCTGCTGGG | GCCGTTCCGG | 1440 |
| AGACCCACGA | CCCAGCTGCG | CGCCAAAGTC | GCCAGCCTGT | CGCACAAGAT | CGCCGCCGGG | 1500 |
| GGCGCGCAGC | GCGCAGAGGC | AGCGTGCGCC | CAGCGCTCAG | AGGTGGAGGC | TGTGTCCCTA | 1560 |
| GGCGTCCCAC | ACGAGGTGGC | CGAGGGCGCC | ACCTGCCAGG | CCTACGAATT | GGCCGACTAC | 1620 |
| A | | | | | | 1621 |

(2) INFORMATION FOR SEQ ID NO:14:

(i) SEQUENCE CHARACTERISTICS:
(A) LENGTH: 501 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO ( v ) FRAGMENT TYPE: N-terminal ( x i ) SEQUENCE DESCRIPTION: SEQ ID NO:14:

```
Met Ala Ala Ala Leu Arg Ser Val Met Met Ala Gly Tyr Leu Ser Glu
 1               5                  10                  15
Trp Arg Thr Pro Thr Tyr Arg Ser Thr Glu Met Val Gln Arg Leu Arg
             20                  25                  30
Met Glu Ala Val Gln His Ser Thr Ser Thr Ala Ala Val Gly Gly Leu
         35                  40                  45
Val Val Ser Ala Gln Gly Val Gly Val Gly Val Phe Leu Ala Ala Phe
     50                  55                  60
Ile Leu Met Ala Val Ala Gly Asn Leu Leu Val Ile Leu Ser Val Ala
 65                  70                  75                  80
Cys Asn Arg His Leu Gln Thr Val Thr Asn Tyr Phe Ile Val Asn Leu
                 85                  90                  95
Ala Val Ala Asp Leu Leu Leu Ser Ala Thr Val Leu Pro Phe Ser Ala
                100                 105                 110
Thr Met Glu Val Leu Gly Phe Trp Ala Phe Gly Arg Ala Phe Cys Asp
            115                 120                 125
Val Trp Ala Ala Val Asp Val Leu Cys Cys Thr Ala Ser Ile Leu Ser
        130                 135                 140
Leu Cys Thr Ile Ser Val Asp Arg Tyr Val Gly Val Arg His Ser Leu
145                 150                 155                 160
Lys Tyr Pro Ala Ile Met Thr Glu Arg Lys Ala Ala Ala Ile Leu Ala
                165                 170                 175
Leu Leu Trp Val Val Ala Leu Val Val Ser Val Gly Pro Leu Leu Gly
            180                 185                 190
Trp Lys Glu Pro Val Pro Pro Asp Glu Arg Phe Cys Gly Ile Thr Glu
        195                 200                 205
Glu Ala Gly Tyr Ala Val Phe Ser Ser Val Cys Ser Phe Tyr Leu Pro
    210                 215                 220
Met Ala Val Ile Val Val Met Tyr Cys Arg Val Tyr Val Val Ala Arg
225                 230                 235                 240
Ser Thr Thr Arg Ser Leu Glu Ala Gly Val Lys Arg Glu Arg Gly Lys
                245                 250                 255
Ala Ser Glu Val Val Leu Arg Ile His Cys Arg Gly Ala Ala Thr Gly
            260                 265                 270
Ala Asp Gly Ala His Gly Met Arg Ser Ala Lys Gly His Thr Phe Arg
        275                 280                 285
Ser Ser Leu Ser Val Arg Leu Leu Lys Phe Ser Arg Glu Lys Lys Ala
    290                 295                 300
Ala Lys Thr Leu Ala Ile Val Val Gly Val Phe Val Leu Cys Trp Phe
305                 310                 315                 320
Pro Phe Phe Phe Val Leu Pro Leu Gly Ser Leu Phe Pro Gln Leu Lys
                325                 330                 335
Pro Ser Glu Gly Val Phe Lys Val Ile Phe Trp Leu Gly Tyr Phe Asn
            340                 345                 350
Ser Cys Val Asn Pro Leu Ile Tyr Pro Cys Ser Ser Arg Glu Phe Lys
        355                 360                 365
Arg Ala Phe Leu Arg Leu Leu Arg Cys Gln Cys Arg Arg Arg Arg Arg
    370                 375                 380
Arg Arg Pro Leu Trp Arg Val Tyr Gly His His Trp Arg Ala Ser Thr
385                 390                 395                 400
```

```
Ser  Gly  Leu  Arg  Gln  Asp  Cys  Ala  Pro  Ser  Ser  Gly  Asp  Ala  Pro  Pro
               405                      410                          415

Gly  Ala  Pro  Leu  Ala  Leu  Thr  Ala  Leu  Pro  Asp  Pro  Asp  Pro  Glu  Pro
               420                      425                     430

Pro  Gly  Thr  Pro  Glu  Met  Gln  Ala  Pro  Val  Ala  Ser  Arg  Arg  Ser  His
               435                      440                     445

Pro  Ala  Pro  Ser  Ala  Ser  Gly  Gly  Cys  Trp  Gly  Arg  Ser  Gly  Asp  Pro
          450                      455                     460

Arg  Pro  Ser  Cys  Ala  Pro  Lys  Ser  Pro  Ala  Cys  Arg  Thr  Arg  Ser  Pro
465                           470                     475                          480

Pro  Gly  Ala  Arg  Ser  Ala  Gln  Arg  Gln  Arg  Ala  Pro  Ser  Ala  Gln  Arg
                    485                      490                          495

Trp  Arg  Leu  Cys  Pro
               500
```

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:15:

```
TCTAGACCAT GAAYCCNGAY CTGG                                              24
```

( 2 ) INFORMATION FOR SEQ ID NO:16:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:16:

```
TTTGAATTCA CATWCCGACY ACAATGCCC                                         29
```

( 2 ) INFORMATION FOR SEQ ID NO:17:

( i ) SEQUENCE CHARACTERISTICS:
        ( A ) LENGTH: 921 base pairs
        ( B ) TYPE: nucleic acid
        ( C ) STRANDEDNESS: double
        ( D ) TOPOLOGY: both ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:17:

```
TCTAGACCAT GAATCCCGAC CTGGACACCG GCCACAACAC ATCAGCACCT GCCCACTGGG        60

GAGAGTTGAA AAATGCCAAC TTCACTGGCC CCAACCAGAC CTCGAGCAAC TCCACACTGC       120
```

| | | | | | |
|---|---|---|---|---|---|
| CCCAGCTGGA | CATCACCAGG | GCCATCTCTG | TGGGCCTGGT | GCTGGGCGCC | TTCATCCTCT | 180 |
| TTGCCATCGT | GGGCAACATC | CTAGTCATCT | TGTCTGTGGC | CTGCAACCGG | CACCTGCGGA | 240 |
| CGCCCACCAA | CTACTTCATT | GTCAACCTGG | CCATGGCCGA | CCTGCTGTTG | AGCTTCACCG | 300 |
| TCCTGCCCTT | CTCAGCGGCC | CTAGAGGTGC | TCGGCTACTG | GGTGCTGGGG | CGGATCTTCT | 360 |
| GTGACATCTG | GGCAGCCGTG | GATGTCCTGT | GCTGCACAGC | GTCCATTCTG | AGCCTGTGCG | 420 |
| CCATCTCCAT | CGATCGCTAC | ATCGGGGTGC | GCTACTCTCT | GCAGTATCCC | ACGCTGGTCA | 480 |
| CCCGGAGGAA | GGCCATCTTG | GCCCTGCTCA | GTGTCTGGGT | CTTGTCCACC | GTCATCTCCA | 540 |
| TCGGCCTCT | CCTTGGGTGG | AAGGAGCCGG | CACCCAACGA | TGACAAGGAG | TGCGGGGTCA | 600 |
| CCGAAGAACC | CTTCTATGCC | CTCTTCTCCT | CTCTGGGCTC | CTTCTACATC | CCTCTGGCGG | 660 |
| TCATTCTAGT | CATGTACTGC | CGTGTCTATA | TAGTGGCCAA | GAGAACCACC | AAGAACCTAG | 720 |
| AGGCAGGAGT | CATGAAGGAG | ATGTCCAACT | CCAAGGAGCT | GACCCTGAGG | ATCCATTCCA | 780 |
| AGAACTTTCA | CGAGGACACC | CTTAGCAGTA | CCAAGGCCAA | GGGCCACAAC | CCCAGGAGTT | 840 |
| CCATAGCTGT | CAAACTTTTT | AAGTTCTCCA | GGGAAAAGAA | AGCAGCTAAG | ACGTTGGGCA | 900 |
| TTGTGGTCGG | TATGTGAATT | C | | | | 921 |

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:18:

GAAGGCGCGC TTGAACTC       18

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:19:

AGAGAACCAC CAAGAACC       18

( 2 ) INFORMATION FOR SEQ ID NO:20:

( i ) SEQUENCE CHARACTERISTICS:
        ( A ) LENGTH: 389 base pairs
        ( B ) TYPE: nucleic acid
        ( C ) STRANDEDNESS: both
        ( D ) TOPOLOGY: both ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:20:

| | | | | | |
|---|---|---|---|---|---|
| AAGAGAACCA | CCAAGAACCT | AGAGGCAGGA | GTCATGAAGG | AGATGTCCAA | CTCCAAGGAG | 60
| CTGACCCTGA | GGATCCATTC | CAAGAACTTT | CACGAGGACA | CCCTTAGCAG | TACCAAGGCC | 120
| AAGGGCCACA | ACCCCAGGAG | TTCCATAGCT | GTCAAACTTT | TTAAGTTCTC | CAGGGAAAAG | 180
| AAAGCAGCTA | AGACGTTGGG | CATTGTGGTC | GGTATGTTCA | TCTTGTGCTG | GCTACCCTTC | 240
| TTCATCGCTC | TACCGCTTGG | CTCCTTGTTC | TCCACCCTGA | AGCCCCCGA | CGCCGTGTTC | 300
| AAGGTGGTGT | TCTGGCTGGG | CTACTTCAAC | AGCTGCCTCA | ACCCCATCAT | CTACCCATGC | 360
| TCCAGCAAGG | AGTTCAAGCG | CGCTTTCGT | | | | 389

( 2 ) INFORMATION FOR SEQ ID NO:21:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:21:

| | | |
|---|---|---|
| TTTGAATTCA | TGTTCAAGGT | GGTGTTC | 27

( 2 ) INFORMATION FOR SEQ ID NO:22:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:22:

| | | | |
|---|---|---|---|
| TTTGAATTCT | AAAASTGNCC | NGGNSCCAGN | GGCAT | 35

( 2 ) INFORMATION FOR SEQ ID NO:23:

( i ) SEQUENCE CHARACTERISTICS:
        ( A ) LENGTH: 582 base pairs
        ( B ) TYPE: nucleic acid
        ( C ) STRANDEDNESS: both
        ( D ) TOPOLOGY: both ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:23:

| | | | | | |
|---|---|---|---|---|---|
| GAATTCATGA | TTCAAGGTGG | TGTTCTGGCT | GGGCTACTTC | AACAGCTGCC | TCAATCCCAT | 60
| CATCTACCCG | TGCTCCAGCA | AGGAGTTCAA | GCGCGCCTTC | ATGCGTATCC | TTGGGTGCCA | 120
| GTGCCGCGGT | GGCCGCCGCC | GCCGCCGCCG | TCGCCGTCTA | GGCGCGTGCG | CTTACACCTA | 180
| CCGGCCGTGG | ACCCGCGGCG | GCTCGCTGGA | GAGATCACAG | TCGCGGAAGG | ACTCTCTGGA | 240

| | | | | |
|---|---|---|---|---|
| TGACAGCGGC | AGCTGCATGA | GCGGCCAGAA | GAGGACCCTG | CCCTCGGCGT CGCCCAGCCC 300 |
| GGGCTACCTG | GGTCGAGGAA | CGCAGCCACC | CGTGGAGCTG | TGCGCCTTCC CCGAGTGGAA 360 |
| ACCCGGGGCG | CTGCTCAGCT | TGCCAGAGCC | TCCTGGCCGC | CGCGGCCGTC TCGACTCTGG 420 |
| GCCACTCTTC | ACCTTCAAGC | TCCTGGGCGA | TCCTGAGAGC | CCGGGAACCG AAGCGACAGC 480 |
| CAGCAACGGG | GGCTGCGACA | CCACGACCGA | CCTGGCCAAC | GGGCAGCCCG GCTTCAAGAG 540 |
| CAACATGCCC | CTGGGCCCGG | GCCACTTTTA | AAAGCCGAAT | TC 582 |

( 2 ) INFORMATION FOR SEQ ID NO:24:

( i ) SEQUENCE CHARACTERISTICS:
        ( A ) LENGTH: 1567 base pairs
        ( B ) TYPE: nucleic acid
        ( C ) STRANDEDNESS: both
        ( D ) TOPOLOGY: both ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:24:

| | | | | |
|---|---|---|---|---|
| TCTAGACCAT | GAATCCCGAC | CTGGACACCG | GCCACAACAC | ATCAGCACCT GCCCACTGGG 60 |
| GAGAGTTGAA | AAATGCCAAC | TTCACTGGCC | CCAACCAGAC | CTCGAGCAAC TCCACACTGC 120 |
| CCCAGCTGGA | CATCACCAGG | GCCATCTCTG | TGGGCCTGGT | GCTGGGCGCC TTCATCCTCT 180 |
| TTGCCATCGT | GGGCAACATC | CTAGTCATCT | TGTCTGTGGC | CTGCAACCGG CACCTGCGGA 240 |
| CGCCCACCAA | CTACTTCATT | GTCAACCTGG | CCATGGCCGA | CCTGCTGTTG AGCTTCACCG 300 |
| TCCTGCCCTT | CTCAGCGGCC | CTAGAGGTGC | TCGGCTACTG | GGTGCTGGGG CGGATCTTCT 360 |
| GTGACATCTG | GGCAGCCGTG | GATGTCCTGT | GCTGCACAGC | GTCCATTCTG AGCCTGTGCG 420 |
| CCATCTCCAT | CGATCGCTAC | ATCGGGGTGC | GCTACTCTCT | GCAGTATCCC ACGCTGGTCA 480 |
| CCCGGAGGAA | GGCCATCTTG | GCCCTGCTCA | GTGTCTGGGT | CTTGTCCACC GTCATCTCCA 540 |
| TCGGGCCTCT | CCTTGGGTGG | AAGGAGCCGG | CACCCAACGA | TGACAAGGAG TGCGGGGTCA 600 |
| CCGAAGAACC | CTTCTATGCC | CTCTTCTCCT | CTCTGGGCTC | CTTCTACATC CCTCTGGCGG 660 |
| TCATTCTAGT | CATGTACTGC | CGTGTCTATA | TAGTGGCCAA | GAGAACCACC AAGAACCTAG 720 |
| AGGCAGGAGT | CATGAAGGAG | ATGTCCAACT | CCAAGGAGCT | GACCCTGAGG ATCCATTCCA 780 |
| AGAACTTTCA | CGAGGACACC | CTTAGCAGTA | CCAAGGCCAA | GGGCCACAAC CCCAGGAGTT 840 |
| CCATAGCTGT | CAAACTTTTT | AAGTTCTCCA | GGGAAAAGAA | AGCAGCTAAG ACGTTGGGCA 900 |
| TTGTGGTCGG | TATGTTCATC | TTGTGCTGGC | TACCCTTCTT | CATCGCTCTA CCGCTTGGCT 960 |
| CCTTGTTCTC | CACCCTGAAG | CCCCCCGACG | CCGTGTTCAA | GGTGGTGTTC TGGCTGGGCT 1020 |
| ACTTCAACAG | CTGCCTCAAC | CCCATCATCT | ACCCATGCTC | CAGCAAGGAG TTCAAGCGCG 1080 |
| CCTTCATGCG | TATCCTTGGG | TGCCAGTGCC | GCGGTGGCCG | CCGCCGCCGC CGCCGTCGCC 1140 |
| GTCTAGGCGC | GTGCGCTTAC | ACCTACCGGC | CGTGGACCCG | CGGCGGCTCG CTGGAGAGAT 1200 |
| CACAGTCGCG | GAAGGACTCT | CTGGATGACA | GCGGCAGCTG | CATGAGCGGC CAGAAGAGGA 1260 |
| CCCTGCCCTC | GGCGTCGCCC | AGCCGGGCT | ACCTGGGTCG | AGGAACGCAG CCACCCGTGG 1320 |
| AGCTGTGCGC | CTTCCCCGAG | TGGAAACCCG | GGCGCTGCT | CAGCTTGCCA GAGCCTCCTG 1380 |
| GCCGCCGCGG | CCGTCTCGAC | TCTGGCCAC | TCTTCACCTT | CAAGCTCCTG GGCGATCCTG 1440 |
| AGAGCCCGGG | AACCGAAGCG | ACAGCCAGCA | ACGGGGCTG | CGACACCACG ACCGACCTGG 1500 |
| CCAACGGGCA | GCCCGGCTTC | AAGAGCAACA | TGCCCCTGGG | CCCGGGCCAC TTTTAAAAGC 1560 |

CGAATTC 1567

( 2 ) INFORMATION FOR SEQ ID NO:25:

( i ) SEQUENCE CHARACTERISTICS:
        ( A ) LENGTH: 515 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:25:

```
Met Asn Pro Asp Leu Asp Thr Gly His Asn Thr Ser Ala Pro Ala His
  1               5                  10                  15

Trp Gly Glu Leu Lys Asn Ala Asn Phe Thr Gly Pro Asn Gln Thr Ser
             20                  25                  30

Ser Asn Ser Thr Leu Pro Gln Leu Asp Ile Thr Arg Ala Ile Ser Val
         35                  40                  45

Gly Leu Val Leu Gly Ala Phe Ile Leu Phe Ala Ile Val Gly Asn Ile
     50                  55                  60

Leu Val Ile Leu Ser Val Ala Cys Asn Arg His Leu Arg Thr Pro Thr
 65                  70                  75                  80

Asn Tyr Phe Ile Val Asn Leu Ala Met Ala Asp Leu Leu Leu Ser Phe
                     85                  90                  95

Thr Val Leu Pro Phe Ser Ala Ala Leu Glu Val Leu Gly Tyr Trp Val
             100                 105                 110

Leu Gly Arg Ile Phe Cys Asp Ile Trp Ala Ala Val Asp Val Leu Cys
             115                 120                 125

Cys Thr Ala Ser Ile Leu Ser Leu Cys Ala Ile Ser Ile Asp Arg Tyr
     130                 135                 140

Ile Gly Val Arg Tyr Ser Leu Gln Tyr Pro Thr Leu Val Thr Arg Arg
145                 150                 155                 160

Lys Ala Ile Leu Ala Leu Leu Ser Val Trp Val Leu Ser Thr Val Ile
                 165                 170                 175

Ser Ile Gly Pro Leu Leu Gly Trp Lys Glu Pro Ala Pro Asn Asp Asp
             180                 185                 190

Lys Glu Cys Gly Val Thr Glu Glu Pro Phe Tyr Ala Leu Phe Ser Ser
         195                 200                 205

Leu Gly Ser Phe Tyr Ile Pro Leu Ala Val Ile Leu Val Met Tyr Cys
     210                 215                 220

Arg Val Tyr Ile Val Ala Lys Arg Thr Thr Lys Asn Leu Glu Ala Gly
225                 230                 235                 240

Val Met Lys Glu Met Ser Asn Ser Lys Glu Leu Thr Leu Arg Ile His
                 245                 250                 255

Ser Lys Asn Phe His Glu Asp Thr Leu Ser Ser Thr Lys Ala Lys Gly
             260                 265                 270

His Asn Pro Arg Ser Ser Ile Ala Val Lys Leu Phe Lys Phe Ser Arg
         275                 280                 285

Glu Lys Lys Ala Ala Lys Thr Leu Gly Ile Val Val Gly Met Phe Ile
     290                 295                 300

Leu Cys Trp Leu Pro Phe Phe Ile Ala Leu Pro Leu Gly Ser Leu Phe
```

-continued

|  | 305 |  |  |  | 310 |  |  |  | 315 |  |  |  | 320 |
|---|---|---|---|---|---|---|---|---|---|---|---|---|---|
| Ser | Thr | Leu | Lys | Pro<br>325 | Pro | Asp | Ala | Val | Phe<br>330 | Lys | Val | Val | Phe<br>335 | Leu |
| Gly | Tyr | Phe | Asn<br>340 | Ser | Cys | Leu | Asn | Pro<br>345 | Ile | Ile | Tyr | Pro<br>350 | Cys | Ser | Ser |
| Lys | Glu | Phe<br>355 | Lys | Arg | Ala | Phe | Met<br>360 | Arg | Ile | Leu | Gly | Cys<br>365 | Gln | Cys | Arg |
| Gly | Gly<br>370 | Arg | Arg | Arg | Arg | Arg<br>375 | Arg | Arg | Arg | Leu | Gly<br>380 | Ala | Cys | Ala | Tyr |
| Thr<br>385 | Tyr | Arg | Pro | Trp | Thr<br>390 | Arg | Gly | Gly | Ser | Leu<br>395 | Glu | Arg | Ser | Gln | Ser<br>400 |
| Arg | Lys | Asp | Ser | Leu<br>405 | Asp | Asp | Ser | Gly | Ser<br>410 | Cys | Met | Ser | Gly | Gln<br>415 | Lys |
| Arg | Thr | Leu | Pro<br>420 | Ser | Ala | Ser | Pro | Ser<br>425 | Pro | Gly | Tyr | Leu | Gly<br>430 | Arg | Gly |
| Thr | Gln | Pro<br>435 | Pro | Val | Glu | Leu | Cys<br>440 | Ala | Phe | Pro | Glu | Trp<br>445 | Lys | Pro | Gly |
| Ala | Leu<br>450 | Leu | Ser | Leu | Pro | Glu<br>455 | Pro | Pro | Gly | Arg | Arg<br>460 | Gly | Arg | Leu | Asp |
| Ser<br>465 | Gly | Pro | Leu | Phe | Thr<br>470 | Phe | Lys | Leu | Leu | Gly<br>475 | Asp | Pro | Glu | Ser | Pro<br>480 |
| Gly | Thr | Glu | Ala | Thr<br>485 | Ala | Ser | Asn | Gly | Gly<br>490 | Cys | Asp | Thr | Thr<br>495 | Thr | Asp |
| Leu | Ala | Asn | Gly<br>500 | Gln | Pro | Gly | Phe | Lys<br>505 | Ser | Asn | Met | Pro | Leu<br>510 | Gly | Pro |
| Gly | His | Phe<br>515 |  |  |  |  |  |  |  |  |  |  |  |  |  |

( 2 ) INFORMATION FOR SEQ ID NO:26:

( i ) SEQUENCE CHARACTERISTICS:
    ( A ) LENGTH: 1987 base pairs
    ( B ) TYPE: nucleic acid
    ( C ) STRANDEDNESS: both
    ( D ) TOPOLOGY: both ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:26:

| GAATTCCCTC | CTAGAAGCTG | GAGAGAGCAG | GAGCCTTCGG | TGGGGCAGCT | CAAAATGTAG | 60 |
| GTAACTGCGG | GCCAGGAGCA | GCGCCCAGAT | GCCATCGGTC | CCTGCCTTTG | AGCGTCGACG | 120 |
| GCTGATCTTT | TGGTTTGAGG | GAGAGACTGG | CGCTGGAGTT | TTGAATTCCG | AATCATGTGC | 180 |
| AGAATCGTGA | ATCTTCCCCC | AGCCAGGACG | AATAAGACAG | CGCGGAAAAG | CAGATTCTCG | 240 |
| TAATTCTGGA | ATTGCATGTT | GCAAGGAGTC | TCCTGGATCT | TCGCACCCAG | CTTCGGGTAC | 300 |
| GGGAGGGAGT | CCGGGTCCCG | GCTAGGCCAG | CCCGCAGGTG | GAGAGGGTCC | CCGGCAGCCC | 360 |
| CGCGCGCCCC | TGGCCATGTC | TTTAATGCCC | TGCCCCTTCA | TGTGGCCTTC | TGAGGGTTCC | 420 |
| CAGGGCTGGC | CAGGGTTGTC | TCCCACCCGC | GCGCGCCGTC | TCACCCCCAG | CCAAACCCAC | 480 |
| CTGGCAGGGC | TCCCTCCAGA | AGAGACCTTT | TGATTCCCGG | CTCCCGCGCT | CCCGCCTCCG | 540 |
| CGCCAGCCCG | GGAGGTGGCC | CTGGACAGCC | GGACCTCGCC | CGGCCCCGGC | TGGGACCATG | 600 |
| GTGTTTCTCT | CGGGAAATGC | TTCCGACAGC | TCCAACTGCA | CCCAACCGCC | GGCACCGGTG | 660 |

| | | | | | |
|---|---|---|---|---|---|
| AACATTTCCA | AGGCCATTCT | GCTCGGGGTG | ATCTTGGGGG | GCCTCATTCT | TTTCGGGGTG | 720 |
| CTGGGTAACA | TCCTAGTGAT | CCTCTCCGTA | GCCTGTCACC | GACACCTGCA | CTCAGTCACG | 780 |
| CACTACTACA | TCGTCAACCG | CTAGTGGCGG | TGGCCGACCT | CCTGCTCACC | TCCACGGTGC | 840 |
| TGCCCTTCTC | CGCCATCTTC | GAGGTCCTAG | GCTACTGGGC | CTTCGGCAGG | GTCTTCTGCA | 900 |
| ACATCTGGGC | GGCAGTGGAT | GTGCTGTGCT | GCACCGCGTC | CATCATGGGC | CTCTGCATCA | 960 |
| TCTCCATCGA | CCGCTACATC | GGCGTGAGCT | ACCCGCTGCG | CTACCCAACC | ATCGTCACCC | 1020 |
| AGAGGAGGGG | TCTCATGGCT | CTGCTCTGCG | TCTGGGCACT | CTCCCTGGTC | ATATCCATTG | 1080 |
| GACCCCTCTT | CGGCTGGAGG | CAGCCGGCCC | CCGAGGACGA | GACCATCTGC | CAGATCAACG | 1140 |
| AGGAGCCGGG | CTACGTGCTC | TTCTCGGCTC | TGGGCTCCTT | CTACCTGCCT | CTGGCCATCA | 1200 |
| TCCTGGTCAT | GTACTGCCGC | GTCTACGTGG | TGGCCAAGAG | GGAGAGCCGG | GGCCTCAAGT | 1260 |
| CTGGCCTCAA | GACCGACAAG | TCGGACTCGG | AGCAAGTGAC | GCTCCGCATC | CATCGGAAAA | 1320 |
| ACGCCCCGGC | AGGAGGCAGC | GGGATGGCCA | GCGCCAAGAC | CAAGACGCAC | TTCTCAGTGA | 1380 |
| GGCTCCTCAA | GTTCTCCCGG | GAGAAGAAAG | CGGCCAAAAC | GCTGGGCATC | GTGGTCGGCT | 1440 |
| GCTTCGTCCT | CTGCTGGCTG | CCTTTTTTCT | TAGTCATGCC | CATTGGGTCT | TTCTTCCCTG | 1500 |
| ATTTCAAGCC | CTCTGAAACA | GTTTTTAAAA | TAGTATTTTG | GCTCGGATAT | CTAAACAGCT | 1560 |
| GCATCAACCC | CATCATATAC | CCATGCTCCA | GCCAAGAGTT | CAAAAAGGCC | TTTCAGAATG | 1620 |
| TCTTGAGAAT | CCAGTGTCTC | CGCAGAAAGC | AGTCGCTAGT | TCCAAACATG | CCCTGGGCTA | 1680 |
| CACCCTGCAC | CCGCCCAGCC | AGGCCGTGGA | AGGGCAACAC | AAGGACATGG | TGCGCATCCC | 1740 |
| CGTGGGATCA | AGAGAGACCT | TCTACAGGAT | CTCCAAGACG | GATGGCGTTT | GTGAATGGAA | 1800 |
| ATTTTTCTCT | TCCATGCCCC | GTGGATCTGC | CAGGATTACA | GTGTCCAAAG | ACCAATCCTC | 1860 |
| CTGTACCACA | GCCCGGGTGA | GAAGTAAAAG | CTTTTTGCAG | GTCTGCTGCT | GTGTAGGGCC | 1920 |
| CTCAACCCCC | AGCCTTGACA | AGAACCATCA | AGTTCCAACC | ATTAAGGTCC | ACACCATCTC | 1980 |
| CCTCAGT | | | | | | 1987 |

( 2 ) INFORMATION FOR SEQ ID NO:27:

( i ) SEQUENCE CHARACTERISTICS:
        ( A ) LENGTH: 1997 base pairs
        ( B ) TYPE: nucleic acid
        ( C ) STRANDEDNESS: both
        ( D ) TOPOLOGY: both ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:27:

| | | | | | |
|---|---|---|---|---|---|
| AATTCCCTCC | TAGAAGCTGG | AGAGAGCAGG | AGCCTTCGGT | GGGGCAGCTC | AAAATGTAGG | 60 |
| TAACTGCGGG | CCAGGAGCAG | CGCCCAGATG | CCATCGGTCC | CTGCCTTTGA | GCGTCGACGG | 120 |
| CTGATCTTTT | GGTTTGAGGG | AGAGACTGGC | GCTGGAGTTT | TGAATTCCGA | ATCATGTGCA | 180 |
| GAATCGTGAA | TCTTCCCCCA | GCCAGGACGA | ATAAGACAGC | GCGGAAAAGC | AGATTCTCGT | 240 |
| AATTCTGGAA | TTGCATGTTG | CAAGGAGTCT | CCTGGATCTT | CGCACCCAGC | TTCGGGTACG | 300 |
| GGAGGGAGTC | CGGGTCCCGG | CTAGGCCAGC | CCGCAGGTGG | AGAGGGTCCC | CGGCAGCCCC | 360 |
| GCGCGCCCCT | GGCCATGTCT | TTAATGCCCT | GCCCCTTCAT | GTGGCCTTCT | GAGGGTTCCC | 420 |
| AGGGCTGGCC | AGGGTTGTCT | CCCACCCGCG | CGCGCCGTCT | CACCCCCAGC | CAAACCCACC | 480 |
| TGGCAGGGCT | CCCTCCAGAA | GAGACCTTTT | GATTCCCGGC | TCCCGCGCTC | CCGCCTCCGC | 540 |

```
GCCAGCCCGG GAGGTGGCCC TGGACAGCCG GACCTCGCCC GGCCCCGGCT GGGACCATGG      600
TGTTTCTCTC GGGAAATGCT TCCGACAGCT CCAACTGCAC CCAACCGCCG GCACCGGTGA      660
ACATTTCCAA GGCCATTCTG CTCGGGGTGA TCTTGGGGGG CCTCATTCTT TTCGGGGTGC      720
TGGGTAACAT CCTAGTGATC CTCTCCGTAG CCTGTCACCG ACACCTGCAC TCAGTCACGC      780
ACTACTACAT CGTCAACCTG GCGGTGGCCG ACCTCCTGCT CACCTCCACG GTGCTGCCCT      840
TCTCCGCCAT CTTCGAGGTC CTAGGCTACT GGGCCTTCGG CAGGGTCTTC TGCAACATCT      900
GGGCGGCAGT GGATGTGCTG TGCTGCACCG CGTCCATCAT GGGCCTCTGC ATCATCTCCA      960
TCGACCGCTA CATCGGCGTG AGCTACCCGC TGCGCTACCC AACCATCGTC ACCCAGAGGA      1020
GGGGTCTCAT GGCTCTGCTC TGCGTCTGGG CACTCTCCCT GGTCATATCC ATTGGACCCC      1080
TCTTCGGCTG GAGGCAGCCG GCCCCCGAGG ACGAGACCAT CTGCCAGATC AACGAGGAGC      1140
CGGGCTACGT GCTCTTCTCG GCTCTGGGCT CCTTCTACCT GCCTCTGGCC ATCATCCTGG      1200
TCATGTACTG CCGCGTCTAC GTGGTGGCCA AGAGGGAGAG CCGGGGCCTC AAGTCTGGCC      1260
TCAAGACCGA CAAGTCGGAC TCGGAGCAAG TGACGCTCCG CATCCATCGG AAAAACGCCC      1320
CGGCAGGAGG CAGCGGGATG GCCAGCGCCA AGACCAAGAC GCACTTCTCA GTGAGGCTCC      1380
TCAAGTTCTC CCGGGAGAAG AAAGCGGCCA AACGCTGGGC ATCGTGGTCG GCTGCTTCG      1440
TCCTCTGCTG GCTGCCTTTT TTCTTAGTCA TGCCCATTGG GTCTTTCTTC CCTGATTTCA      1500
AGCCCTCTGA AACAGTTTTT AAAATAGTAT TTGGCTCGG ATATCTAAAC AGCTGCATCA      1560
ACCCCATCAT ATACCCATGC TCCAGCCAAG AGTTCAAAAA GGCCTTTCAG AATGTCTTGA      1620
GAATCCAGTG TCTCTGCAGA AAGCAGTCTT CCAAACATGC CCTGGGCTAC ACCCTGCACC      1680
CGCCCAGCCA GGCCGTGGAA GGGCAACACA AGGACATGGT GCGCATCCCC GTGGGATCAA      1740
GAGAGACCTT CTACAGGATC TCCAAGACGG ATGGCGTTTG TGAATGGAAA TTTTTCTCTT      1800
CCATGCCCCG TGGATCTGCC AGGATTACAG TGTCCAAAGA CCAATCCTCC TGTACCACAG      1860
CCCGGGTGAG AAGTAAAAGC TTTTTGCAGG TCTGCTGCTG TGTAGGGCCC TCAACCCCCA      1920
GCCTTGACAA GAACCATCAA GTTCCAACCA TTAAGGTCCA CACCATCTCC CTCAGTGAGA      1980
ACGGGAGGA AGTCTAG                                                     1997
```

(2) INFORMATION FOR SEQ ID NO:28:

(i) SEQUENCE CHARACTERISTICS:
    (A) LENGTH: 466 amino acids
    (B) TYPE: amino acid
    (C) STRANDEDNESS: single
    (D) TOPOLOGY: linear (i i) MOLECULE TYPE: protein (i i i) HYPOTHETICAL: NO (v) FRAGMENT TYPE: N-terminal (x i) SEQUENCE DESCRIPTION: SEQ ID NO:28:

```
Met Val Phe Leu Ser Gly Asn Ala Ser Asp Ser Ser Asn Cys Thr Gln
 1               5                  10                  15

Pro Pro Ala Pro Val Asn Ile Ser Lys Ala Ile Leu Leu Gly Val Ile
            20                  25                  30

Leu Gly Gly Leu Ile Leu Phe Gly Val Leu Gly Asn Ile Leu Val Ile
            35                  40                  45

Leu Ser Val Ala Cys His Arg His Leu His Ser Val Thr His Tyr Tyr
        50                  55                  60
```

-continued

| | | | | | | | | | | | | | | | |
|---|---|---|---|---|---|---|---|---|---|---|---|---|---|---|---|
| Ile | Val | Asn | Leu | Ala | Val | Ala | Asp | Leu | Leu | Leu | Thr | Ser | Thr | Val | Leu |
| 65 | | | | | 70 | | | | 75 | | | | | | 80 |
| Pro | Phe | Ser | Ala | Ile | Phe | Glu | Val | Leu | Gly | Tyr | Trp | Ala | Phe | Gly | Arg |
| | | | | 85 | | | | | 90 | | | | | 95 | |
| Val | Phe | Cys | Asn | Ile | Trp | Ala | Ala | Val | Asp | Val | Leu | Cys | Cys | Thr | Ala |
| | | | 100 | | | | | 105 | | | | | 110 | | |
| Ser | Ile | Met | Gly | Leu | Cys | Ile | Ile | Ser | Ile | Asp | Arg | Tyr | Ile | Gly | Val |
| | | 115 | | | | | 120 | | | | | 125 | | | |
| Ser | Tyr | Pro | Leu | Arg | Tyr | Pro | Thr | Ile | Val | Thr | Gln | Arg | Arg | Gly | Leu |
| | 130 | | | | | 135 | | | | | 140 | | | | |
| Met | Ala | Leu | Leu | Cys | Val | Trp | Ala | Leu | Ser | Leu | Val | Ile | Ser | Ile | Gly |
| 145 | | | | | 150 | | | | 155 | | | | | | 160 |
| Pro | Leu | Phe | Gly | Trp | Arg | Gln | Pro | Ala | Pro | Glu | Asp | Glu | Thr | Ile | Cys |
| | | | | 165 | | | | | 170 | | | | | 175 | |
| Gln | Ile | Asn | Glu | Glu | Pro | Gly | Tyr | Val | Leu | Phe | Ser | Ala | Leu | Gly | Ser |
| | | | 180 | | | | | 185 | | | | | 190 | | |
| Phe | Tyr | Leu | Pro | Leu | Ala | Ile | Ile | Leu | Val | Met | Tyr | Cys | Arg | Val | Tyr |
| | | 195 | | | | | 200 | | | | | 205 | | | |
| Val | Val | Ala | Lys | Arg | Glu | Ser | Arg | Gly | Leu | Lys | Ser | Gly | Leu | Lys | Thr |
| | 210 | | | | | 215 | | | | | 220 | | | | |
| Asp | Lys | Ser | Asp | Ser | Glu | Gln | Val | Thr | Leu | Arg | Ile | His | Arg | Lys | Asn |
| 225 | | | | | 230 | | | | | 235 | | | | | 240 |
| Ala | Pro | Ala | Gly | Gly | Ser | Gly | Met | Ala | Ser | Ala | Lys | Thr | Lys | Thr | His |
| | | | | 245 | | | | | 250 | | | | | 255 | |
| Phe | Ser | Val | Arg | Leu | Leu | Lys | Phe | Ser | Arg | Glu | Lys | Lys | Ala | Ala | Lys |
| | | | 260 | | | | | 265 | | | | | 270 | | |
| Thr | Leu | Gly | Ile | Val | Val | Gly | Cys | Phe | Val | Leu | Cys | Trp | Leu | Pro | Phe |
| | | 275 | | | | | 280 | | | | | 285 | | | |
| Phe | Leu | Val | Met | Pro | Ile | Gly | Ser | Phe | Phe | Pro | Asp | Phe | Lys | Pro | Ser |
| | 290 | | | | | 295 | | | | | 300 | | | | |
| Glu | Thr | Val | Phe | Lys | Ile | Val | Phe | Trp | Leu | Gly | Tyr | Leu | Asn | Ser | Cys |
| 305 | | | | | 310 | | | | | 315 | | | | | 320 |
| Ile | Asn | Pro | Ile | Ile | Tyr | Pro | Cys | Ser | Ser | Gln | Glu | Phe | Lys | Lys | Ala |
| | | | | 325 | | | | | 330 | | | | | 335 | |
| Phe | Gln | Asn | Val | Leu | Arg | Ile | Gln | Cys | Leu | Cys | Arg | Lys | Gln | Ser | Ser |
| | | | 340 | | | | | 345 | | | | | 350 | | |
| Lys | His | Ala | Leu | Gly | Tyr | Thr | Leu | His | Pro | Pro | Ser | Gln | Ala | Val | Glu |
| | | 355 | | | | | 360 | | | | | 365 | | | |
| Gly | Gln | His | Lys | Asp | Met | Val | Arg | Ile | Pro | Val | Gly | Ser | Arg | Glu | Thr |
| | 370 | | | | | 375 | | | | | 380 | | | | |
| Phe | Tyr | Arg | Ile | Ser | Lys | Thr | Asp | Gly | Val | Cys | Glu | Trp | Lys | Phe | Phe |
| 385 | | | | | 390 | | | | | 395 | | | | | 400 |
| Ser | Ser | Met | Pro | Arg | Gly | Ser | Ala | Arg | Ile | Thr | Val | Ser | Lys | Asp | Gln |
| | | | | 405 | | | | | 410 | | | | | 415 | |
| Ser | Ser | Cys | Thr | Thr | Ala | Arg | Val | Arg | Ser | Lys | Ser | Phe | Leu | Gln | Val |
| | | | 420 | | | | | 425 | | | | | 430 | | |
| Cys | Cys | Cys | Val | Gly | Pro | Ser | Thr | Pro | Ser | Leu | Asp | Lys | Asn | His | Gln |
| | | 435 | | | | | 440 | | | | | 445 | | | |
| Val | Pro | Thr | Ile | Lys | Val | His | Thr | Ile | Ser | Leu | Ser | Glu | Asn | Gly | Glu |
| 450 | | | | | 455 | | | | | 460 | | | | | | |
| Glu | Val | | | | | | | | | | | | | | |
| 465 | | | | | | | | | | | | | | | |

( 2 ) INFORMATION FOR SEQ ID NO:29:

( i ) SEQUENCE CHARACTERISTICS:
    ( A ) LENGTH: 1776 base pairs
    ( B ) TYPE: nucleic acid
    ( C ) STRANDEDNESS: both
    ( D ) TOPOLOGY: both ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:29:

| | | | | | |
|---|---|---|---|---|---|
| CTCCCTGCCG | GCCGCTCGTT | CTGTGCCCCG | GCCCGGCCAC | CGACGGCCGG | CGTTGAGATG | 60 |
| ACTTTCCGCG | ATCTCCTGAG | CGTCAGTTTC | GAGGGACCCC | GCCCGGACAG | CAGCGCAGGG | 120 |
| GGCTCCAGCG | CGGGCGGCGG | CGGGGGCGGC | GCGGGCGGCG | CGGCCCCCTC | GGAGGGCCCG | 180 |
| GCGGTGGGCG | GCGTGCCGGG | GGGCGCGGGC | GGCGGCGGCG | GCGTGGTGGG | CGCAGGCAGC | 240 |
| GGCGAGGACA | ACCGGAGCTC | CGCGGGGGAG | CCGGGGAGCG | CGGGCGCGGG | CGGCGACGTG | 300 |
| AATGGCACGG | CGGCCGTCGG | GGGACTGGTG | GTGAGCGCGC | AGGGCGTGGG | CGTGGGCGTC | 360 |
| TTCCTGGCAG | CCTTCATCCT | TATGGCCGTG | GCAGGTAACC | TGCTTGTCAT | CCTCTCAGTG | 420 |
| GCCTGCAACC | GCCACCTGCA | GACCGTCACC | AACTATTTCA | TCGTGAACCT | GGCCGTGGCC | 480 |
| GACCTGCTGC | TGAGCGCCAC | CGTACTGCCC | TTCTCGGCCA | CCATGGAGGT | TCTGGGCTTC | 540 |
| TGGGCCTTTG | GCCGCGCCTT | CTGCGACGTA | TGGGCCGCCG | TGGACGTGCT | GTGCTGCACG | 600 |
| GCCTCCATCC | TCAGCCTCTG | CACCATCTCC | GTGGACCGGT | ACGTGGGCGT | GCGCCACTCA | 660 |
| CTCAAGTACC | CAGCCATCAT | GACCGAGCGC | AAGGCGGCCG | CCATCCTGGC | CCTGCTCTGG | 720 |
| GTCGTAGCCC | TGGTGGTGTC | CGTAGGGCCC | CTGCTGGGCT | GGAAGGAGCC | CGTGCCCCCT | 780 |
| GACGAGCGCT | TCTGCGGTAT | CACCGAGGAG | GCGGGCTACG | CTGTCTTCTC | CTCCGTGTGC | 840 |
| TCCTTCTACC | TGCCCATGGC | GGTCATCGTG | GTCATGTACT | GCCGCGTGTA | CGTGGTCGCG | 900 |
| CGCAGCACCA | CGCGCAGCCT | CGAGGCGGGC | GTCAAGCGCG | AGCGAGGCAA | GGCCTCCGAG | 960 |
| GTGGTGCTGC | GCATCCACTG | TCGCGGCGCG | GCCACGGGCG | CCGACGGGGC | GCACGGCATG | 1020 |
| CGCAGCGCCA | AGGGCCACAC | CTTCCGCAGC | TCGCTCTCCG | TGCGCCTGCT | CAAGTTCTCC | 1080 |
| CGTGAGAAGA | AAGCGGCCAA | GACTCTGGCC | ATCGTCGTGG | GTGTCTTCGT | GCTCTGCTGG | 1140 |
| TTCCCTTTCT | TCTTTGTCCT | GCCGCTCGGC | TCCTTGTTCC | CGCAGCTGAA | GCCATCGGAG | 1200 |
| GGCGTCTTCA | AGGTCATCTT | CTGGCTCGGC | TACTTCAACA | GCTGCGTGAA | CCCGCTCATC | 1260 |
| TACCCCTGTT | CCAGCCGCGA | GTTCAAGCGC | GCCTTCCTCC | GTCTCCTGCG | CTGCCAGTGC | 1320 |
| CGTCGTCGCC | GGCGCCGCCG | CCCTCTCTGG | CGTGTCTACG | GCCACCACTG | GCGGGCCTCC | 1380 |
| ACCAGCGGCC | TGCGCCAGGA | CTGCGCCCCG | AGTTCGGGCG | ACGCGCCCCC | CGGAGCGCCG | 1440 |
| CTGGCCCTCA | CCGCGCTCCC | CGACCCCGAC | CCCGAACCCC | CAGGCACGCC | CGAGATGCAG | 1500 |
| GCTCCGGTCG | CCAGCCGTCG | AAAGCCACCC | AGCGCCTTCC | GCGAGTGGAG | GCTGCTGGGG | 1560 |
| CCGTTCCGGA | GACCCACGAC | CCAGCTGCGC | GCCAAAGTCT | CCAGCCTGTC | GCACAAGATC | 1620 |
| CGCGCCGGGG | GCGCGCAGCG | CGCAGAGGCA | GCGTGCGCCC | AGCGCTCAGA | GGTGGAGGCT | 1680 |
| GTGTCCCTAG | GCGTCCACA | CGAGGTGGCC | GAGGGCGCCA | CCTGCCAGGC | CTACGAATTG | 1740 |
| GCCGACTACA | GCAACCTACG | GGAGACCGAT | ATTTAA | | | 1776 |

( 2 ) INFORMATION FOR SEQ ID NO:30:

( i ) SEQUENCE CHARACTERISTICS:
        ( A ) LENGTH: 572 amino acids (B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:30:

| Met | Thr | Phe | Arg | Asp | Leu | Leu | Ser | Val | Ser | Phe | Glu | Gly | Pro | Arg | Pro |
|---|---|---|---|---|---|---|---|---|---|---|---|---|---|---|---|
| 1 | | | | 5 | | | | | 10 | | | | | 15 | |
| Asp | Ser | Ser | Ala | Gly | Gly | Ser | Ser | Ala | Gly | Gly | Gly | Gly | Gly | Gly | Ala |
| | | | 20 | | | | | 25 | | | | | 30 | | |
| Gly | Gly | Ala | Ala | Pro | Ser | Glu | Gly | Pro | Ala | Val | Gly | Gly | Val | Pro | Gly |
| | | 35 | | | | | 40 | | | | | 45 | | | |
| Gly | Ala | Gly | Gly | Gly | Gly | Gly | Val | Val | Gly | Ala | Gly | Ser | Gly | Glu | Asp |
| | 50 | | | | | 55 | | | | | 60 | | | | |
| Asn | Arg | Ser | Ser | Ala | Gly | Glu | Pro | Gly | Ser | Ala | Gly | Ala | Gly | Gly | Asp |
| 65 | | | | | 70 | | | | | 75 | | | | | 80 |
| Val | Asn | Gly | Thr | Ala | Ala | Val | Gly | Gly | Leu | Val | Val | Ser | Ala | Gln | Gly |
| | | | | 85 | | | | | 90 | | | | | 95 | |
| Val | Gly | Val | Gly | Val | Phe | Leu | Ala | Ala | Phe | Ile | Leu | Met | Ala | Val | Ala |
| | | | 100 | | | | | 105 | | | | | 110 | | |
| Gly | Asn | Leu | Leu | Val | Ile | Leu | Ser | Val | Ala | Cys | Asn | Arg | His | Leu | Gln |
| | | 115 | | | | | 120 | | | | | 125 | | | |
| Thr | Val | Thr | Asn | Tyr | Phe | Ile | Val | Asn | Leu | Ala | Val | Ala | Asp | Leu | Leu |
| | 130 | | | | | 135 | | | | | 140 | | | | |
| Leu | Ser | Ala | Thr | Val | Leu | Pro | Phe | Ser | Ala | Thr | Met | Glu | Val | Leu | Gly |
| 145 | | | | | 150 | | | | | 155 | | | | | 160 |
| Phe | Trp | Ala | Phe | Gly | Arg | Ala | Phe | Cys | Asp | Val | Trp | Ala | Ala | Val | Asp |
| | | | | 165 | | | | | 170 | | | | | 175 | |
| Val | Leu | Cys | Cys | Thr | Ala | Ser | Ile | Leu | Ser | Leu | Cys | Thr | Ile | Ser | Val |
| | | | 180 | | | | | 185 | | | | | 190 | | |
| Asp | Arg | Tyr | Val | Gly | Val | Arg | His | Ser | Leu | Lys | Tyr | Pro | Ala | Ile | Met |
| | | 195 | | | | | 200 | | | | | 205 | | | |
| Thr | Glu | Arg | Lys | Ala | Ala | Ala | Ile | Leu | Ala | Leu | Leu | Trp | Val | Val | Ala |
| | 210 | | | | | 215 | | | | | 220 | | | | |
| Leu | Val | Val | Ser | Val | Gly | Pro | Leu | Leu | Gly | Trp | Lys | Glu | Pro | Val | Pro |
| 225 | | | | | 230 | | | | | 235 | | | | | 240 |
| Pro | Asp | Glu | Arg | Phe | Cys | Gly | Ile | Thr | Glu | Glu | Ala | Gly | Tyr | Ala | Val |
| | | | | 245 | | | | | 250 | | | | | 255 | |
| Phe | Ser | Ser | Val | Cys | Ser | Phe | Tyr | Leu | Pro | Met | Ala | Val | Ile | Val | Val |
| | | | 260 | | | | | 265 | | | | | 270 | | |
| Met | Tyr | Cys | Arg | Val | Tyr | Val | Val | Ala | Arg | Ser | Thr | Thr | Arg | Ser | Leu |
| | | 275 | | | | | 280 | | | | | 285 | | | |
| Glu | Ala | Gly | Val | Lys | Arg | Glu | Arg | Gly | Lys | Ala | Ser | Glu | Val | Val | Leu |
| | 290 | | | | | 295 | | | | | 300 | | | | |
| Arg | Ile | His | Cys | Arg | Gly | Ala | Ala | Thr | Gly | Ala | Asp | Gly | Ala | His | Gly |
| 305 | | | | | 310 | | | | | 315 | | | | | 320 |
| Met | Arg | Ser | Ala | Lys | Gly | His | Thr | Phe | Arg | Ser | Ser | Leu | Ser | Val | Arg |
| | | | | 325 | | | | | 330 | | | | | 335 | |
| Leu | Leu | Lys | Phe | Ser | Arg | Glu | Lys | Lys | Ala | Ala | Lys | Thr | Leu | Ala | Ile |
| | | | | 340 | | | | | 345 | | | | | 350 | |

-continued

| | | | | | | | | | | | | | | | |
|---|---|---|---|---|---|---|---|---|---|---|---|---|---|---|---|
| Val | Val | Gly 355 | Val | Phe | Val | Leu | Cys 360 | Trp | Phe | Pro | Phe 365 | Phe | Val | Leu | |
| Pro | Leu 370 | Gly | Ser | Leu | Phe | Pro 375 | Gln | Leu | Lys | Pro | Ser 380 | Glu | Gly | Val | Phe |
| Lys 385 | Val | Ile | Phe | Trp | Leu 390 | Gly | Tyr | Phe | Asn | Ser 395 | Cys | Val | Asn | Pro | Leu 400 |
| Ile | Tyr | Pro | Cys | Ser 405 | Ser | Arg | Glu | Phe | Lys 410 | Arg | Ala | Phe | Leu | Arg 415 | Leu |
| Leu | Arg | Cys | Gln 420 | Cys | Arg | Arg | Arg | Arg 425 | Arg | Arg | Arg | Pro | Leu 430 | Trp | Arg |
| Val | Tyr | Gly 435 | His | His | Trp | Arg | Ala 440 | Ser | Thr | Ser | Gly | Leu 445 | Arg | Gln | Asp |
| Cys | Ala 450 | Pro | Ser | Ser | Gly | Asp 455 | Ala | Pro | Pro | Gly | Ala 460 | Pro | Leu | Ala | Leu |
| Thr 465 | Ala | Leu | Pro | Asp | Pro 470 | Asp | Pro | Glu | Pro | Pro 475 | Gly | Thr | Pro | Glu | Met 480 |
| Gln | Ala | Pro | Val | Ala 485 | Ser | Arg | Arg | Lys | Pro 490 | Pro | Ser | Ala | Phe | Arg 495 | Glu |
| Trp | Arg | Leu | Leu 500 | Gly | Pro | Phe | Arg | Arg 505 | Pro | Thr | Thr | Gln | Leu 510 | Arg | Ala |
| Lys | Val | Ser 515 | Ser | Leu | Ser | His | Lys 520 | Ile | Arg | Ala | Gly | Gly 525 | Ala | Gln | Arg |
| Ala | Glu 530 | Ala | Ala | Cys | Ala | Gln 535 | Arg | Ser | Glu | Val | Glu 540 | Ala | Val | Ser | Leu |
| Gly 545 | Val | Pro | His | Glu | Val 550 | Ala | Glu | Gly | Ala | Thr 555 | Cys | Gln | Ala | Tyr | Glu 560 |
| Leu | Ala | Asp | Tyr | Ser 565 | Asn | Leu | Arg | Glu | Thr 570 | Asp | Ile | | | | |

( 2 ) INFORMATION FOR SEQ ID NO:31:

( i ) SEQUENCE CHARACTERISTICS:
        ( A ) LENGTH: 16 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:31:

GAATCCCGAC CTGGAC                                                        1 6

( 2 ) INFORMATION FOR SEQ ID NO:32:

( i ) SEQUENCE CHARACTERISTICS:
        ( A ) LENGTH: 14 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:32:

GGATCCTCAG GGTC                                                         1 4

(2) INFORMATION FOR SEQ ID NO:33:

(i) SEQUENCE CHARACTERISTICS:
　　　　(A) LENGTH: 19 base pairs
　　　　(B) TYPE: nucleic acid
　　　　(C) STRANDEDNESS: both
　　　　(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:33:

CCATGGTGTT TCTCTCGGG　　　　19

(2) INFORMATION FOR SEQ ID NO:34:

(i) SEQUENCE CHARACTERISTICS:
　　　　(A) LENGTH: 18 base pairs
　　　　(B) TYPE: nucleic acid
　　　　(C) STRANDEDNESS: both
　　　　(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:34:

GACGCGGCAG TACATGAC　　　　18

(2) INFORMATION FOR SEQ ID NO:35:

(i) SEQUENCE CHARACTERISTICS:
　　　　(A) LENGTH: 21 base pairs
　　　　(B) TYPE: nucleic acid
　　　　(C) STRANDEDNESS: both
　　　　(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:35:

GTCATGATGG CTGGGTACTT G　　　　21

ALPHA IC ADRENERGIC RECEPTOR ANTAGONISTS

CROSS-REFERENCE

This application is a 371 of PCT/US95/04590 filed Apr. 13, 1995, which is a C-I-P of Ser. No. 08/229,276 filed Apr. 13, 1994 now abandoned.

BACKGROUND OF THE INVENTION

1. Field of the Invention

This invention relates to certain novel compounds and derivatives thereof, their synthesis, and their use as selective alpha-1c adrenoceptor antagonists. One application of these compounds is in the treatment of benign prostatic hypertrophy. These compounds are selective in their ability to relax smooth muscle tissue enriched in the alpha1C receptor subtype without at the same time inducing orthostatic hypotension. One such tissue is found surrounding the urethral lining. Therefore, one utility of the instant compounds is to provide acute relief to males suffering from benign prostatic hyperplasia, by permitting less hindered urine flow. Another utility of the instant compounds is provided by combination with a human 5-alpha reductase inhibitory compound, such that both acute and chronic relief from the effects of benign prostatic hyperplasia are achieved. Other advantages of the instant compounds are appreciated from the complete disclosure.

2. Background

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into $\alpha_1$, $\alpha_2$, $\beta_1$, and $\beta_2$ subtypes. Functional differences between $\alpha_1$ and $\beta_2$ receptors have been recognized, and compounds which exhibit selective binding between these two subtypes have been developed. Thus, in WO 92/0073, the selective ability of the R(+) enantiomer of terazosin to selectively bind to adrenergic receptors of the alpha 1 subtype was reported. The ($\alpha_1/\alpha_2$) selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective alpha-adrenergic blockers, such as phenoxybenzamine and phentolamine, is limited by their $\alpha_2$ adrenergic receptor mediated induction of increased plasma catecholamine concentration and the attendant physiological sequelae (increased heart rate and smooth muscle contraction).

For a general background on the $\alpha$-adrenergic receptors, the reader's attention is directed to Robert R. Ruffolo, Jr., $\alpha$-*Adrenoreceptors: Molecular Biology, Biochemistry and Pharmacology*, (*Progress in Basic and Clinical Pharmacology* series, Karger, 1991), wherein the basis of $\alpha_1/\alpha_2$ subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting $\alpha$-adrenergic receptor affinity was explored.

The cloning, sequencing and expression of alpha receptor subtypes from animal tissues has led to the subclassification of the $\alpha_1$ receptors into $\alpha_{1A}$. (Lomasney, et al., *J. Biol. Chem.*, 266:6365–6369 (1991), rat $\alpha_{1A}$; Bruno et al., *BBRC*, 179:1485–1490 (1991), human $\alpha_{1A}$). $\alpha_{1B}$ (Cotecchia, et al., *PNAS*, 85;7159–7163 (1988), hamster $a_{1B}$; Libert, et al., *Science*, (1989), dog $\alpha_{1B}$; Ramarao, et al., *J. Biol. Chem.*, 267:21936–21945 (1992), human $\alpha_{1B}$), and most recently, in a study using bovine brain, a new $\alpha_{1C}$ subtype was proposed (Schwinn, et al., *J. Biol. Chem.*, 265:8183–8189, 1990; Hirasawa et al., *BBRC* 195:902–909 (1993), described the cloning, functional expression and tissue distribution of a human $\alpha_{1C}$ adrenergic receptor; Hoehe et al., *Human Mol. Genetics* 1(5):349 (8/92) noted the existence of a two-allele Pst1 restriction fragment polymorphism in the $\alpha_{1C}$ adrenergic receptor gene; another study suggests that there may even be an alpha-1D receptor subtype, see Perez et al., *Mol. Pharm.*, 40:876–883, 1992). Each $\alpha_1$ receptor subtype exhibits its own pharmacologic and tissue specificities. Schwinn and coworkers noted that the cloned bovine $\alpha_{1C}$ receptor exhibited pharmacological properties proposed for the $\alpha_{1A}$ subtype. Nonetheless, based on its non-expression in tissues where the $\alpha_{1A}$ subtype is expressed, and its sensitivity to chloroethylclonidine, the receptor was given a new designation.

The differences in the $\alpha$-adrenergic receptor subtypes have relevance in pathophysiologic conditions. Benign prostatic hypertrophy, BPH, is an illness typically affecting men over fifty years of age, increasing in severity with increasing age. The symptoms of the condition include, but are not limted to, increased difficulty in urination and sexual dysfunction. These symptoms are induced by enlargement, or hypertrophy, of the prostate gland. As the prostate increases in size, it impinges on free-flow of fluids through the male urethra. Concommitantly, the increased noradrenergic innervation of the enlarged prostate leads to an increased adrenergic tone of the bladder neck and urethra, further restricting the flow of urine through the urethra.

The mechanism of prostatic hypertrophy is well understood. The male hormone, 5$\alpha$-dihydrotestosterone has been identified as the principal culprit. The continual production of 5$\alpha$-dihydrotestosterone by the male testes induces incremental growth of the prostate gland throughout the life of the male. Beyond the age of about fifty years, in many men, this enlarged gland begins to obstruct the urethra with the pathologic symptoms noted above.

The elucidation of the mechanism summarized above has resulted in the recent development of effective agents to control, and in many cases reverse, the pernicious advance of BPH. In the forefront of these agents is Merck & Co., Inc.s' product PROSCAR® (finasteride). The effect of this compound is to inhibit the enzyme testosterone 5-alpha reductase, which converts testosterone into 5$\alpha$-dihydrotesterone, resulting in a reduced rate of prostatic enlargement, and often reduction in prostatic mass.

The development of such agents as PROSCAR® bodes well for the long-term control of BPH. However, as may be appreciated from the lengthy development of the syndrome, its reversal also is not immediate. In the interim, those males suffering with BPH continue to suffer, and may in fact lose hope that the agents are working sufficiently rapidly.

In response to this problem, one solution is to identify pharmaceutically active compounds which complement slower-acting therapeutics by providing acute relief. Agents which induce relaxation of the urethral smooth muscle, by binding to alpha-i adrenergic receptors, thus reducing the increased adrenergic tone due to the disease, would be good candidates for this activity. Thus, one such agent is alfuzosin, which is reported in EP 0 204597 to induce urination in cases of prostatic hypertrophy. Likewise, in WO 92/0073, the selective ability of the R(+) enantiomer of terazosin to bind to adrenergic receptors of the $\alpha_1$ subtype was reported. In addition, in WO 92/161213, hereby incorporated by reference, combinations of 5-alpha-reductase inhibitory compounds and alpha-adrenergic receptor blockers (terazosin, doxazosin, prazosin, bunazosin, indoramin, alfuzosin) were disclosed. However, no information as to the $\alpha_{1A}$, $\alpha_{1B}$, or $\alpha_{1C}$ subtype specificity of these compounds was provided as these refinements were not yet available. Current therapy for BPH uses existing non-selective alpha-1 antagonists such as prazosin (Minipress, Pfizer) or Terazosin (Hytrin, Abbott). These non-selective antagonists suffer from side effects related to antagonism of the alpha-1a and alpha-1b receptors in the peripheral vasculature, eg., orthostatic hypotension and syncope.

Typically, identification of active compounds is through use of animal tissues known to be enriched in adrenergic receptors. Thus, rat tissues have been used to screen for potential adrenergic receptor antagonists. However, because of species variability, compounds which appear active in animal tissue may not be active or sufficiently selective in humans. This results in substantial wastage of time and effort, particularly where high volume compound screening programs are employed. There is also the danger that compounds, which might be highly effective in humans, would be missed because of their absence of appreciable affinity for the heterologous animal receptors. In this regard, it has been noted that even single amino acid changes between the sequence of biologically active proteins in one species may give rise to substantial pharmacological differences. Thus, Fong et al., (*J. Biol. Chem.*, 267:25668–25671, 1992) showed that there are 22 divergent amino acid residues between the sequence of the human neurokinin-1 receptor and the homologous rat receptor. They further showed, in studies with mutant receptors, that substitution of only two amino acid residues was both necessary and sufficient to reproduce the rat receptor's antagonist binding affinity in the human receptor. Oksenberg et al., (*Nature* 360:161–163, 1992) showed that a single amino-acid difference confers major pharmacological variation between the human and the rodent 5-hydroxytryptamine receptors. Likewise, Kuhse et al., (*Neuron*, 5:867–873, 1990) showed that a single amino-acid exchange alters the pharmacology of the neonatal rat glycine receptor subunit. This difficulty and unpredictability has resulted in a need for a compound screen which will identify compounds that will be active in humans.

These problems are solved by cloning the human adrenergic receptor of the $\alpha_{1C}$ subtype and the use of a screening assay which enables identification of compounds which specifically interact with the human $\alpha$1C adrenergic receptor. Marshall et al (*Br. J. Pharm.*, 107:327 (1992)) speculated that compounds which specifically interact with the $\alpha$1C adrenergic receptor may be responsible for contraction of the human prostate. As disclosed in the instant patent disclosure, a cloned human $\alpha_{1C}$ adrenergic receptor and a method for identifying compounds which bind the human $\alpha_{1C}$ receptor has now made possible the identification of specific human $\alpha_{1C}$ adrenergic receptor antagonists. In the instant patent disclosure, we reveal novel compounds which we have discovered specifically bind the human $\alpha_{1C}$ receptor. These compounds are further tested for binding to other human alpha 1 receptor subtypes, as well as counterscreened against other types of receptors, thus defining the specificity of the compounds for the human $\alpha_{1C}$ adrenergic receptor.

Compounds of his invention are used to reduce the acute symptoms of BPH. Thus, compounds of this invention may be used alone or in conjunction with a more long-term anti-BPH therapeutics, such as testosterone 5-alpha reductase inhibitors, including PROSCAR® (finasteride). Aside from their utility as anti-BPH agents, these compounds may be used to induce highly tissue-specific, localized $\alpha_{1C}$ adrenergic receptor blockade whenever this is desired. Effects of this blockade include reduction of intra-ocular pressure, control of cardiac arrhythmias, and possibly a host of alpha-1C receptor mediated central nervous system events.

SUMMARY OF THE INVENTION

This invention provides compounds for the treatment of urinary obstruction caused by benign prostatic hypertropy (also known as benign prostatic hyperplasia or BPH). The compounds selectively antagonize the human alpha-1C adrenergic receptor at nanomolar and subnanomolar concetrations while exhibiting at least ten fold lower affinity for the alpha1A and alpha1B human adrenergic receptor and many other G-protein coupled receptors. This invention has the advantage over non-selective alpha-1 adrenoceptor antagonists of reduced side effects related to peripheral adrenergic blockade. Such side effects include orthostatic hypotension, syncope, lethargy etc. These compounds have the structure:

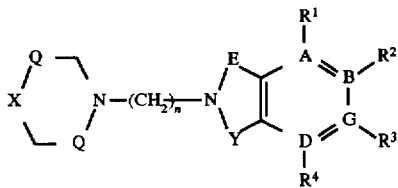

and a pharmaceutically acceptable salt, prodrug, polymorph, or metabolite thereof wherein:

n is an integer from 3 to 5;

Y represents carbonyl, sulphonyl, —CO—CH$_2$—, or —CO—NR$^{12}$—;

R$^{12}$ is hydrogen, substituted or unsubstituted lower alkyl, substituted or unsubstituted phenyl;

E is carbonyl or sulphonyl;

A, B, G, D are independently carbon or nitrogen;

R$^1$–R$^4$ are independently selected from the group consisting of hydrogen; halogen; nitro; amino; substituted or unsubstituted lower alkyl; perhalogenated lower alkyl; substituted or unsubstituted lower alkoxy; sulfonyl alkyl; and substituted or unsubstituted aryl or heteroaryl; with the proviso that if any of A, B, G, or D is a nitrogen, then the substituent R group is not present;

Q is, independently, (—CH$_2$—)$_r$, —NH—, S, or O;
r is 0-3; and
X is a)

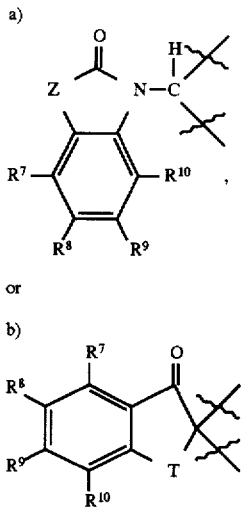

or b)

T is nitrogen, carbon, lower alkylene of one to three carbons or lower alkenylene of one to three carbons;

R$^7$–R$^{10}$ are independently selected from the group consisting of hydrogen, lower alkyl, lower alkenyl, and lower alkoxy; and Z is O, S, CH$_2$, CH$_2$O, OCH$_2$, SCH$_2$, lower alkylene, lower alkenylene, NH, or NMe.

In one embodiment of the invention, the compound has the structure:

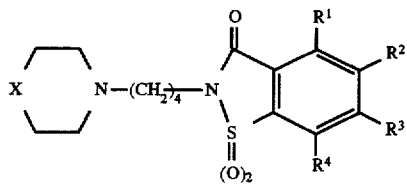

and a pharmaceutically acceptable salt, prodrug, polymorph or metabolite thereof, wherein all substituents are as defined above.

These compounds may be used to advantage whenever specific blockade of the alpha1C adrenergic receptor is desirable, and are particularly useful in the treatment of benign prostatic hyperplasia (BPH) and for inhibiting contraction of prostate tissue, either alone or in combination with other active compounds. One preferred combination therapy includes the use of compounds described herein in conduction with a compound effective to inhibit testosterone 5-alpha reductase.

BRIEF DESCRIPTION OF THE FIGURES

FIG. 1: Sequence of cDNA obtained by PCR of human heart mRNA, SEQ. ID:4:.

FIG. 2: Comparison of the open reading frame obtained from human heart, SEQ ID:5:, and the bovine alpha-1C adrenergic receptor sequence, SEQ. ID:6:.

FIG. 3: Sequence of cDNA obtained by screening a human hippocampus cDNA library using the heart mRNA derived sequence from FIG. 1, SEQ. ID:7:

FIG. 4: Sequence of 3' coding region of human alpha-1C gene, obtained by PCR amplification of a human genomic DNA library with oligonucleotides, SEQ. ID:10:.

FIG. 5: Sequence of the ligated portions of human alpha-1C DNA shown in FIGS. 3 and 4, SEQ. ID:11:.

FIG. 6: The amino acid sequence of the human alpha-1C adrenergic receptor, SEQ ID:12:.

FIG. 7: The alignment of the nucleotide and amino acid sequence of the human alpha-1C adrenergic receptor, showing the 5'-untranslated region, SEQ. ID:11: and SEQ. ID:12:.

FIG. 8: Expression of the human alpha-1C adrenergic receptor in COS cells: Binding data using membranes from cells transfected with the expression vector alone and the expression vector containing the human alpha-1C adrenergic receptor coding sequences.

FIG. 9: Binding curves of compounds using membranes from COS cells transfected with the human alpha-1C adrenergic receptor containing expression vector.

FIG. 10: Nucleotide sequence of the human alpha1A receptor, SEQ. ID:13:

FIG. 11: Amino acid sequence of the human alpha1A adrenergic receptor, SEQ. ID:14:

FIG. 12: Partial sequence of the human alpha1B adrenergic receptor, SEQ. ID:17:

FIG. 13: Partial sequence of the human alpha1B adrenergic receptor, SEQ. ID:20:

FIG. 14: Partial sequence of the human alpha1B adrenergic receptor, SEQ. ID:23:

FIG. 15: Composite human/rat alpha1B adrenoreceptror, SEQ. ID:24:

FIG. 16: Amino acid sequence of the composite human/rat alpha1B adrenergic receptor, SEQ. ID:25:

FIG. 17: Binding curves of compounds using membranes from COS cells transfected with the human alpha1A, 1B, and 1C adrenergic receptor expression vectors.

FIG. 18: Sequence of truncated human alpha1C adrenergic receptor, SEQ. ID:26:.

FIG. 19: Nucleotide sequence of the human $\alpha_{1C}$ adrenergic receptor having a Pst1 site, SEQ.ID:27:.

FIG. 20: Amino acid sequence of the human $\alpha_{1C}$ adrenergic receptor encoded by the Pst1 site encoding allele, SEQ.ID:28:.

FIG. 21: Alignment of the nucleotide and amino acid sequences of FIGS. 19 and 20, SEQ.ID:27: and SEQ.ID:28:.

FIG. 22: Nucleotide sequence of the human $\alpha_{1A}$ adrenergic receptor, Seq.ID:29:.

FIG. 23: Amino acid sequence of the human $\alpha_{1A}$ adrenergic receptor, SEQ.ID:30:.

FIG. 24: Alignment of the nucleotide and amino acid sequences of FIGS. 22 and 23, SEQ.ID:29: and SEQ.ID:30:.

DETAILED DESCRIPTION OF THE INVENTION

Compounds of this invention have the structure:

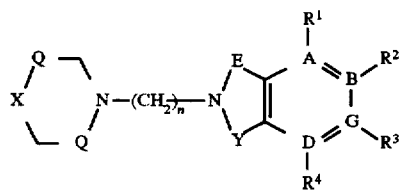

and a pharmaceutically acceptable salt, prodrug, polymorph, or metabolite thereof wherein:

n is an integer from 3 to 5;

Y represents carbonyl, sulphonyl, —CO—CH$_2$—, or —CO—NR$^{12}$—;

R$^{12}$ is hydrogen, substituted or unsubstituted lower alkyl, substituted or unsubstituted phenyl;

E is carbonyl or sulphonyl;

A, B, G, D are independently carbon or nitrogen;

R$^1$–R$^4$ are independently selected from the group consisting of hydrogen; halogen; nitro; amino; substituted or unsubstituted lower alkyl; perhalogenated lower alkyl; substituted or unsubstituted lower alkoxy; sulfonyl alkyl; and substituted or unsubstituted aryl or heteroaryl; with the proviso that if any of A, B, G, or D is a nitrogen, then the substituent R group is not present;

Q is, independently, (—CH$_2$—)$_r$, —NH—, S, or O;

r is 0–3; and

X is a)

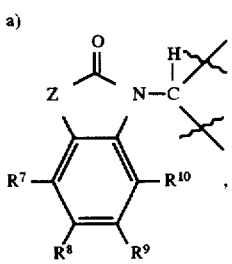

or b)

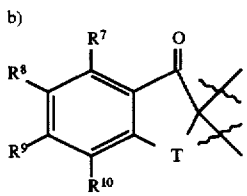

T is nitrogen, carbon, lower alkylene of one to three carbons or lower alkenylene of one to three carbons;

R$^7$–R$^{10}$ are independently selected from the group consisting of hydrogen, lower alkyl, lower alkenyl, and lower alkoxy; and Z is O, S, CH$_2$, CH$_2$O, OCH$_2$, SCH$_2$, lower alkylene, lower alkenylene, NH, or NMe.

In one embodiment of the invention, the compound has the structure:

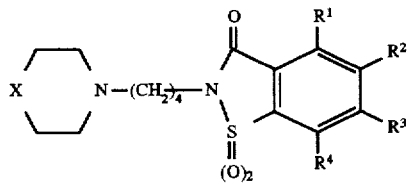

and a pharmaceutically acceptable salt, prodrug, polymorph or metabolite thereof, wherein all substituents are as defined above.

As used herein, the term lower alkyl, lower alkylene, or lower alkoxy means a substituted or unsubstituted, straight or branched chain of one to eight carbons. As used herein, a substituted group means that the group is halogenated, perhalogenated, particularly —CF$_3$, alkylated, alkoxylated, or is substituted with an aryl or heteroaryl. The term sulfonyl alkyl means a sulfonyl lower alkyl.

In a class of this embodiment of this invention, the compound is a piperidyl benzoxazinone substituted butyl saccharine or a spiroindanyl piperidine substituted butyl saccharine. In this embodiment of the invention, the compound is selected from:

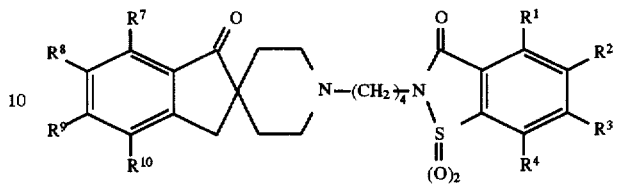

and wherein all variables are as previously defined. In specific embodiments of this invention, one of R$^1$–R$^4$ is preferably an electron withdrawing group such as the nitro group, a halogen or a halogenated alkyl which substituents we have discovered contribute to improved bioavailability.

Representative compounds of this invention exhibit high selectivity for the human alpha1C adrenergic receptor and are therefore useful for treating benign prostatic hyperplasia and for inhibiting contraction of prostate tissue. One implication of this selectivity for the human alpha1C adrenergic receptor is that these compounds display selectivity for lowering intraurethral pressure without substantially affecting diastolic blood pressure.

Representative compounds of this invention display sub-micromolar affinity for the human alpha1C adrenergic receptor subtype while displaying at least ten-fold lower affinity for the human alpha1A and alpha1B adrenergic receptor subtypes, and many other G-protein coupled human receptors. Particular representative compounds of this invention exhibit nanomolar and subnanomolar affinity for the human alpha1C adrenergic receptor subtype while displaying at least 30 fold lower affinity for the human alpha1A and alpha1B adrenergic receptor subtypes, and many other G-protein coupled human receptors. Representative compounds of this invention exhibit Ki's for human alpha1C adrenergic receptors over a 500 fold lower than for the human alpha1A or alpha1B adrenergic receptors, while exhibiting greater than 300 fold selectivity for the human alpha1C adrenergic receptor over all other human G-protein coupled receptors tested (including serotonin, dopamine, alpha 2 adrenergic, beta adrenergic or muscarinic receptors). Furthermore, representative compounds of this invention exhibit good bioavailability in known animal models (approximately 30% in dogs and 16% in rats). These indicia are expected to provide good indications of bioavailability in humans.

Compounds of this invention are prepared by a two step alkylation process beginning with a saccharine or substituted saccharine (referred to as "the saccharine moiety") prepared according to methods known in the art (see for example U.S. Pat. Nos. 4,818,756; 4,937,343; 4,988,809 and 5,187,276, hereby incorporated by reference for this purpose). Preparation of spiropiperidines used herein in the preparation of compounds of this invention is described, for example, in published European Patent Application 90313262.9 (publication number 0 431 943 A2, 6/12/91, herein incorporated by reference for this purpose). The saccharine moiety is alkylated with a reagent such as 1,4-dibromobutane, or a similar reagent, to form the butyl-saccharine moiety (see Scheme 1 below). The butyl saccharine is then alkylated with a piperidinyl benzoxazinone (prepared as shown in Scheme 2 below) or with a spiroindanyl piperidine (prepared as shown in Scheme 3 below) to form the active compounds of this invention (see Scheme 1 below). These steps are further defined with reference to the following schemes, and the synthetic examples appended hereto. It should be understood that the specific solvents, catalysts and reactants could be substituted by analogous reagents by those skilled in the art. All substituents are as defined above:

Scheme 1

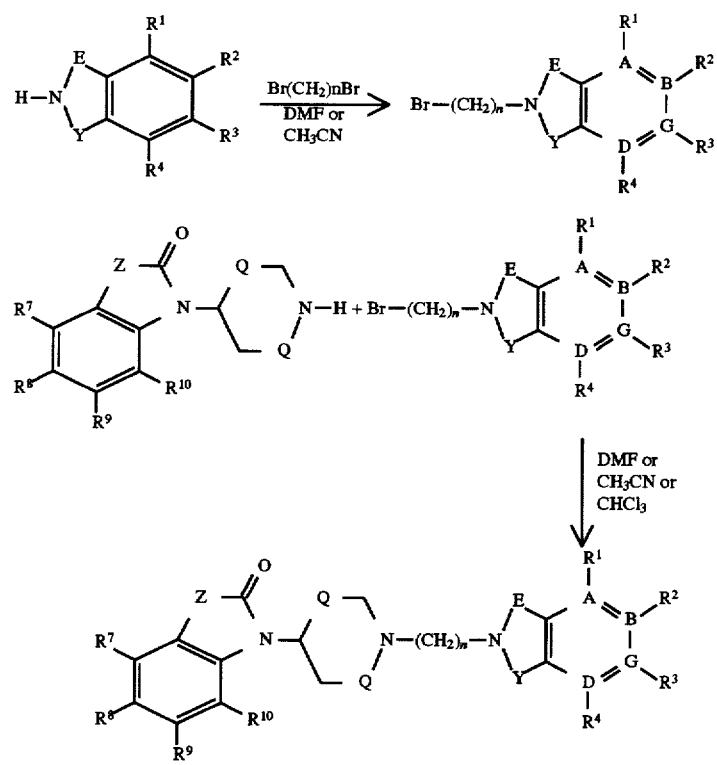

Scheme 2

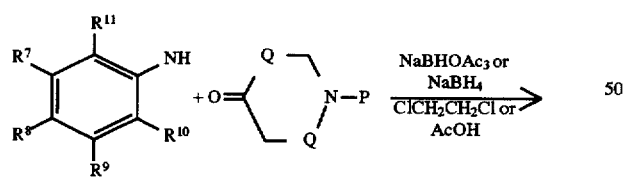

P = benzyl, benzyloxycarbonyl or tert-butoxycarbonyl
$R^{11}$ = $NO_2$, OH, SH, $CH_2OH$, H

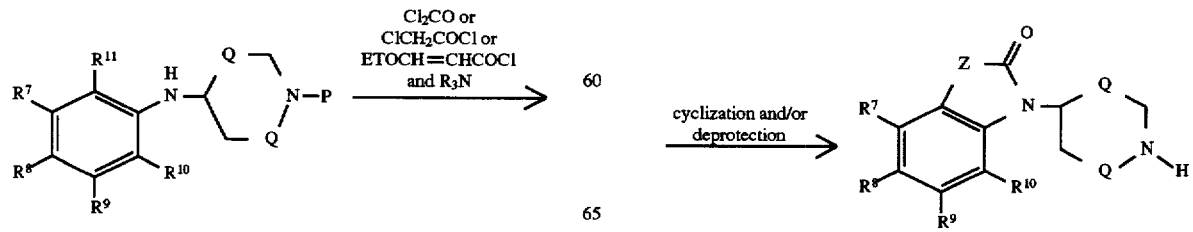

-continued
Scheme 2

Scheme 3

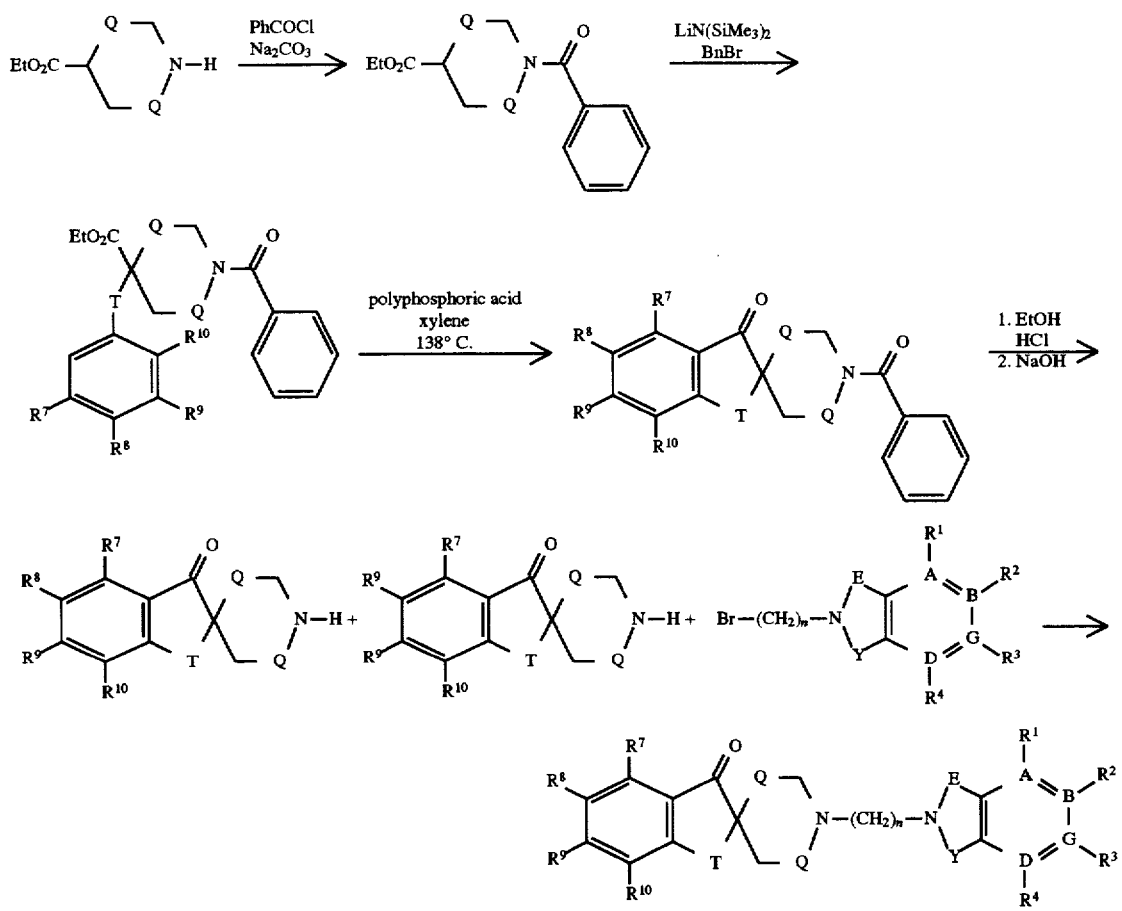

Abbreviations: DMF is dimethylformamide; EtOH is ethanol.

These compounds are administered in dosages effective to antagonize the alpha1C receptor where such treatment is needed, as in BPH and for inhibiting contraction of prostate tissue. For use in medicine, the salts of the compounds of this invention will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of this invention. In general, such prodrugs will be functional derivatives of the compounds of this invention which are readily convertible in vivo into the required compound. Conventional procedures for the selection and preparation of suitable prodrug derivatives are described, for example, in "Design of Prodrugs", ed. H. Bundgaard, Elsevier, 1985. Metabolites of these compounds include active species produced upon introduction of compounds of this invention into the biological mileu.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention. Furthermore, some of the crystalline forms for compounds of the present invention may exist as polymorphs and as such are intended to be included in the present invention. In addition, some of the compounds of the present invention may form solvates with water or common organic solvents. Such solvates are encompassed within the scope of this invention.

Specific compounds within the scope of the present invention include but are not limited to:

1,1-Dioxido-2-(4-(4-(2-oxo-3-benzoxazolinyl)-piperidin-1-yl)-butyl)-1,2-benzisothiazol-3(2H)-one;

1,1-Dioxido-2-(4-(4-(3,4-dihydro-2-oxo-(1H)-quinolin-1-yl)-piperidin-1-yl)-butyl)-1,2-benzisothiazol-3(2H)-one;

1,1-Dioxido-2-(4-(4-(2-oxo-3,1,4-benzoxazinyl)-piperidin-1-yl)-butyl)-1,2-benzisothiazol-3(2H)-one;

1,1-Dioxido-2-(4-(4-(2-oxo-(1H)-quinolin-1-yl)-piperidin-1-yl)-butyl)-1,2-benzisothiazol-3(2H)-one;

1,1-Dioxido-2-(4-(4-(2-oxo-(1H)-quinolin-1-yl)-piperidin-1-yl)-butyl)-5-nitro-1,2-benzisothiazol-3(2H)-one;

6-Chloro-1,1-dioxido-2-(4-(4-(2-oxo-(1H)-quinolin-1-yl)-piperidin-1-yl)-butyl)-1,2-benzisothiazol-3(2H)-one;

5-Chloro-1,1-dioxido-2-(4-(4-(2-oxo-(1H)-quinolin-1-yl)-piperidin-1-yl)-butyl)-1,2-benzisothiazol-3(2H)-one;

1,1-Dioxido-2-(4-(4-(2-oxo-(1H)-quinolin-1-yl)-piperidin-1-yl)-butyl)-7-nitro-1,2-benzisothiazol-3(2H)-one;

1,1-Dioxido-2-(4-(4-(2-oxo-(1H)-quinolin-1-yl)-piperidin-1-yl)-butyl)-4-methoxy-1,2-benzisothiazol-3(2H)-one;

1,1-Dioxido-2-(4-(4-(2-oxo-3-benzoxazolinyl)-piperidin-1-yl)-butyl)-5-nitro-1,2-benzisothiazol-3(2H)-one;

6-Chloro-1,1-dioxido-2-(4-(4-(2-oxo-3-benzoxazolinyl)-piperidin-1-yl)-butyl)-1,2-benzisothiazol-3(2H)-one;

5-Chloro-1,1-dioxido-2-(4-(4-(2-oxo-3-benzoxazolinyl)-piperidin-1-yl)-butyl)-1,2-benzisothiazol-3(2H)-one;

1,1-Dioxido-2-(4-(4-(2-oxo-3-benzoxazolinyl)-piperidin-1-yl)-butyl)-7-nitro-1,2-benzisothiazol-3(2H)-one;

1,1-Dioxido-2-(4-(4-(2-oxo-3-benzoxazolinyl)-piperidin-1-yl)-butyl)-4-methoxy-1,2-benzisothiazol-3(2H)-one;

1,1-Dioxido-2-(4-(4-(5-chloro-2-oxo-3-benzoxazolinyl)-piperidin-1-yl)-butyl)-1,2-benzisothiazol-3(2H)-one;

1,1-Dioxido-2-(4-(4-(3a-(R)-8a-(S)-2-oxo-3,3a,8,8a-tetrahydro-2H-indeno[1,2-d]oxazolinyl)-piperidin-1-yl)-butyl)-1,2-benzisothiazol-3(2H)-one;

1,1-Dioxido-2-(4-(4-(2-oxonaphth[2,3-d]oxazolinyl)-piperidin-1-yl)-butyl)-1,2-benzisothiazol-3(2H)-one;

1,1-Dioxido-2-(4-(4-(6-methyl-2-oxo-3-benzoxazolinyl)-piperidin-1-yl)-butyl)-1,2-benzisothiazol-3(2H)-one;

1,1-Dioxido-2-(4-(4-(2-oxo-5-phenyl-3-benzoxazolinyl)-piperidin-1-yl)-butyl)-1,2-benzisothiazol-3(2H)-one;

1,1-Dioxido-2-(4-(4-(6-methoxy-2-oxo-3-benzoxazolinyl)-piperidin-1-yl)-butyl)-1,2-benzisothiazol-3(2H)-one;

1,1-Dioxido-2-(4-(4-(6-carbomethoxy-2-oxo-3-benzoxazolinyl)-piperidin-1-yl)-butyl)-1,2-benzisothiazol-3(2H)-one;

1,1-Dioxido-2-(4-(4-(5-ethylsulfonyl-2-oxo-3-benzoxazolinyl)-piperidin-1-yl)-butyl)-1,2-benzisothiazol-3(2H)-one;

1,1-Dioxido-2-(4-(4-(2-oxo-3-oxazolo[4,5-b]pyridyl)-piperidin-1-yl)-butyl)-1,2-benzisothiazol-3(2H)-one;

1,1-Dioxido-2-(4-(4-(7-carbethoxy-2-oxo-3-benzoxazolinyl)-piperidin-1-yl)-butyl)-1,2-benzisothiazol-3(2H)-one;

1,1-Dioxido-2-(4-(4-(5-tert-butyl-2-oxo-3-benzoxazolinyl)-piperidin-1-yl)-butyl)-1,2-benzisothiazol-3(2H)-one;

1,1-Dioxido-2-(4-(4-(5,7-dimethyl-2-oxo-3-benzoxazolinyl)-piperidin-1-yl)-butyl)-1,2-benzisothiazol-3(2H)-one;

1,1-Dioxido-2-(4-(spiro(1,3-dihydro-1-oxo-2H-indene-2,4'-piperidin-1'-yl)butyl)-1,2-benzisothiazol-3(2H)-one;

1,1-Dioxido-2-(4-(4'-(3,4-dihydro-1-oxonaphthalene)-2(1H)-spiropiperidin-1'-yl)butyl)-1,2-benzisothiazol-3(2H)-one;

4-(3,4-Dihydro-6-methyl-spiro[2H-1-benzopyran-2,4'-piperidine-4(3H)-one]-1'-yl)-butylphthalimide;

4-(Spiro(piperidine-4,6'-[6H]thieno[2,3-b]thiopyran-4'(5'H)-one-1'-yl)-butylphthalimide;

4-(Spiro[benzothiazol-2(3H),4'-piperidin-1'-yl)-butylphthalimide;

4-(3,4-Dihydro-6-methoxy-spiro[2H-1-benzopyran-2,4'-piperidine-4(3H)-one]-1'-yl)-butylphthalimide;

4-(3,4-Dihydro-6-methanesulfonylamidyl-spiro[2H-1-benzopyran-2,4'-piperidine-4(3H)-one]-1'-yl)-butylphthalimide;

1,1-Dioxido-2-(4-(spiro[benzothiazol-2(3H),4'-piperidin-1'-yl)-butyl)-1,2-benzisothiazol-3(2H)-one;

4-(6-Trifluoromethyl-spiro[benzothiazol-2(3H),4'-piperidin-1'-yl)-butylphthalimide;

1,1-Dioxido-2-(4-(spiro[benzofuran-2(3H),4'-piperidin]-1'-yl)-butyl)-1,2-benzisothiazol-3(2H)-one;

4-(Spiro[benzofuran-2(3H),4'-piperidin]-1'-yl)-butylphthalimide;

4-(Spiro[2H-1,3-benzoxazine-2,4'-piperidin]-1'-yl)-butylphthalimide;

3,3-Dioxido-1,2-dehydro-2-(4-(spiro[2H-indene-2,4'-piperidine-1(3H)-one]-1'-yl)-butyl)-naphth[1,2-d]isothiazol-1-one;

1,1-Dioxido-2-(4-(spiro[2H-indene-2,4'-piperidine-1(3H)-one]-1'-yl)-butyl)-4-methoxy-1,2-benzisothiazol-3(2H)-one;

1,1-Dioxido-2-(4-(spiro[2H-indene-2,4'-piperidine-1(3H)-one]-1'-yl)-butyl)-7-methoxy-1,2-benzisothiazol-3(2H)-one;

1,1-Dioxido-2-(4-(spiro(1,3-dihydro-1-oxo-2H-indene-2,4'-piperidin-1'-yl)butyl)-5-methoxy-1,2-benzisothiazol-3(2H)-one;

1,1-Dioxido-2-(4-(spiro(1,3-dihydro-1-oxo-2H-indene-2,4'-piperidin-1'-yl)butyl)-6-methoxy-1,2-benzisothiazol-3(2H)-one;

1,1-Dioxido-2-(4-(spiro(1,3-dihydro-1-oxo-2H-indene-2,4'-piperidin-1'-yl)butyl)-5-methyl-1,2-benzisothiazol-3(2H)-one;

1,1-Dioxido-2-(4-(spiro(1,3-dihydro-1-oxo-2H-indene-2,4'-piperidin-1'-yl)butyl)-5-chloro-1,2-benzisothiazol-3(2H)-one;

1,1-Dioxido-2-(4-(spiro(1,3-dihydro-1-oxo-2H-indene-2,4'-piperidin-1'-yl)butyl)-5-fluoro-1,2-benzisothiazol-3(2H)-one;

1,1-Dioxido-2-(4-(spiro(1,3-dihydro-1-oxo-2H-indene-2,4'-piperidin-1'-yl)butyl)-5-nitro-1,2-benzisothiazol-3(2H)-one;

1,1-Dioxido-2-(4-(spiro(1,3-dihydro-1-oxo-2H-indene-2,4'-piperidin-1'-yl)butyl)-6-nitro-1,2-benzisothiazol-3(2H)-one;

1,1-Dioxido-2-(4-(spiro(1,3-dihydro-1-oxo-2H-indene-2,4'-piperidin-1'-yl)butyl)-isothiazolo[5,4-c]pyridin-3(2H)-one;

1,1-Dioxido-2-(4-(spiro(1,3-dihydro-1-oxo-2H-indene-2,4'-piperidin-1'-yl)butyl)-isothiazolo[5,4-b]pyridin-3(2H)-one;

1,1-Dioxido-2-(4-(4-(6-methyl-2-oxo-3-benzoxazolinyl)-piperidin-1-yl)-butyl)-5-nitro-1,2-benzisothiazol-3(2H)-one;

2-(4-(Spiro(1,3-dihydro-1-oxo-2H-indene-2,4'-piperidin-1'-yl)butyl)-pyrrolo[3,4b]pyridin-5,7(1H)-dione;

1,1-Dioxido-2,3-dihydro-2-(4-(spiro[2H-indene-2,4'-piperidine-1(3H)-one]-1'-yl)-butyl)-naphth[1,8-de]isothiazin-3-one; and 1,1-Dioxido-2-(4-(spiro[3-oxo-phthalan-1,4'-piperidin-1'-yl)butyl)-1,2-benzisothiazol-3(2H)-one;

1,1-Dioxido-2-(4-(4-(1,3-dihydro-2-oxo-2H-benzimidazolin-1-yl)-piperidin-1-yl)-butyl)-1,2-benzisothiazol-3(2H)-one;

1,1-Dioxido-2-(4-(4-(1,3-dihydro-2-oxo-3-methyl-2H-benzimidazolin-1-yl)-piperidin-1-yl)-butyl)-1,2-benzisothiazol-3(2H)-one;

1,1-Dioxido-2-(4-(4-(1,3-dihydro-2-oxo-5-methyl-2H-benzimidazolin-1-yl)-piperidin-1-yl)-butyl)-1,2-benzisothiazol-3(2H)-one;

1,1-Dioxido-2-(4-(4-(1,3-dihydro-2-oxo-4-methyl-2H-benzimidazolin-1-yl)-piperidin-1-yl)-butyl)-1,2-benzisothiazol-3(2H)-one;

1,1-Dioxido-2-(4-(4-(1,3-dihydro-2-oxo-5-methoxy-2H-benzimidazolin-1-yl)-piperidin-1-yl)-butyl)-1,2-benzisothiazol-3(2H)-one;

1,1-Dioxido-2-(4-(4-(1,3-dihydro-2-oxo-5-chloro-2H-benzimidazolin-1-yl)-piperidin-1-yl)-butyl)-1,2-benzisothiazol-3(2H)-one;

1,1-Dioxido-2-(4-(4-(1,3-dihydro-2-oxo-5-fluoro-2H-benzimidazolin-1-yl)-piperidin-1-yl)-butyl)-5-chloro-1,2-benzisothiazol-3(2H)-one;

1,1-Dioxido-2-(4-(4-(1,3-dihydro-2-oxo-5-methyl-2H-benzimidazolin-1-yl)-piperidin-1-yl)-butyl)-5-chloro-1,2-benzisothiazol-3(2H)-one;

1,1-Dioxido-2-(4-(4-(1,3-dihydro-2-oxo-6-methyl-2H-benzimidazolin-1-yl)-piperidin-1-yl)-butyl)-5-chloro-1,2-benzisothiazol-3(2H)-one;

1,1-Dioxido-2-(4-(4-(5-methyl-2-oxo-3-benzoxazolinyl)-piperidin-1-yl)-butyl)-5,6-dihydro-[1,4]dioxino[2,3-e]benzisothiazol-3(2H)-one;

1,1-Dioxido-2-(4-(4-(2-oxo-3-benzoxazolinyl)-piperidin-1-yl)-butyl)-5,6-dihydro-[1,4]dioxino[2,3-e]benzisothiazol-3(2H)-one;

1,1-Dioxido-2-(4-(4-(spiro-1,3-dihydro-1-oxo-2H-indenyl)-2,4'-piperidin-1'-yl)-butyl)-5,6-dihydro-[1,4]dioxino[2,3-e]benzisothiazol-3(2H)-one;

1,1-Dioxido-2-(4-(4-(1,3-dihydro-2-oxo-1H-3,4-dihydroquinazolin-1-yl)-piperidin-1-yl)-butyl)-1,2-benzisothiazol-3(2H)-one;

2-(4-Hydroxybutyl)-1,1-dioxido-5,6-dihydro-[1,4]dioxino[2,3-d]benzisothiazol-3(2H)-one;

1,1-Dioxido-2-(4-(4-(2-oxo-3-benzoxazolinyl)-piperidin-1-yl)-butyl)-5-ethoxy-1,2-benzothiazol-3(2H)-one;

1,1-Dioxido-2-(4-(4-(spiro-1,3-dihydro-1-oxo-2H-indenyl)-2,4'-piperidin-1'-yl)-butyl)-5-ethoxy-1,2-benzothiazol-3(2H)-one;

1,1-Dioxido-2-(4-(4-(spiro-1,3-dihydro-1-oxo-2H-indenyl)-2,4'-piperidin-1'-yl)-butyl)-5-ethyl-1,2-benzothiazol-3(2H)-one;

1,1-Dioxido-2-(4-(4-(2-oxo-3-benzoxazolinyl)-piperidin-1-yl)-butyl)-5-ethyl-1,2-benzothiazol-3(2H)-one;

1,1-Dioxido-2-(4-(4-(spiro-1,3-dihydro-1-oxo-2H-indenyl)-2,4'-piperidin-1'-yl)-butyl)-5-(2-propyl)-1,2-benzothiazol-3(2H)-one;

1,1-Dioxido-2-(4-(4-(2-oxo-3-benzoxazolinyl)-piperidin-1-yl)-butyl)-5-(2-propyl)-1,2-benzothiazol-3(2H)-one;

1,1-Dioxido-2-(4-(4-(2-oxo-3-benzoxazolinyl)-piperidin-1-yl)-butyl)-6-nitro-1,2-benzisothiazol-3(2H)-one;

1,1-Dioxido-2-(4-(4-(2-oxo-3-benzoxazolinyl)-piperidin-1-yl)-butyl)-5-fluoro-1,2-benzisothiazol-3(2H)-one;

1,1-Dioxido-2-(4-(4-(2-oxo-3-benzoxazolinyl)-piperidin-1-yl)-butyl)-5-methyl-1,2-benzisothiazol-3(2H)-one;

1,1-Dioxido-2-(4-(4-(2-oxo-3-benzoxazolinyl)-piperidin-1-yl)-butyl)-5-bromo-1,2-benzisothiazol-3(2H)-one;

1,1-Dioxido-2-(4-(4-(2-oxo-3-benzoxazolinyl)-piperidin-1-yl)-butyl)-5-trifluoromethyl-1,2-benzisothiazol-3(2H)-one;

1,1-Dioxido-2-(4-(4-(2-oxo-3-benzoxazolinyl)-piperidin-1-yl)-butyl)-5-trifluoromethoxy-1,2-benzisothiazol-3(2H)-one;

1,1-Dioxido-2-(4-(4-(2-oxo-1-naphth[1,2-d]oxazolinyl)-piperidin-1-yl)-butyl)-1,2-benzisothiazol-3(2H)-one;

1,1-Dioxido-2-(4-(4-(5,6,7,8-tetrahydro-2-oxo-3-naphth[2,3-d]oxazolinyl)-piperidin-1-yl)-butyl)-1,2-benzisothiazol-3(2H)-one;

1,1-Dioxido-2-(4-(4-(5-methyl-2-oxo-3-benzoxazolinyl)-piperidin-1-yl)-butyl)-1,2-benzisothiazol-3(2H)-one;

1,1-Dioxido-2-(4-(4-(5-carbomethoxy-2-oxo-3-benzoxazolinyl)-piperidin-1-yl)-butyl)-1,2-benzisothiazol-3(2H)-one;

1,1-Dioxido-2-(4-(4-(6-fluoro-2-oxo-3-benzoxazolin-1-yl)-butyl)-1,2-benzisothiazol-3(2H)-one;

1,1-Dioxido-2-(4-(4-(4-methyl-2-oxo-3-benzoxazolinyl)-piperidin-1-yl)-butyl)-1,2-benzisothiazol-3(2H)-one;

1,1-Dioxido-2-(4-(4-(4-methoxy-2-oxo-3-benzoxazolinyl)-piperidin-1-yl)-butyl)-1,2-benzisothiazol-3(2H)-one;

5-Chloro-1,1-dioxido-2-(4-(4-(6-methyl-2-oxo-3-benzoxazolinyl)-piperidin-1-yl)-butyl)-1,2-benzisothiazol-3(2H)-one;

5-Methylthio-1,1-dioxido-2-(4-(4-(6-methyl-2-oxo-3-benzoxazolinyl)-piperidin-1-yl)-butyl)-1,2-benzisothiazol-3(2H)-one;

5-Ethoxy-1,1-dioxido-2-(4-(4-(6-methyl-2-oxo-3-benzoxazolinyl)-piperidin-1-yl)-butyl)-1,2-benzisothiazol-3(2H)-one;

5-Chloro-1,1-dioxido-2-(4-(4-(6-fluoro-2-oxo-3-benzoxazolinyl)-piperidin-1-yl)-butyl)-1,2-benzisothiazol-3(2H)-one;

4-Methyl-1,1-dioxido-2-(4-(4-(2-oxo-3-benzoxazolinyl)-piperidin-1-yl)-butyl)-1,2-benzisothiazol-3(2H)-one;

4-Chloro-1,1-dioxido-2-(4-(4-(2-oxo-3-benzoxazolinyl)-piperidin-1-yl)-butyl)-1,2-benzisothiazol-3(2H)-one;

4-Ethoxy-1,1-dioxido-2-(4-(4-(2-oxo-3-benzoxazolinyl)-piperidin-1-yl)-butyl)-1,2-benzisothiazol-3(2H)-one;

4-(2-Propyloxy)-1,1-dioxido-2-(4-(4-(2-oxo-3-benzoxazolinyl)-piperidin-1-yl)-butyl)-1,2-benzisothiazol-3(2H)-one;

5-Methoxy-1,1-dioxido-2-(4-(4-(6-methyl-2-oxo-3-benzoxazolinyl)-piperidin-1-yl)-butyl)-1,2-benzisothiazol-3(2H)-one;

1,1-Dioxido-2-(4-(4-(2-oxo-3-benzoxazolinyl)-piperidin-1-yl)-butyl)-6-methylsulfonyl-1,2-benzisothiazol-3(2H)-one;

5-Methoxy-1,1-dioxido-2-(4-(4-(2-oxo-3-benzoxazolinyl)-piperidin-1-yl)-butyl)-1,2-benzisothiazol-3(2H)-one;

1,1-Dioxido-2-(4-(4-(2-oxo-3-benzoxazolinyl)-piperidin-1-yl)-butyl)-5-methylsulfonyl-1,2-benzisothiazol-3(2H)-one;

5-Methylthio-1,1-dioxido-2-(4-(4-(2-oxo-3-benzoxazolinyl)-piperidin-1-yl)-butyl)-1,2-benzisothiazol-3(2H)-one;

5-Methylsulfonyl-1,1-dioxido-2-(4-(4-(6-methyl-2-oxo-3-benzoxazolinyl)-piperidin-1-yl)-butyl)-1,2-benzisothiazol-3(2H)-one; or 1,1-Dioxido-2-(4-(4-(2-oxo-1-oxazolo[5,4-b]pyridyl)-piperidin-1-yl)-butyl)-1,2-benzisothiazol-3(2H)-one;

and pharmaceutically acceptable salts, metabolites and prodrugs thereof.

Preferred compounds of the present invention include:

1,1-Dioxido-2-(4-(4-(1,3-dihydro-2-oxo-2H-benzimidazolin-1-yl)-piperidin-1-yl)-butyl)-1,2-benzisothiazol-3(2H)-one;

1,1-Dioxido-2-(4-(4-(1,3-dihydro-2-oxo-3-methyl-2H-benzimidazolin-1-yl)-piperidin-1-yl)-butyl)-1,2-benzisothiazol-3(2H)-one;

1,1-Dioxido-2-(4-(4-(1,3-dihydro-2-oxo-5-methyl-2H-benzimidazolin-1-yl)-piperidin-1-yl)-butyl)-1,2-benzisothiazol-3(2H)-one;

1,1-Dioxido-2-(4-(4-(1,3-dihydro-2-oxo-5-chloro-2H-benzimidazolin-1-yl)-piperidin-1-yl)-butyl)-1,2-benzisothiazol-3(2H)-one;

1,1-Dioxido-2-(4-(4-(1,3-dihydro-2-oxo-5-fluoro-2H-benzimidazolin-1-yl)-piperidin-1-yl)-butyl)-5-chloro-1,2-benzisothiazol-3(2H)-one;

1,1-Dioxido-2-(4-(4-(1,3-dihydro-2-oxo-5-methyl-2H-benzimidazolin-1-yl)-piperidin-1-yl)-butyl)-5-chloro-1,2-benzisothiazol-3(2H)-one;

1,1-Dioxido-2-(4-(4-(1,3-dihydro-2-oxo-6-methyl-2H-benzimidazolin-1-yl)-piperidin-1-yl)-butyl)-5-chloro-1,2-benzisothiazol-3(2H)-one; and 1,1-Dioxido-2-(4-(4-(5-methyl-2-oxo-3-benzoxazolinyl)-piperidin-1-yl)-butyl)-5,6-dihydro-[1,4]dioxino[2,3-e]benzisothiazol-3(2H)-one;

and pharmaceutically acceptable salts, metabolites and pro-drugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of BPH, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The specificty of binding of compounds showing affinity for the α1C receptor is shown by comparing affinity to membranes obtained from COS cells tranfected with the cloned α1C receptor and membranes from tissues known to express other types of alpha or beta adrenergic receptors. In addition, the cloned human α1A and a hybrid human/rat α1B (with only the cytoplasmic, carboxy terminal region being rat sequence) could be used for this purpose, along with the human α1C receptor expressed in COS cells. Expression of the cloned human α1A, α1B, and α1C receptors and comparison of their binding properties with known selective antagonists provides a rational way for selection of compounds and discovery of new compounds with predictable pharmacological activities. Antagonism by these compounds of the human alpha1C adrenergic receptor subtype may be functionally demonstrated in anesthetized animals. These compounds may be used to increase urine flow without exhibiting orthostatic hypotensive effects.

The human alpha adrenergic receptor of the 1-C subtype was identified, cloned and expressed. A partial coding region for this receptor was generated by reverse transcriptase-polymerase chain reaction technology, RT-PCR. Accordingly, degenerate oligonucleotides encoding amino acids conserved in the fifth and sixth transmembrane domains of all three al receptor subtypes (A, B, C) were used to prime RT-PCR reactions using human heart mRNA as template. The predicted sized products were cloned and sequenced. Translation of the amplified cDNA yielded an open reading frame encoding a protein 95% homologous to the bovine α1C receptor (FIG. 2, SEQ. ID:5: and SEQ. ID:6:). This partial sequence was used to obtain a larger cDNA clone from a human hippocampus library (FIG. 3, SEQ. ID:6:). The remaining coding region was obtained by PCR amplification of human genomic DNA using primers based on the cDNA sequence and the last six amino acids of bovine α1C receptor (FIG. 4, SEQ.ID:10:). The complete receptor was then assembled using the partial sequences shown in FIG. 3, SEQ.ID:6: and FIG. 4, SEQ. ID:10:, to generate the sequence shown in FIG. 5, SEQ. ID:11:. The translation of this sequence is shown in FIG. 6, SEQ. ID:12:, and the alignment of the nucleotide and amino acid sequences, and the 5′-untranslated sequences, is shown in FIG. 7, SEQ. ID:11: and SEQ. ID:12:.

The 3'-terminal six amino acids of the human $\alpha_{1C}$ adrenergic receptor were confirmed by screening a human genomic library with the radiolabeled 3'-terminal 512 nucleotides of the SEQ. ID:10: clone previously obtained. A complete human exon 2 was generated in this manner and sequenced. The nucleotide sequence of this gene is provided in FIG. 19, SEQ. ID:27: and the amino acid sequence is provided in FIG. 20, SEQ. ID:28:. We discovered that this clone was identical to the original 3'-terminal portion of the gene, except that:

1) There are five silent nucleotide changes between the new clone and the previously obtained clone (the last five codons, including the stop codon, each have a silent change in the third nucleotide); and
2) At nucleotide position 1636 (amino acid 347), there is a cytosine to thymine base change resulting in the formation of a Pst1 site at that location and a concomitant single amino acid change of Arg to Cys. Thus, we have confirmed and localized the site of the two-allele Pst1restriction fragment polymorphism (RFLP) noted by Hoehe et al., [*Human Mol. Genetics*, 1(5):349 (8/92)]. Through pharmacological studies using clones of both alleles, we have confirmed that the Arg to Cys change appear to be pharmacologically indistinguishable (see Table II, Example 11, below).

The cloned human $\alpha 1C$ receptor, when expressed in mammalian cell lines (see FIG. 8), is used to discover ligands that bind to the receptor and alter its function. In addition, the cloned $\alpha 1C$ receptor enables quanititation of mRNA levels in human tissues, including the aorta and prostate, by RNase protection assays. For these purposes, a complete coding sequence of the receptor is provided. However, as long as the ligand binding and signal transduction segments of the receptor (G-protein interaction) are intact, truncation at the 3' end of the sequence does not affect the functioning of the receptor. Thus, in addition to the sequence provided in SEQ. ID:11:, a sequence, truncated at the 3' end, SEQ. ID:26: is disclosed, which consists entirely of human alpha1C sequence.

Once the human receptor is cloned and expressed in a cell such as COS cells or CHO cells, the receptor is free of other human proteins. The membranes from cells expressing different human alpha adrenergic receptor subtypes are then isolated according to methods well known in the art for membrane associated receptor binding assays.

For example, the method of Schwinn, et al., (*J. Biol. Chem.*, 265:8183–8189, 1990) may be used. A compound of interest is used to compete with the binding of a known, quantifiable alpha receptor ligand. Thus, radiolabled prazosin, niguldipine, 5-methyl urapidil, terazosin, dozazosin, phenoxybenzamine, WB4101, benoxathian, HEAT (2-[β-(4-hydroxy-3-iodophenyl)ethylaminomethyl] tetralone, or phentolamine may be used for this purpose (see, for example, Robert R. Ruffolo, Jr., α-*Adrenoreceptors: Molecular Biology, Biochemistry and Pharmacology*, (*Progress in Basic and Clinical Pharmacology* series, Karger, 1991), page 29). Because of the ease of $^{125}$Iodine detection, $^{125}$I-HEAT may be preferred for this purpose. By increasing the amount of unlabeled, test compound, the labeled compound is competed off the receptor. From these experiments, IC50 values for each test compound and receptor subtype is determined.

A new sequence for the human α1A adrenergic receptor which is more homologous to the rat α1A adrenergic receptor sequence is also provided herein (see Example 12 and FIGS. 22, 23, and 24, SEQ. ID:29: and SEQ. ID:30:). While no difference in ligand binding has thus far been observed based on the different amino terminal amino acid sequences between these two receptors, such differences cannot be ruled out except by screening compounds against both clones. Since a new human α1A adrenergic receptor sequence is provided herein, compounds identified using the earlier reported human α1A adrenergic receptor sequence can now be confirmed against this clone.

Compounds of this invention exhibiting selective human α1C adrenergic receptor antagonism may further be defined by counterscreening. This is accomplished according to methods known in the art using other receptors responsible for mediating diverse biological functions. Compounds which are both selective amongst the various human alpha1 adrenergic receptor subtypes and which have low affinity for other receptors, such as the alpha2 adrenergic receptors, the β-adrenergic receptors, the muscarinic receptors, the serotonin receptors, and others are particularly preferred. The absence of these non-specific activities may be confirmed by using cloned and expressed receptors in an analogous fashion to the method disclosed herein for identifying compounds which have high affinity for the various huaman alpha1 adrenergic receptors. Furthermore, functional biological tests are used to confirm the effects of identified compounds as alpha1C adrenergic receptor antagonists.

Compounds of this patent disclosure may be used alone at appropriate dosages defined by routine testing in order to obtain optimal antagonism of the human α1C adrenergic receptor while minimizing any potential toxicity. In addition, co-administration or sequential administration of other agents which alleviate the effects of BPH is desirable. Thus, in one embodiment, this includes administration of compounds of this invention and a human testosterone 5-α reductase inhibitor. Included in this embodiment are inhibitors of 5-alpha reductase isoenzyme 2. Many such compounds are now well known in the art and include such compounds as PROSCAR®, (also known as finasteride, a 4-Aza-steroid; see U.S. Pat. Nos. 4,377,584 and 4,760,071, for example, hereby incorporated by reference). In addition to PROSCAR®, which is principally active in prostatic tissue due to its selectivity for human 5-α reductase isozyme 2, combinations of compounds which are specifically active in inhibiting testosterone 5-alpha reductase isozyme 1 (found particularly in skin) and compounds which act as dual inhibitors of both isozymes 1 and 2, are useful in combination with compounds of this invention. Compounds that are active as 5α-reductase inhibitors have been described in WO93/23420, EP 0572166; WO 93/23050; WO93/23038,; WO93/23048; WO93/23041; WO93/23040; WO93/23039; WO93/23376; WO93/23419, EP 0572165; WO93/23051, each of which is hereby incorporated by reference.

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human alpha1C adrenergic receptors can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an alpha1C antagonistic agent.

The daily dosage of the products may be varied over a wide range from 0.01 to 1,000 mg per adult human/per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0002 mg./kg to about 50 mg./kg. of body weight per day. The range is more particularly from about 0.001 mg./kg to 7 mg./kg. of body weight per day. With reference to terazosin, it is predictable that the potent and more selective compounds of this invention are effective at doses equal to or between ten and a hundred fold lower than dosages utilized for that compound (see, for example, U.S. Pat. No. 5,212,176). The dosages of the alpha1C adrenergic receptor and testosterone 5-alpha reductase inhibitors are adjusted when combined to achieve desired effects. As those skilled in the art will appreciate, less 5-alpha reductase inhibitor may be required when the acute symptoms of BPH are alleviated by treatment with the alpha1C adrenergic receptor inhibitor of this invention. On the other hand, dosages of these various agents may be independently optimized and combined to achieve a synergistic result wherein the pathology is reduced more than it would be if either agent were used alone.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated. The term inhibitorily effective amount or antagonistically effective amount as used herein means that amount of an active compound which, when contacted with a particular enzyme or receptor, interrupts the usual catalytic activity or signal transduction of that enzyme or receptor.

The term "subject," as used herein refers to an animal, preferably a mammal, most preferably a human, who has been the object of treatment, observation or experiment.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For the treatment of benign prostatic hyperplasia, prostatitis and the prevention and/or treatment of prostatic cancer, compounds of this invention exhibiting alpha1C adrenergic receptor blockade can be combined with a therapeutically effective amount of a 5α-reductase 2 inhibitor, such as finasteride, in addition to a 5α-reductase 1 inhibitor, such as 4,7B-dimethyl-4-aza-5α-cholestan-3-one, in a single oral, systemic, or parenteral pharmaceutical dosage 5 formulation. Alternatively, a combined therapy can be employed wherein the alpha1C adrenergic receptor antagonist and the 5α-reductase 1 or 2 inhibitor are administered in separate oral, systemic, or parenteral dosage formulations. See, e.g., U.S. Pat. Nos. 4,377,584 and 4,760,071 which describe dosages and formulations for 5α-reductase inhibitors.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like.

Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Compounds of this invention may be administered in any of the foregoing compositions and according to dosage regimens established in the art whenever specific blockade of the human alpha1C adrenergic receptor is required.

The following examples are provided to further define the invention without, however, limiting the invention to the particulars of these examples.

EXAMPLE 1

PCR amplification cloning and sequencing of phα1X:

Based on the amino acid homologies of human α1A, rat α1B and bovine α1C receptors, degenerate oligonucleotides were designed to amplify cDNAs encoding all three receptor subtypes. These oligonucleotides are:

WL' (SEQ. ID:1) TTTTCTAGAT TRTTARRTA NCCNAGCC 28

MYC (SEQ. ID:2) TTTACTAGTA TCSTNGTNAT GTAYTG 16

WC' (SEQ. ID:3) TTTTCTAGAG AARAANGGNA RCCARC 26

Oligonucleotides MYC and WL' were used as primers in a reverse transcription PCR amplification of human heart mRNA (Clontech) using the RNA PCR kit from Perkin Elmer Cetus. Briefly, 0.5 ug of mRNA was reverse transcribed in a volume of 20 ul using either random oligonucleotide primers (reaction 1) or oligo dT primer (reaction 2). Reactions 1 and 2 were pooled and served as template for PCR amplification as follows:

PCR Reactions:

Primary reaction (50 ul)

5 ul 10× buffer from Perkin Elmer Cetus GeneAmp Kit 8 ul 1.25 mM each stock of dATP,dCTP,dGTP, and dTTP 3 ul first strand cDNA 1 ul 25 pMoles oligo MYC 1 ul 25 pMoles oligo WL'

0.25 ul 1.25 units Amplitaq DNA polymersase 31.75 ul water

Reaction conditions; 40 cycles of 94° C. 1'; 45° C. 2'; 72° C. 2'

Secondary reaction (100 ul)

9.5 ul 10× buffer from Perkin Elmer Cetus GeneAmp Kit 16 ul 1.25 mM each stock of dATP,dCTP,dGTP, and dTTP 5 ul first strand cDNA 2 ul 50 pMoles oligo MYC 2 ul 50 pMoles oligo WC'

0.5 ul 2.5 units Amplitaq DNA polymersase 65 ul water

Reaction conditions; 40 cycles of 94° C. 1'; 45° C. 2'; 72° C. 2'

Prep scale tertiary reaction 3×200 ul:

19.5 ul 10× buffer 32 ul 1.25 mM each stock of dATP, dCTP, dGTP, and dTTP 5 ul secondary PCR reaction 4 ul 100 pMoles oligo MYC 4 ul 100 pMoles oligo WC'

1 ul 5 units Amplitaq DNA polymerase 134.5 ul water

Reaction conditions; 30 cycles of 94° C. 1'; 50° C. 2'; 72° C. 2'

The PCR product was purified by Qiagen spin columns and digested with restriction endonucleases SpeI and XbaI. The fragment was then ligated into SpeI/XbaI cut pGEM9Zf (−). The ligation mix was used to transform E. coli XL-1 blue. Plasmid DNA was isolated from white transformants and sequenced by the dideoxy chain termination method. The base sequence obtained is shown in FIG. 1, SEQ. ID:4:.

EXAMPLE 2

Isolation of partial alpha1C cDNA Clone:

A cDNA library prepared from mRNA isolated from human hippocampus (Stratagene) was screened by plaque hybridization using phαX as a probe. Hybridization conditions were as follows:

5×SSC (1×SSC is 0.15M sodium chloride, 0.015M sodium citrate,

50% Formamide

5× Denhardt's Solution (1% Ficoll, 1% polyvinylpyrrolidone, 1% bovine serum albumin)

0.15 mg/ml salmon sperm DNA hybridize overnight at 42° C.

Filters were washed 3 times in 2×SSC, 0.1% SDS at room temperature for 5', then 1 time in 1×SSC, 0.1% SDS at 50C for 30'. Positive clones were identified by autoradiography. Phagemid DNA was rescued from the positive plaques and sequenced by the dideoxy chain termination method. The base sequence obtained is shown in FIG. 3, SEQ. ID:7:.

EXAMPLE 3

PCR amplification cloning and sequencing of 3'CG of alpha1C:

The 3' end of the coding region of human alpha1C adrenergic receptor was amplified from human genomic DNA using two oligonucleotides:

S3C (SEQ ID:8:)

5' TTTGAATTCT GATTTCAAGC CCTCTG 3' and

3° C. (SEQ ID:9:)

5' TTTGAATTCT TANACYTCYT CNCCRTTYTC 3' as follows:

10 ul 10× buffer from Perkin Elmer Cetus GeneAmp Kit 16 ul 1.25 mM each stock of dATP,dCTP,dGTP, and dTTP 6 ul 1 ug human genomic DNA (Promega)

2 ul 50 pMoles oligo S3C 2 ul 50 pMoles oligo 3'C 0.5 ul 2.5 units Amplitaq DNA polymersase 63.5 ul water Reaction conditions; 40 cycles of 94° C. 1'; 50° C. 2'; 72° C. 2'

The PCR product was purified by Qiagen spin columns and digested with restriction endonuclease EcoRI. The fragment was then ligated into EcoRI cut pGEM3Zf(−). The ligation mix was used to transform E. coli XL-1 blue. Plasmid DNA was isolated from white transformants and sequenced by the dideoxy chain termination method. The base sequence is shown in FIG. 4, SEQ. ID:10:.

EXAMPLE 4
Assembly of complete coding region of human alpha1c adrenergic receptor:

The complete coding region of human alpha1c adrenergic receptor was assembled by ligating the cDNA clone (see Example 2, FIG. 3, SEQ ID:7:) and 3'CG (see Example 3, FIG. 4, SEQ ID:10:) at their common PvuII site (1552–1557 of FIG. 3, SEQ ID:7: and 59–64 of FIG. 4, SEQ ID:10:). The complete nucleotide sequence is shown in FIG. 5, SEQ ID:11:. The amino acid sequence is shown in FIG. 6, SEQ ID:12:. FIG. 7 shows the structure of the cDNA, including the 5'-untranslated sequences. The very 3' twenty seven nucleotides (6 amino acids) shown is the sequence of the PCR primer used to generate the sequence. However, the function of the receptor, both for ligand binding and signal transduction depends on sequences far removed from the carboxy terminus of the receptor. A completely human sequence is shown in FIG. 18, SEQ. ID:26: which is truncated at the 3' terimuns.

EXAMPLE 5
Expression of the cloned alpha1C adrenergic receptor:

The complete sequence (SEQ ID:11:) of the human alpha1C adrenergic receptor was subcloned into the eukaryotic expression vector pcDNAI-neo (Invitrogen). The resulting plasmid was transfected into COS-7 cells by electroporation. Cells were harvested after 72 hours and the membranes containing the expressed receptor protein were prepared as described in Schwinn, et al., *J. Biol. Chem.*, 265:8183–8189, 1990. Membranes (5–25 ug, see FIG. 8) prepared from the COS-7 cells transfected with the vector containing the alpha1C receptor gene specifically bound the alpha 1 antagonist [$^{125}$I]-HEAT; membranes prepared from the COS-7 cells transfected with the vector alone did not bind the alpha 1 antagonist [$^{125}$I]-HEAT (FIG. 8), proving the expression of the alpha1C adrenergic receptor. Binding reactions (total volume=200 ul) contained 50 mM Tris-HCl pH. 7.4, 5 mM EDTA, 150 mM NaCl, 100 pM [$^{125}$I]-HEAT, and membranes prepared from COS-7 cells transfected with expression plasmids. Reactions were incubated at room temperature for one hour with shaking. Reactions were filtered onto Whatman GF/C glass fiber filters with a Brandel cell harvester. Filters were washed three times with ice cold buffer and bound radioactivity was determined. Non specific binding was determined in the presence of 10 uM prazosin.

EXAMPLE 6
Screening assay: Alpha 1 C Adrenergic Receptor Binding

Membranes prepared from the transfected COS-7 cells may also be used to identify compounds that bind to the human alpha1C adrenergic receptor. These competition binding reactions (total volume=200 ul) contain 50 mM Tris-HCl pH. 7.4, 5 mM EDTA, 150 mM NaCl, 100 pM [$^{125}$I]-HEAT, membranes prepared from COS-7 cells transfected with the alpha1C expression plasmid and increasing amounts of unlabeled ligand. Reactions are incubated at room temperature for one hour with shaking. Reactions were filtered onto Whatman GF/C glass fiber filters with a Brandel cell harvester. Filters were washed three times with ice cold buffer and bound radioactivity was determined. Binding data were analyzed and IC50s determined by an iterative curve fitting program. Results are shown in FIG. 9.

EXAMPLE 7
Expression of human alpha1A adrenergic receptor:

The complete coding region for the human alpha1A adrenergic receptor (Bruno, et al., BBRC., 179:1485–1490, (1991); see FIG. 10, SEQ. ID:13: and FIG. 11, SEQ. ID:14: herein) was subcloned into the eukaryotic expression vector pcDNAI-neo (Invitrogen). The resulting plasmid was transfected into COS-7 cells by electroporation. Cells were harvested after 72 hours and the membranes containing the expressed receptor protein were prepared as described in Schwinn, et al., *J. Biol. Chem.*, 265:8183–8189, 1990. Membranes prepared from the COS-7 cells transfected with the vector containing the alpha1A receptor gene specifically bound the alpha1 antagonist [$^{125}$I]-HEAT; membranes prepared from the COS-7 cells transfected with the vector alone did not bind the alpha1 antagonist [$^{125}$I]-HEAT.

Binding reactions (total volume=200 ul) contained 50 mM Tris-HCl pH. 7.4, 5 mM EDTA, 150 mM NaCl, 100 pM [$^{125}$I]-HEAT, and membranes prepared from COS-7 cells transfected with expression plasmids. Reactions are incubated at room temperature for one hour with shaking. Reactions were filtered onto Whatman GF/C glass fiber filters with a Brandel cell harvester. Filters were washed three times with ice cold buffer and bound radioactivity was determined. Non-specific binding was determined in the presence of 10 uM prazosin.

EXAMPLE 8
Expression of human alpha1 B adrenergic receptor:

1. PCR amplification of partial cDNA for human alpha1 B adrenergic receptor:

Amplification of 5XB clones

5XB, SEQ. ID:15: 5' TCT AGA CCA TGA AYC CNG AYC TGG 3'

A1B, SEQ. ID:16: 5' TTT GAA TTC ACA TWC CGA CYA CAA TGC CC 3'

Oligonucleotides 5XB and A1B were used as primers in a reverse transcription PCR amplification of human heart mRNA (Clontech) using the Invitrogen Copy Kit. Briefly, 1.0 ug of mRNA was reverse transcribed in a volume of 20 ul using oligonuleotide WC' as primer.

Primary reaction (50 ul)

5 ul 10× buffer from Perkin Elmer Cetus GeneAmp Kit 8 ul 1.25 mM each stock of dATP,dCTP,dGTP, and dTTP 2.5 ul first strand cDNA 1 ul 25 pMoles oligo 5XB 1 ul 25 pMoles oligo A1B 0.25 ul 1.25 units Amplitaq DNA polymersase 32.75 ul water Reaction conditions; 40 cycles of 94° C. 1'; 58° C. 2'; 72° C. 2'

The PCR product was directly ligated into pCR vector (Invitrogen) and used to transform *E. coli* INVαF' (Invitrogen). Plasmid DNA was isolated from white transfonnants and sequenced by the dideoxy chain termination method. The base sequence is shown in FIG. 12, SEQ. ID:17:

2. Amplification of EFK clones

EFK, SEQ. ID:18: 5' GAAGGCGCGCTTGAACTC 3'

5B1, SEQ. ID:19: 5' AGAGAACCACCAAGAACC 3'

Oligonucleotides EFK and 5B1 were used as primers in a reverse transcription PCR amplification of human aorta mRNA (Clontech) using the Invitrogen Copy Kit. Briefly, 1.0 ug of mRNA was reverse transcribed in a volume of 20 ul using oligo dT as primer.

Primary reaction (50 ul)

5 ul 10× buffer from Perkin Elmer Cetus GeneAmp Kit 8 ul 1.25 mM each stock of dATP,dCTP,dGTP, and dTTP 2.0 ul first strand cDNA 1 ul 25 pMoles oligo EFK 1 ul 25 pMoles oligo 5B1

0.25 ul 1.25 units Amplitaq DNA polymersase 33.25 ul water

Reaction conditions; 40 cycles of 94° C. 1'; 58° C. 2'; 72° C. 2'

The PCR product was directly ligated into pCR vector (Invitrogen) and used to transform E. coli INVaF' (Invitrogen). Plasmid DNA was isolated from white transformants and sequenced by the dideoxy chain termination method. The base sequence is shown in FIG. 13, SEQ. ID:20:.

3. Assembly of partial cDNA for human alpha1B adrenergic receptor

A partial cDNA clone encoding the human alpha1B adrenergic receptor was assembled by joining the 5XB sequence (SEQ. ID:17:) and the EFK sequence (SEQ. ID:20:) at their common BamHI site.

4. Amplification of the 3' end of rat alpha1B adrenergic receptor

S4B, SEQ. ID:21: 5' TTT GAA TTC ATG TTC AAG GTG GTG TTC 3'

3'B2, SEQ. ID:22: 5' TTT GAA TTC TAA AASTGN CCN GGN SCC AGN GGC AT 3'

Oligonucleotides S4B and 3'B2 were used as primers in a reverse transcription PCR amplification of rat heart mRNA using the Invitrogen Copy Kit. Briefly, 0.6 ug of mRNA was reverse transcribed in a volume of 20 ul using oligo dT as primer.

Primary reaction (50 ul)

5 ul 10× buffer from Perkin Elmer Cetus GeneAmp Kit 8 ul 1.25 mM each stock of dATP,dCTP,dGTP, and dTTP 2.0 ul first strand cDNA 1 ul 25 pMoles oligo EFK 1 ul 25 pMoles oligo 5B1

0.25 ul 1.25 units Amplitaq DNA polymersase 33.25 ul water

Reaction conditions; 40 cycles of 94° C. 1'; 58° C. 2'; 72° C. 2'

The PCR product was directly ligated into pCR vector (Invitrogen) and used to transform E. coli INVαF' (Invitrogen). Plasmid DNA was isolated from white transformants and sequenced by the dideoxy chain termination method. The base sequence is shown in FIG. 14, SEQ. ID:23:.

5. Assembly and expression of a functional human/rat hybrid alpha1B adrenergic receptor The partial human alpha1B adrenergic receptor cDNA was joined to the 3' end of the rat alpha1B adrenergic receptor cDNA at their common BssHII restriction endonuclease site. This composite sequence is shown in FIG. 15, SEQ. ID:24:, and the amino acid sequence is shown in FIG. 16, SEQ. ID:25:

The complete coding region for the human/rat alpha1B adrenergic receptor was subcloned into the eukaryotic expression vector pcDNAI-neo (Invitrogen). The resulting plasmid was transfected into COS-7 cells by electroporation. Cells were harvested after 72 hours and the membranes containing the expressed receptor protein were prepared as described in Schwinn, et al., J. Biol. Chem., 265:8183–8189, 1990. Membranes prepared from the COS-7 cells transfected with the vector containing the alpha1B receptor gene specifically bound the alpha1 antagonist [$^{125}$I]-HEAT; membranes prepared from the COS-7 cells transfected with the vector alone did not bind the alpha1 antagonist [$^{125}$I]-HEAT. Binding reactions (total volume=200 ul) contained 50 mM Tris-HCl pH. 7.4, 5 mM EDTA, 150 mM NaCl, 100 pM [$^{125}$I]-HEAT, and membranes prepared from COS-7 cells transfected with expression plasmids. Reactions are incubated at room temperature for one hour with shaking. Reactions were filtered onto Whatman GF/C glass fiber filters with a Brandel cell harvester. Filters were washed three times with ice cold buffer and bound radioactivity was determined. Non specific binding was determined in the presence of 10 uM prazosin.

EXAMPLE 9

Selective Binding assays

Membranes prepared from COS-7 cells transfected with the human alpha1 receptor subtype expression vectors may also be used to identify compounds that selectively bind to the human alpha1C adrenergic receptor. These competition binding reactions (total volume=200 ul) contain 50 mM Tris-HCl pH. 7.4, 5 mM EDTA, 150 mM NaCl, 100 pM [$^{125}$I]-HEAT, membranes prepared from COS-7 cells transfected with the respective alpha 1 subtype expression plasmid and increasing amounts of unlabeled ligand. Reactions are incubated at room temperature for one hour with shaking. Reactions were filtered onto Whatman GF/C glass fiber filters with a Brandel cell harvester. Filters were washed three times with ice cold buffer and bound radioactivity was determined. Binding data were analyzed and IC50s determined by an iterative curve fitting program. Table I shows the results from such an analysis.

| Compound | IC$_{50}$ (nM) | | |
|---|---|---|---|
| | α1A | α1B | α1C |
| prazosin | 0.6 | 2.4 | 1 |
| terazosin | 4 | 5 | 19 |
| doxazosin | 5 | 2 | 9 |
| phenoxybenzamine | 6.1 | 4.3 | 4.0 |
| WB4101 | 1 | 16 | 1 |
| benoxathian | 2.5 | 68 | 1.5 |
| phentolamine | 36 | 650 | 14 |
| 5-methyl urapidil | 42 | 270 | 3.5 |
| S(+) niguldipine | 130 | 670 | 1.4 |

EXAMPLE 10

Identification and Cloning of a new Allele for the Human Alpha 1-C Adrenergic Receptor Probes:

3'CG: A 525 bps fragment, specific to complete exon.2 of human alpha1c AR, was PCR amplified from human genomic DNA using a sense primer based on the isolated cDNA clone and an antisense primer based on the last six amino acids of bovine alpha1c cDNA. This PCR product was subcloned and confirmed by sequencing (see Example 3, SEQ.ID:10:).

Genomic Library Screening:

Human W138 Fibroblast genomic library synthesized in the Lambda Fix II vector (2×10$^6$ recombinants; Stratagene, La Jolla, Calif.) was screened with (3'CG). This probe was labelled with $^{32}$P-dCTP (Amersham) by random-primed labelling kit (Boehringer Mannheim,Indianapolis,Ind.). A Total 800,000 plaques were screened, using duplicate Hybond-N nylone filters (Amersham,UK). Prior to hybridization, filters were denatured (1.5M NaCl+0.5M NaOH), neutralized (1.5M NaCl+1M Tris.Cl,pH 8.0) and washed (0.2M Tris.Cl pH 7.5+2 SSC), 5' for each. DNA was cross-linked with UV cross-linker (Stratagene,La Jolla, Calif.). The filters were, then, hybridized in 50% formamide, 5×SSC(1×SSC=0.15M NaCl, 0.015M Na citrate, pH7.0), 0.02% polyvinylpyrophosphate, 0.2% Ficoll, 0.2% bovine serum albumin, 150 μg of sheared & boiled Salmon sperm DNA, $10^6$ cpm of $^{32}$P-labelled probe at 42° C. for 40 hrs. Filters were washed in 0.1×SSC+1% SDS solution at 60° C. for 20'. Two more rounds of screening for 20 "positive" plaques/clones with 3'CG probe confirmed two clones for the alpha1C adrenergic receptor, which were named 48.1C and 53.1C. Clone 53.1C was subjected to further analysis/investigation.

Sub-clonning of Exon.2:

53.1C lambda DNA was amplified by plate lysis method and purified with Qiagen midi-lambda kit (Qiagen, Chatsworth,Calif.). A 2.6 Kb band excised with EcoRI restriction enzyme was identified by Southern analysis using 3'CG probe. This fragment was then subcloned into pGEM3Zf(+) vector.

DNA sequencing:

Nucleotide sequence analysis of DNA in both direction was performed by Sanger chain termination method.

Result and Discussion:

Sequencing analysis of this genomic clone confirmed that clone 53.1c contains sequences for complete exon.2 flanked by an intron at 5'-end. It also revels that there is a nucleotide change from cytosine (C) to thymine(T) at nucleotide position 1636, amino acid position 347. This change creates a PstI site and changes the codon for arginine (Arg) to cystine (Cys). This data differs from the known/published cDNA sequence of the gene. Southern analysis of human genomic DNA confirms the PstI site in the gene/exon.2.

EXAMPLE 11

Comparative Pharmacology of Alpha 1-C Alleles

We have cloned two genes for the human alpha-1c receptor. The coding regions differ by a single nucleotide. The genes encode either Cys or Arg at amino acid 347 near the C terminus of the receptor. The nucleotide difference lies within a PstI restriction enzyme recognition site thus creating a Restriction Fragment Length Polymorphism (RFLP). The frequency of allele 1 (LRR) is 0.34; allele 2 (LCR) is 0.66 in 83 unrelated individuals (Hoehe et al "A two-allele PstI RFLP for the alpha-1C adrenergic receptor gene" Human Molecular Genetics 1: 349, 1992; Allele I is defined by a 2.1 kb PstI fragment; allele 2 yields two bands of 1.6 and 0.5 kb). Since the amino acid difference occurs within the intracellular tail of the receptor we would not expect any pharmacological differences between the expressed receptors. To investigate the pharmacological profiles of the two allelic forms of the human alpha-1c adrenergic receptor we ligated the genomic exon 2 fragment of allele 2 to a cDNA clone of allele 1 at a common PvuII restriction site. The two allelic forms were transiently expressed in COS-7 cells using pcDNAI/NEO (Invitrogen) expression vector. Competitive inhibition studies performed in the presence of $^{125}$I-HEAT with various antagonists showed no significant difference in their pharmacological profiles (Table II):

TABLE II

| COMPARATIVE PHARMACOLOGY OF ALPHA1-C ALLELES | | |
|---|---|---|
| | IC$_{50}$ (nM) | |
| | LRR | LCR |
| phentolamine | 15 | 17 |
| niguldipine | 0.8 | 1.8 |
| prazosin | 1.0 | 0.9 |

TABLE II-continued

| COMPARATIVE PHARMACOLOGY OF ALPHA1-C ALLELES | | |
|---|---|---|
| | IC$_{50}$ (nM) | |
| | LRR | LCR |
| 5-methyl urapidi | 3.1 | 4.3 |
| WB4101 | 0.9 | 1.0 |

EXAMPLE 12

Cloning of a Novel Alpha1-A Adrenergic Receptor

A cosmid library containing FG293 cell line genomic DNA in the double-cos vector sCos-1 was screened as follows: The published human $\alpha_1$a receptor cDNA clone (Bruno et al., *BBRC*, 179:1485–1490 (1991), and see FIG. 10, SEQ.ID:13:) was cloned into the vector pcDNA1 neo to generate the clone pEXα1a. Filters containing approximately 200,000 clones were screened by colony hybridization ([Sambrook, *Molecular Cloning*, Cold Spring Harbor Laboratory Press, New York, 1989]) using a mixed exon 1 probe generated by PCR corresponding to $\alpha_{1a}$(TMD1-3), $\alpha_{1b}$ (TMD1-5) and $\alpha_{1c}$ (TMD1-5): 25 cycles of 95° C. 1'; 52° C. 30 sec; 72° C. 1.5' using 10 ng of pEX α1b, pEX α1c or pEX α1a and 10 pmoles each of primers 5' MET (5' GAATCCCGACCTGGAC), SEQ.ID:31:, and 3' BAM (5'GGATCCTCAGGGTC), SEQ.ID:32:, for α1b, 5' 597 (5' CCATGGTGTTTCTCTCGGG), SEQ.ID:33: and 3' 1219 (5' GACGCGGCAGTACATGAC), SEQ.ID:34: for α1c or 5' 76 (5' GTCATGATGGCTGGGTACTTG), SEQ.ID:35:, for α1a in a 12 μl reaction containing 1.5 μM each unlabelled dNTP and 50 μCi 3000 Ci/mmol α-[$^{32}$P] dCTP. The filters were incubated with 1×10$^6$ cpm/ml of probe in 5× SSC, 35% Formamide, 0.02% SDS, 0.1% lauroyl sarcosine, 2% blocking buffer (Bohrenger Mannheim), at 42° C. for 18 hours. The filters were washed with 2 liters of 0.5× SSC, 0.1% SDS, 55° C. and exposed to Kodak XAR-5 film. Twelve primary positives were picked from master plates and re-screened using the $\alpha_{1a}$-specific probe. Cosmid DNA was prepared from second round positive clones, digested with endonucleases Eco RI or Hind III and subjected to Southern blot analysis: Fragments were resolved by electrophoresis, and transferred to a nitrocellulose membrane (Bohrenger Mannheim) with 20× SSC (1× SSC= 0.15M Sodium chloride, 0.015M Sodium citrate, pH 7.0) according to the method of Southern ([Southern, 1975 #14]) . The membrane was hybridized, washed and analyzed as described above. Alpha-1a, $\alpha_{1b}$, and $\alpha_{1c}$ receptor clones were identified by comparison of restriction patterns with genomic southern blots performed with $\alpha_{1a}$, $\alpha_{1b}$, or $\alpha_{1c}$ specific probes. A Cosmid containing $\alpha_{1a}$ receptor exon 1 DNA was subjected to restriction digestion by endonuclease Pst I and subjected to southern blot analysis as above using the $\alpha_{1a}$-specific probe. Two fragments of 2.3 and 1.6 kb were detected and subcloned into the Pst I site of PGEM 3ZF. The presence of the correct 5' terminal sequences in the 2.3 kb fragment was confirmed by sequencing across the junction between inverted repeat and non-repeat sequences. The 5' end of the $\alpha_{1a}$ receptor gene was ligated to the cDNA clone at their common PstI site, see FIGS. 22–24, SEQ.ID:29:, and SEQ.ID:30:.

EXAMPLE 13

Exemplary Counterscreens

1. Assay Title: Dopamine D2,D4 in vitro screen
   Objective of the Assay:

The objective of this assay is to eliminate agents which specifically affect binding of [³H] spiperone to cells expressing human dopamine receptors D2, D3 or D4.

Method:

Modified from VanTol et al (1991); Nature (Vol 350) Pg 610–613.

Frozen pellets containing specific dopamine receptor subtypes stably expressed in clonal cell lines are lysed in 2 ml lysing buffer (10 mM Tris-HCl/5 mM Mg, pH 7.4). Pellets obtained after centrifuging these membranes (15' at 24,450 rpm) are resuspended in 50 mM Tris-HCl pH 7.4 containing EDTA, MgCl[2], KCl, NaCl, CaCl[2] and ascorbate to give a 1 Mg/mL suspension. The assay is initiated by adding 50–75 µg membranes in a total volume of 500 µl containing 0.2 nM [³H]-spiperone. Non-specific binding is defined using 10 µM apomorphine. The assay is terminated after a 2 hour incubation at room temperature by rapid filtration over GF/B filters presoaked in 0.3% PEI, using 50 mM Tris-HCl pH 7.4.

2. Assay Title: Serotonin 5HT1a

Objective of the Assay

The objective of this assay is to eliminate agents which specifically affect binding to cloned human 5HT1a receptor Method:

Modified from Schelegel and Peroutka Biochemical Pharmacology 35: 1943–1949 (1986).

Mammalian cells expressing cloned human 5HT1a receptors are lysed in ice-cold 5 mM Tris-HCl, 2 mM EDTA (pH 7.4) and homogenized with a polytron homogenizer. The homogenate is centrifuged at 1000×g for 30', and then the supernatant is centrifuged again at 38,000×g for 30'. The binding assay contains 0.25 nM [³H]8-OH-DPAT in 50 mM Tris-HCl, 4 mM CaCl2 and 1 mg/ml ascorbate. Non-specific binding is defined using 10 µM propranolol. The assay is terminated after a 1 hour incubation at room temperature by rapid filtration over GF/Cfilters.

EXAMPLE 14

Exemplary Functional Assays

In order to confirm the specificity of compounds for the human alpha1C adrenergic receptor and to define the biological activity of the compounds, the following functional tests may be performed:

1. In vitro Rat, Dog and Human Prostate and Dog Urethra

Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 6–8 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.

The tissue is placed in a Petri dish containing oxygenated Krebs solution [NaCl, 118 mM; KCl, 4.7 mM; CaCl$_2$, 2.5 mM; KH$_2$PO$_4$, 1.2 mM; MgSO$_4$, 1.2 mM; NaHCO$_3$, 2.0 mM; dextrose, 11 mM] warmed to 37° C. Excess lipid material and connective tissue are carefully removed. Tissue segments are attached to glass tissue holders with 4-0 surgical silk and placed in a 5 ml jacketed tissue bath containing Krebs buffer at 37° C., bubbled with 5% CO$_2$/95% O$_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.

After a single priming dose of 3 µM (for rat), 10 µM (for dog) and 20 µM (for human) of phenylephrine, a cumulative concentration response curve to an agonist is generated; the tissues are washed every 10 minutes for one hour. Vehicle or antagonist is added to the bath and allowed to incubate for one hour, then another cumulative concentration response curve to the agonist is generated.

EC$_{50}$ values are calculated for each group using GraphPad Inplot software. pA$_2$ ($-$log K$_b$) values were obtained from Schild plot when three or more concentrations were tested. When less than three concentrations of antagonist are tested, Kb values are calculated according to the following formula $$K_b = \frac{[B]}{x-1},$$

where x is the ratio of EC$_{50}$ of agonist in the presence and absence of antagonist and [B] is the antagonist concentration.

2. Measurement of Intra-Urethral Pressure in Anesthetized Dogs

PURPOSE: Benign prostatic hyperplasia causes decreased urine flow rate that may be produced by both passive physical obstruction of the prostatic urethra from increased prostate mass as well as active obstruction due to prostatic contraction. Alpha adrenergic receptor antagonists such as prazosin and terazosin prevent active prostatic contraction, thus improve urine flow rate and provide symptomatic relief in man. However, these are non-selective alpha-1 receptor antagonists which also have pronounced vascular effects. Because we have identified the alpha-1C receptor subtype as the predominent subtype in the human prostate, it is now possible to specifically target this receptor to inhibit prostatic contraction without concomitant changes in the vasculature. The following model is used to measure adrenergically mediated changes in intra-urethral pressure and arterial pressure in anesthetized dogs in order to evaluate the efficacy and potency of selective alpha adrenergic receptor antagonists. The goals are to: 1) identify the alpha-1 receptor subtypes responsible for prostatic/urethral contraction and vascular responses, and 2) use this model to evaluate novel selective alpha adrenergic antagonists. Novel and standard alpha adrenergic antagonists may be evaluated in this manner.

METHODS: Male mongrel dogs (7–12 kg) are used in this study. The dogs are anesthetized with pentobarbital sodium (35 mg/kg, i.v. plus 4 mg/kg/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cannulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the prostate and noting the large change in urethral pressure.

Phenylephrine, an alpha-1 adrenergic agonist, is administered (0.1–100 ug/kg, iv; 0.05 ml/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLFIT software package) with a four paramenter logistic equation constraining the slope, minimum response, and maximum response to be constant among curves. The dose ratios for the antagonist doses (rightward shift in the dose-response curves from control) are calculated as the ratio of the $ED_{50}$'s for the respective curves. These dose-ratios are then used to construct a Schild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephrine responses for intra-urethral and arterial pressure. The relative selectivity is calculated as the ratio of arterial pressure and intra-urethral pressure Kb's. Effects of the alpha-1 antagonists on baseline arterial pressure are also monitored. Comparison of the relative antagonist potency on changes in arterial pressure and intra-urethral pressure provide insight as to whether the alpha receptor subtype responsible for increasing intra-urethral pressure is also present in the systemic vasculature. According to this method, one is able to confirm the selectivity of alpha1C adrenergic receptor antagonists that prevent the increase in intra-urethral pressure to phenylephrine without any activity at the vasculature.

At the end of the experiment, the dogs are killed via an overdose of intravenously administered pentobarbital or saturated KCl.

EXAMPLE 15

1,1-Dioxido-2-(4-(4-(2-oxo-3-benzoxazolinyl)-piperidin-1-yl)-butyl)-1,2-benzisothiazol-3(2H)-one Step 1: A mixture of 15.4 g 4-piperidone hydrochloride hydrate, 200 mL ether, 100 mL saturated aqueous Na2CO3 solution and 21.8 g di-t-butyldicarbonate was vigorously stirred for 48 h. The layers were separated and the organic layer was washed with two 150 mL portions of 10% aqueous citric acid, dried over $MgSO_4$. Removal of solvents under reduced pressure gave 18.9 g (95%) N-t-butyloxycarbonyl-4-piperidone as a white solid.

Step 2: A mixture of 6.0 g N-t-butyloxycarbonyl-4-piperidone, 3.3 g of 2-aminophenol, 25 mL of 1,2-dichloroethane, 25 mL of glacial acetic acid, and 500 mg powdered 4 Å molecular sieves was stirred under inert atmosphere. After 30 min, 6.4 g sodium triacetoxyborohydride was added stirring was continued for 38 h. The reaction mixture was poured into 400 mL ethyl acetate and 200 mL saturated aqueous $NaHCO_3$ and the layers separated. The organic layer was washed with brine (2×100 mL), dried over $MgSO_4$, filtered and concentrated under reduced pressure. Chromatography of the crude product on silica gel, eluting with a gradient of 1–3% methanol/methylene chloride containing 0.5% concentrated $NH_4OH$ gave 6.95 g (79%) 1-t-butyloxycarbonyl-4-(2-hydroxyphenylamino) piperidine as an orange foam.

Step 3: To a stirred solution of 6.95 g 1-t-butyloxycarbonyl-4-(2-hydroxyphenylamino)piperidine and 6.2 mL diisopropylethylamine in 120 mL tetrahydrofuran cooled to 0° C. was added 3.0 g triphosgene. The reaction was stirred 30 min at 0° C. and then at room temperature 2 h. The precipitate was removed by filtration, the filtrate concentrated at reduced pressure and partitioned between 250 mL ethyl acetate and 100 mL saturated aqueous $Na_2CO_3$. The layers were separated, the organic layer washed with 100 mL of saturated aqueous $Na_2CO_3$, 100 mL of water, 100 mL of brine, dried over $MgSO_4$, and concentrated under reduced pressure. Chromatography of the crude product on silica gel, eluting with a gradient of 40–50% ethyl acetate-hexanes gave 6.0 g (79%) 1-((1-t-butyloxycarbonyl)piperidin-4-yl)-3-benzoxazolin-2-one as a yellow foam.

Step 4: A stirred solution of 6.0 g (19 mmol) 1-((1-t-butyloxycarbonyl)piperidin-4-yl)-3-benzoxazolin-2-one in 120 mL ethyl acetate was cooled to −78° C. and a stream of hydrogen chloride gas was introduced with a fritted dispersion tube for 15 min. The mixture was allowed to warm to 0° C. for 1 h, then room temperature for 2 h. The resulting precipitate was collected by filtration. Drying at reduced pressure for 8 h gave 4.2 g (16.5 mmol, 88%) of the hydrochloride salt of 1-(4-piperidinyl)-3-benzoxazolin-2-one as an off-white solid.

Step 5: A mixture of 430 mg (1.7 mmol) of the hydrochloride salt of 5 1-(4-piperidinyl)-3-benzoxazolin-2-one and 588 mg (1.9 mmol) of 2-(4-bromobutyl)-1,1-dioxido-1,2-benzothiazol-3(2H)-one, 20 mL dry dimethylformamide and 0.6 mL (3.5 mmol) diisopropylethylamine was warmed to 80° C. for 3 h. The solvents were removed under reduced pressure and the crude oily product dissolved in 100 mL ethyl acetate, washed with saturated aqueous $NaHCO_3$ (3×30 mL), brine (1×30 mL), dried over $Na_2SO_4$ and concentrated at reduced pressure. Chromatography of the crude product on silica gel, eluting with a gradient of 10% methanol in methylene chloride and recrystallization from ethyl acetate gave 300 mg (40%) of 1,1-dioxido-2-(4-(4-(2-oxo-3-benzoxazolinyl)-piperidin-1-yl)-butyl)-1,2-benzisothiazol-3(2H)-one as an off-white crystalline solid. Analysis calculated for $C_{23}H_{25}N_3O_5S$ C: 60.64, H: 5.53, N: 9.22 found C: 60.04, H: 5.50, N: 9.29. $^1$H NMR (300 MHz, $CDCl_3$) 8.07 (dd, J=6.54, 2.2 Hz, 1H), 7.93 (m, 1H), 7.85 (m, 2H), 7.18 (m, 4H), 4.21 (tt, J=12.4, 4.34 Hz, 1H), 3.85 (t, J=7.27 Hz, 2H), 3.07 (d, J=11.67 Hz, 2H), 2.45 (t, J=7.57 Hz, 2H), 2.35 (dt, J=12.45, 3.71 Hz, 2H), 2.11 (dt, J=12.1, 1.84 Hz, 2H), 1.90 (m, 4H), 1.64 (m, 2H).

EXAMPLE 16

1,1-Dioxido-2-(4-(4-(3,4-dihydro-2-oxo-(1H)-quinolin-1-yl)-piperidin-1-yl)-butyl)-1,2-benzisothiazol-3(2H)-one From the hydrochloride salt of 3,4-dihydro-1-(4-piperidyl)-2(1H)-quinolinone prepared according to H. Ogawa et. al. *J. Med. Chem.* 1993, 36, 2011–2017, and 2-(4-bromobutyl)-1,1-dioxido-1,2-benzothiazol-3(2H)-one using the procedure described for Example 15, Step 5 there was obtained 1,1-dioxido-2-(4-(4-(3,4-dihydro-2-oxo-(1H)-quinolin-1-yl)-piperidin-1-yl)-butyl)-1,2-benzisothiazol-3 (2H)-one as a white solid: $^1$H NMR (300 MHz, $CDCl_3$) 8.07

(dd, J=6.5, 2.3 Hz, 1H), 7.92 (t, J=6.73 Hz, 1H), 7.84 (m, 2H), 7.21 (t, J=8.73 Hz, 2H), 7.19 (m, 1H), 6.99 (t, J=7.13 Hz, 1H), 4.35 (tt, J=12.2, 4.2 Hz, 1H), 3.83 (t, J=7.32 Hz, 2H), 3.04 (d, J=11.42 Hz, 2H), 2.81 (t, J=6.59 Hz, 2H), 2.61 (m, 3H), 2.43 (t, J=7.19 Hz, 2H), 2.09 (t, J=11.71 Hz, 2H), 1.88 (m, 2H), 1.69 (m, 5H).

EXAMPLE 17

1,1-Dioxido-2-(4-(4-(1,2-dihydro-4(H)-2-oxo-3,1-benzoxazinyl)-piperidin-1-yl)-butyl)-1,2-benzisothiazol-3(2H)-one Step 1: A mixture of 20 g of N-t-butyloxycarbonyl-4-piperidinone, 13 g of 2-aminobenzyl alcohol 14 mL of acetic acid and 500 mL of toluene was refluxed under inert atmosphere with azeotropic removal of water for 16 h. After cooling to ambient temperature, 14 g of sodium cyanoborohydride and 200 mL tetrahydrofuran were added and the mixture was stirred at ambient temperature for 24 h. The reaction mixture was concentrated under reduced pressure, the residue was dissolved in 750 mL of ethyl acetate and washed with saturated aqueous NaHCO$_3$ (4×500 mL) and brine (250 mL). The organic layer was dried over MgSO$_4$, and the solvent was removed under reduced pressure. Chromatography of the crude product on silica gel, eluting with a gradient of 15–30% ethyl acetate-hexanes gave 24 g (78%) of 1-t-butyloxycarbonyl-4-((2-hydroxymethyl)phenylamino)piperidine as a gum.

Step 2. To a stirred mixture of 24 g of 1-t-butyloxycarbonyl-4-((2-hydroxymethyl)-phenylamino) piperidine, 250 mL of tetrahydrofuran, 41 mL of diisopropylethylamine cooled to 0° C. was added 8.54 g of triphosgene. The reaction was stirred at 0° C. for 1 h, and then at ambient temperature for 72 h. Ether (250 mL) was added, the mixture was cooled to 0° C. for 3 h, the precipitate removed by filtration and the filtrate was concentrated under reduced pressure. The residue was dissolved in 750 mL of ethyl acetate, washed with 5% aqueous citric acid (2×500 mL), water (250 mL), saturated aqueous NaHCO$_3$ (2×500 mL), dried over MgSO$_4$ and concentrated under reduced pressure.

The residue was boiled in ether (ca. 200 mL) until the solid had dissolved. Cooling overnight gave 19 g of 1-((1-t-butyloxycarbonyl)piperidin-4-yl)-1,2-dihydro-4(H)-3,1-benzoxazin-2-one as off-white crystals (75% yield).

Step 4. A stream of hydrogen chloride gas was dispersed through a stirred, ice cold solution of 19 g of 1-((1-t-butyloxycarbonyl)-piperidin-4-yl)-1,2-dihydro-4(H)-3,1-benzoxazin-2-one in 500 mL of ethyl acetate for 30 min. Stirring was continued at 0° C. for 1 h, then at ambient temperature for 1 h. The suspension was diluted with 250 mL of ether, aged for 1 h at 0° C., and the solid product was collected by filtration. Drying under reduced pressure for 18 h, gave 14 g of the hydrochloride salt of 1-(4-piperidinyl)-1,2-dihydro-4(H)-3,1-benzoxazin-2-one as an off-white solid (91%)

Step 5: From the hydrochloride salt of 1-(4-piperidinyl)-1,2-dihydro-4(H)-3,1-benzoxazin-2-one, and 2-(4-bromobutyl)-1,1-dioxido-1,2-benzothiazol-3(2H)-one using the procedure described for Example 15, Step 5 there was obtained a white solid, HCl salt: $^1$H NMR (400 MHz, CD$_3$OD) 8.10 (t, J=7.33 Hz, 1H), 7.99 (m, 3H), 7.42 (t, J=7.14 Hz, 1H), 7.27 (t, J=7.51 Hz, 2H), 7.16 (t, J=7.69 Hz, 1H), 5.17 (s, 2H), 4.27 (t, J=12.08 Hz, 1H), 3.87 (t, J=6.22 ppm, 2H), 3.67 (m, 3H), 3.19 (m, 3H), 2.98 (m, 2H), 2.16 (d, J=12.5 Hz, 2H), 1.92 (m, 4H).

EXAMPLE 18

1,1-Dioxido-2-(4-(4-(2-oxo-(1H)-quinolin-1-yl)-piperidin-1-yl)-butyl)-1,2-benzisothiazol-3(2H)-one From the hydrochloride salt of 1-(4-piperidyl)-2(1H)-quinolinone was prepared according to H. Ogawa et. al. *J. Med. Chem.* 1993, 36, 2011–2017, and 2-(4-bromobutyl)-1,1-dioxido-1,2-benzothiazol- 3(2H)-one using the procedure described for Example 15, Step 5 there was obtained a white solid: $^1$H NMR (300 MHz, CDCl$_3$) 8.08 (d, J=6.73 Hz, 1H), 7.90 (m, 3H), 7.7 (d, J=9.5 Hz, 1H), 7.6 (d, J=9.2 Hz, 1H), 7.56 (d, J=7.62 Hz, 1H), 7.26 (m, 2H), 6.71 (d, J=9.47 Hz, 1H), 3.85 (br m, 3H), 3.45 (br m, 1H), 3.25 (br m, 3H), 3.14 (br m, 6H), 1.95 (br s, 4H).

EXAMPLE 19

1,1-Dioxido-2-(4-(4-(2-oxo-(1H)-quinolin-1-yl)-piperidin-1-yl)-butyl)-5-nitro-1,2-benzisothiazol-3 (2H)-one From the hydrochloride salt of 1-(4-piperidyl)-2(1H)-quinolinone prepared according to H. Ogawa et. al. *J. Med. Chem.* 1993, 36, 2011–2017, and 2-(4-bromobutyl)-5-nitro-1,1-dioxido-1,2-benzothiazol-3(2H)-one using the procedure described for Example 15, Step 5 there was obtained a white solid: $^1$H NMR (300 MHz, CDCl$_3$) 8.88 (d, J=1.9 Hz, 1H), 8.73 (dd, J=8.36, 1.71 Hz, 1H), 8.15 (d, J=8.36 Hz, 1H), 7.79 (br m, 1H), 7.62 (d, J=3.47 Hz, 1H), 7.51 (m, 2H), 7.20 (m, 2H), 6.66 (d, J=9.33 Hz, 1H), 3.91 (t, J=7.33 Hz, 2H), 2.85 (br m, 2H), 2.48 (t, J=8.27 Hz, 2H), 2.21 (t, J=10.65 Hz, 2H).

EXAMPLE 20

6-Chloro-1,1-dioxido-2-(4-(4-(2-oxo-(1H)-quinolin-1-yl)-piperidin-1-yl)-butyl)-1,2-benzisothiazol-3(2H)-one From the hydrochloride salt of 1-(4-piperidyl)-2(1H)-quinolinone prepared according to H. Ogawa et. al. *J. Med. Chem.* 1993, 36, 2011–2017, and 2-(4-bromobutyl)-6-chloro-1,1-dioxido-1,2-benzothiazol-3(2H)-one using the procedure described for Example 15, Step 5 there was obtained a white solid, HCl salt: $^1$H NMR (300MHz, CD$_3$OD) 8.25 (d, J=1.66 Hz, 1H), 8.08 (d, J=8.17 Hz, 1H), 7.98 (dd, J=8.24, 1.71 Hz, 1H), 7.89 (d, J=9.52 Hz, 1H), 7.85 (d, J=8.55 Hz, 1H), 7.71 (d, J=7.68 Hz, 1H), 7.68 (t, J=7.57 Hz, 1H), 7.33 (t, J=7.65 Hz, 1H), 6.59 (d, J=9.52 Hz, 1H), 5.06 (br m, 1H), 3.88 (t, J=6.3 Hz, 2H), 3.69 (d, J=9.87 Hz, 2H), 3.26 (m, 6H), 1.94 (m, 6H).

EXAMPLE 21

5-Chloro-1,1-dioxido-2-(4-(4-(2-oxo-(1H)-quinolin-1-yl)-piperidin-1-yl)-butyl)-1,2-benzisothiazol-3(2H)-one From the hydrochloride salt of 1-(4-piperidinyl)-3-benzoxazolin-2-one and 2-(4-bromobutyl)-6-chloro-1,1-dioxido-1,2-benzothiazol-3(2H)-one using the procedure described for Example 15, Step 5 there was obtained a white solid, HCl salt: $^1$H NMR (300 MHz, CD$_3$OD) 8.11 (d, J=7.81 Hz, 1H), 8.13 (s, 1H), 8.02 (dd, J=8.3, 1.7 Hz, 1H), 7.90 (d, J=9.52 Hz, 1H), 7.85 (d, J=8.85 Hz, 1H), 7.71 (d, J=7.57 Hz, 1H), 7.67 (t, J=8.97 Hz, 1H), 7.33 (t, J=7.32 Hz, 1H), 6.59 (d, J=9.47 Hz, 1H), 5.08 (br m, 1H), 3.89 (t, J=6.11 Hz, 2H), 3.71 (d, J=8.74 Hz, 2H), 3.30 (br m, 6H), 2.0–1.9 (m, 6H).

EXAMPLE 22

1,1-Dioxido-2-(4-(4-(2-oxo-(1H)-quinolin-1-yl)-piperidin-1-yl)-butyl)-7-nitro-1,2-benzisothiazol-3(2H)-one From the hydrochloride salt of 1-(4-piperidinyl)-3-benzoxazolin-2-one and 2-(4-bromobutyl)-6-nitro-1,1-dioxido-1,2-benzothiazol-3(2H)-one using the procedure described for Example 15, Step 5 there was obtained a white solid: $^1$H NMR (300 MHz, CDCl$_3$) 8.65 (d, J=8.19 Hz, 1H), 8.44 (d, J=7.63 Hz, 1H), 8.10 (t, J=8.11 Hz, 1H), 7.81 (br s, 1H), 7.61 (d, J=9.34 Hz, 1H), 7.52 (m, 2H), 7.19 (t, J=7.33 Hz, 1H), 6.67 (d, J=9.28 Hz, 1H), 3.95 (t, J=7.38 Hz, 2H), 3.10 (d, J=10.37 Hz, 2H), 2.86 (br s, 2H), 2.49 (t, J=6.95 Hz, 2H), 2.22 (t, J=10.74 Hz, 2H), 1.98 (m, 2H), 1.70 (br m, 5H).

EXAMPLE 23

1,1-Dioxido-2-(4-(4-(2-oxo-(1H)-quinolin-1-yl)-piperidin-1-yl)-butyl)-4-methoxy-1,2-benzisothiazol-3(2H)-one From the hydrochloride salt of 1-(4-piperidyl)-2(1H)-quinolinone prepared according to H. Ogawa et. al. *J. Med. Chem.* 1993, 36, 2011–2017, and 2-(4-bromobutyl)-4-methoxy-1,1-dioxido-1,2-benzothiazol-3(2H)-one using the procedure described for Example 15, Step 5 there was obtained a white solid: $^1$H NMR (300 MHz, CDCl$_3$) 7.80 (t, J=8.1 Hz, 2H), 7.60 (d, J=9.33 Hz, 2H), 7.51 (m, 2H), 7.25 (m, 3H), 6.66 (d, J=9.27 Hz, 1H), 4.06 (s, 2H), 3.80 (t, J=6.9 Hz, 2H), 3.09 (dd, J=9.8, 1.8 Hz, 2H), 2.84 (m, 2H), 2.46 (t, J=7.2 Hz, 2H), 2.19 (t, J=11.6 Hz, 2H), 1.89 (br m, 2H), 1.69 (br m, 3H), 1.58 (s, 3H).

EXAMPLE 24

1,1-Dioxido-2-(4-(4-(2-oxo-3-benzoxazolinyl)-piperidin-1-yl)-butyl)-5-nitro-1,2-benzisothiazol-3(2H)-one From the hydrochloride salt of 1-(4-piperidinyl)-3-benzoxazolin-2-one and 2-(4-bromobutyl)-5-nitro-1,1-dioxido-1,2-benzothiazol-3(2H)-one using the procedure described for Example 15, Step 5 there was obtained a white solid, HCl salt: $^1$H NMR (300 MHz, CD$_3$OD) 8.82 (m, 2H), 8.39 (d, J=8.98 Hz, 1H), 7.25 (m, 4H), 4.50 (tt, J=8.01, 3.96 Hz, 1H), 3.93 (t, J=6.05 Hz, 2H), 3.74 (d, J=12.94 Hz, 2H), 3.26 (m, 4H), 2.73 (m, 2H), 2.17 (d, J=13.9 Hz, 2H), 1.93 (br m, 4H).

EXAMPLE 25

6-Chloro-1,1-dioxido-2-(4-(4-(2-oxo-3-benzoxazolinyl)-piperidin-1-yl)-butyl)-1,2-benzisothiazol-3(2H)-one From the hydrochloride salt of 1-(4-piperidinyl)-3-benzoxazolin-2-one and 2-(4-bromobutyl)-6-chloro-1,1-dioxido-1,2-benzothiazol-3(2H)-one using the procedure described for Example 15, Step 5 there was obtained a white solid, HCl salt: $^1$H NMR (300 MHz, CD$_3$OD) 8.22 (d, J=1.41 Hz, 1H), 8.07 (dd, J=8.3, 2.63 Hz, 1H), 7.96 (dd, J=8.19, 1.65 Hz), 7.33 (d, J=7.13 Hz, 1H), 7.23 (m, 2H), 4.49 (tt, J=12.21, 4.21 Hz, 11H), 3.88 (t, J=5.86 Hz, 2H), 3.74 (d, J=11.72 Hz, 2H), 3.23 (br m, 4H), 2.73 (m, 2H), 2.17 (d, J=13.43 Hz, 2H), 1.9 (br m, 4H).

EXAMPLE 26

5-Chloro-1,1-dioxido-2-(4-(4-(2-oxo-3-benzoxazolinyl)-piperidin-1-yl)-butyl)-1,2-benzisothiazol-3(2H)-one From the hydrochloride salt of 1-(4-piperidinyl)-3-benzoxazolin-2-one and 2-(4-bromobutyl)-5-chloro-1,1-dioxido-1,2-benzothiazol-3(2H)-one using the procedure described for Example 15, Step 5 there was obtained a white solid, HCl salt: $^1$H NMR (300 MHz, CD$_3$OD) 8.10 (d, J=6.59 Hz, 1H), 8.11 (s, 11H), 7.29 (m, 2H), 7.21 (m, 2H), 4.49 (tt, J=12.21, 4.21 Hz, 1H), 3.88 (t, J=5.86 Hz, 2H), 3.74 (d, J=11.72 Hz, 2H), 3.23 (br m, 4H), 2.73 (m, 2H), 2.17 (br d, 2H), 1.9 (br m, 4H).

EXAMPLE 27

1,1-Dioxido-2-(4-(4-(2-oxo-3-benzoxazolinyl)-piperidin-1-yl)-butyl)-7-nitro-1,2-benzisothiazol-3(2H)-one From the hydrochloride salt of 1-(4-piperidinyl)-3-benzoxazolin-2-one and 2-(4-bromobutyl)-7-nitro-1,1-dioxido-1,2-benzothiazol- 3(2H)-one using the procedure described for Example 15, Step 5 there was obtained a white solid, HCl salt: $^1$H NMR (300 MHz, CD$_3$OD) 8.76 (d, J=8.25 Hz, 1H), 8.50 (d, J=7.76 Hz, 1H), 8.22 (t, J=7.76 Hz), 7.24 (m, 4H), 4.49 (tt, J=12.21, 4.21 Hz, 1H), 3.96 (t, J=6.01 Hz, 2H), 3.76 (d, J=11.7 Hz, 2H), 3.23 (m, 4H), 2.73 (m, 2H), 2.17 (dd, J=14.5, 2.2 Hz, 2H), 1.9 (m, 4H).

EXAMPLE 28

1,1-Dioxido-2-(4-(4-(2-oxo-3-benzoxazolinyl)-piperidin-1-yl)-butyl)-4-methoxy-1,2-benzisothiazol-3(2H)-one From the hydrochloride salt of 1-(4-piperidinyl])-3-benzoxazolin-2-one and 2-(4-bromobutyl)-4-methoxy-1,1-dioxido-1,2-benzothiazol-3(2H)-one using the procedure described for Example 15, Step 5 there was obtained a white solid: $^1$H NMR (400 MHz, CDCl$_3$) 7.83 (t, J=8.06 Hz, 1H), 7.49 (d, J=7.69 Hz, 1H), 7.46 (d, J=7.51 Hz, 1H), 7.30 (d, J=8.6 Hz, 1H), 7.17 (m, 3H), 4.56 (dt, J=11.72, 4.21 Hz, 1H), 4.07 (s, 3H) 3.79 (m, 4H), 3.16 (m, 2H), 2.88 (m, 4H), 2.07 (d, J=13.0 Hz, 2H), 1.96 (m, 4H).

EXAMPLE 29

1,1-Dioxido-2-(4-(4-(5-chloro-2-oxo-3-benzoxazolinyl)-piperidin-1-yl)-butyl)-1,2-benzisothiazol-3(2H)-one From the hydrochloride salt of 5-chloro-1-(4-piperidinyl)-3-benzoxazolin-2-one and 2-(4-bromobutyl)-1,1-dioxido-1,2-benzothiazol-3(2H)-one using the procedure described for Example 15, Step 5 there was obtained a white solid, HCl salt: $^1$H NMR (400 MHz, CD$_3$OD) 8.10 (td, J=6.0, 1.2 Hz, 2H), 8.02–7.94 (overlapping dt, 2H), 7.43 (d, J=1.8 Hz, 1H), 7.24 (d, J=8.4 Hz, 1H), 7.16 (dd, J=8.6, 2.0 Hz, 1H), 4.43 (tt, J=12.4, 4.4, 1H), 3.88 (t, J=6.4, 2H), 3.66 (d, J=11.5, 2H), 3.16–3.05 (m, 4H), 2.66 (qd, J=13.0, 3.7, 2H), 2.13 (d, J=13.4, 2H), 2.01–1.88 (m, 4H).

EXAMPLE 30

1,1-Dioxido-2-(4-(4-(3a-(R)-8a-(S)-2-oxo-3,3a,8,8a-tetrahydro-2H-indeno[1,2-d]oxazolinyl)-piperidin-1-yl)-butyl)-1,2-benzisothiazol-3(2H)-one From the hydrochloride salt of 4-(3a-(R)-8a-(S)-2-oxo-3,3a,8,8a-tetrahydro-2H-indeno[1,2-d]oxazolinyl)-piperidine and 2-(4-bromobutyl)-1,1-dioxido-1,2-benzothiazol-3(2H)-one using the procedure described for Example 15, Step 5 there was obtained a white solid, HCl salt: $^1$H NMR (400 MHz, CD$_3$OD) 8.10–8.07 (m, 1H), 8.02–7.94 (m, 2H), 7.59 (d, J=7.1 Hz, 1H), 7.32–7.31 (m, 4H), 5.37–5.30 (m, 2H), 3.86 (m, 3H), 3.55–3.41 (m, 4H), 3.25–2.98 (m, 5H), 2.55 (m, 2H), 2.14 (m, 1H), 1.94–1.77 (m, 4H).

EXAMPLE 31

1,1-Dioxido-2-(4-(4-(2-oxonaphth[2,3-d]oxazolinyl) -piperidin-1-yl)-butyl)-1,2-benzisothiazol-3(2H)-one From the hydrochloride salt of 4-(2-oxonaphth[2,3-d] oxazolinyl)-piperidine and 2-(4-bromobutyl)-1,1-dioxido-1, 2-benzothiazol-3(2H)-one using the procedure described for Example 15, Step 5 there was obtained a white solid, HCl salt: $^1$H NMR (400 MHz, CD$_3$OD) 8.11 (td, J=6.5, 0.9 Hz, 2H), 8.02–7.94 (m, 2H), 7.89 (d, J=8.2 Hz, 2H), 7.68 (d, J=5.3 Hz, 2H), 7.50–7.42 (m, 2H), 4.58 (tt, J=12.3, 4.0 Hz, 1H), 3.90 (t, J=6.4 Hz, 2H), 3.72 (d, J=13.0 Hz, 2H), 3.22–3.15 (m, 4H), 2.80 (qd, J=12.8, 3.0 Hz, 2H), 2.21 (d, J=13.7 Hz, 2H), 2.00–1.92 (m, 4H).

EXAMPLE 32

1,1-Dioxido-2-(4-(4-(6-methyl-2-oxo-3-benzoxazolinyl)-piperidin-1-yl)-butyl)-1,2-benzisothiazol-3(2H)-one From the hydrochloride salt of 4-(6-methyl-2-oxo-3-benzoxazolinyl)-piperidine and 2-(4-bromobutyl)-1,1-dioxido-1,2-benzothiazol-3(2H)-one using the procedure described for Example 15, Step 5 there was obtained a white solid, HCl salt: $^1$H NMR (400 MHz, CD$_3$OD) 8.09 (td, J=5.7, 1.5 Hz, 2H), 8.03–7.94 (m, 2H), 7.21 (d, J=8.1 Hz, 11H), 7.11 (s, 11H), 7.06 (d, J=8.0 Hz, 11H), 4.46 (tt, J=12.2, 4.0 Hz, 11H), 3.88 (t, J=6.4 Hz, 2H), 3.71 (d, J=12.5 Hz, 2H), 3.26–3.16 (m, 4H), 2.71 (qd, J=13.5, 3.5 Hz, 2H), 2.38 (s, 3H), 2.14 (d, J=14.1 Hz, 2H), 1.97–1.91 (m, 4H).

EXAMPLE 33

1,1-Dioxido-2-(4-(4-(2-oxo-5-phenyl-3-benzoxazolinyl)-piperidin-1-yl)-butyl)-1,2-benzisothiazol-3(2H)-one From the hydrochloride salt of 4-(2-oxo-5-phenyl-3-benzoxazolinyl)-piperidine and 2-(4-bromobutyl)-1,1-dioxido-1,2-benzothiazol-3(2H)-one using the procedure described for Example 15, Step 5 there was obtained a white solid, HCl salt: $^1$H NMR (400 MHz, CD$_3$OD) 8.11–8.07 (overlapping t, 2H), 8.02–7.94 (m, 2H), 7.64 (d, J=7.1 Hz, 2H), 7.58 (d, J=1.5 Hz, 1H), 7.47–7.41 (m, 3H), 7.38–7.33 (m, 2H), 4.57 (tt J=12.4, 4.2 Hz, 1H), 3.88 (t, J=6.4 Hz, 2H), 3.71 (d, J=12.1 Hz, 2H), 3.23–3.13 (m, 4H), 2.77 (qd, J=14.0, 3.0 Hz, 2H), 2.18 (d, J=13.9, 2H), 1.97–1.90 (m, 4H).

EXAMPLE 34

1,1-Dioxido-2-(4-(4-(6-methoxy-2-oxo-3-benzoxazolinyl)-piperidin-1-yl)-butyl)-1,2-benzisothiazol-3(2H)-one From the hydrochloride salt of 4-(6-methoxy-2-oxo-3-benzoxazolinyl)-piperidine and 2-(4-bromobutyl)-1,1-dioxido-1,2-benzothiazol-3(2H)-one using the procedure described for Example 15, Step 5 there was obtained a white solid, HCl salt: $^1$H NMR (400 MHz, CD$_3$OD) 8.14 (td, J=6.4, 1.4 Hz, 2H), 8.05–8.00 (overlapping td, 2H), 7.26 (d, J=8.6 Hz, 1H), 6.99 (d, J=2.4 Hz, 1H), 6.86 (dd, J=8.8, 2.4 Hz, 1H), 4.48 (tt, J=12.1, 4.2 Hz, 1H), 3.92 (t, J=6.2 Hz, 2H), 3.83 (s, 3H), 3.75 (d, J=12.1, 2H), 3.34–3.22 (m, 4H), 2.74 (qd, J=12.6, 3.6 Hz, 2H), 2.19 (d, J=13.5 Hz, 2H), 2.00–1.95 (m, 4H).

EXAMPLE 35

1,1-Dioxido-2-(4-(4-(6-carbomethoxy-2-oxo-3-benzoxazolinyl)-piperidin-1-yl)-butyl)-1,2-benzisothiazol-3(2H)-one From the hydrochloride salt of 4-(6-carbomethoxy-2-oxo-3-benzoxazolinyl)-piperidine and 2-(4-bromobutyl)-1,1-dioxido-1,2-benzothiazol-3(2H)-one using the procedure described for Example 15, Step 5 there was obtained a white solid, HCl salt: $^1$H NMR (400 MHz, CD$_3$OD) 8.01 (t, J=6.8 Hz, 2H), 7.94–7.86 (m, 3H), 7.78 (d, J=1.5 Hz, 1H), 7.31 (d, J=8.4, 1H), 4.40 (m, 1H), 3.83 (s, 3H), 3.79 (t, J=6.6, 2H), 3.72 (d, J=7.1, 2H), 3.05 (m, 2H), 2.97 (m, 2H), 2.60 (m, 2H), 2.05 (d, J=12.5, 2H), 1.89–1.79 (m, 4H).

EXAMPLE 36

1,1-Dioxido-2-(4-(4-(5-ethylsulfonyl-2-oxo-3-benzoxazolinyl)-piperidin-1-yl)-butyl)-1,2-benzisothiazol-3(2H)-one From the hydrochloride salt of 4-(5-ethylsulfonyl-2-oxo-3-benzoxazolinyl)-piperidine and 2-(4-bromobutyl)-1,1-dioxido-1,2-benzothiazol-3(2H)-one using the procedure described for Example 15, Step 5 there was obtained a white solid, HCl salt: $^1$H NMR (400 MHz, CD$_3$OD) 8.01 (t, J=6.0 Hz, 2H), 7.93–7.87 (m, 2H), 7.77 (s, 1H), 7.67 (d, J=7.1 Hz, 1H), 7.42 (d, J=8.2 Hz, 1H), 4.48 (m, 1H), 3.79 (m, 2H), 3.60 (d, J=11.2 Hz, 2H), 3.14–3.06 (overlapping q & m, 6H), 2.61 (br q, J=12.5 Hz, 2H), 2.10 (d, J=13.4 Hz, 2H), 1.85 (m, 4H), 1.15 (t, J=6.2 Hz, 3H).

EXAMPLE 37

1,1-Dioxido-2-(4-(4-(2-oxo-3-oxazolo[4,5-b]pyridyl) -piperidin-1-yl)-butyl)-1,2-benzisothiazol-3(2H)-one From the hydrochloride salt of 4-(2-oxo-3-oxazolo[4,5-b]pyridyl)-piperidine and 2-(4-bromobutyl)-1,1-dioxido-1, 2-benzothiazol-3(2H)-one using the procedure described for Example 15, Step 5 there was obtained a white solid, HCl salt: $^1$H NMR (400 MHz, CD$_3$OD) 8.03–7.99 (m, 3H), 7.94–7.85 (2 overlapping td, 2H), 7.49 (dd, J=8.0, 1.2 Hz, 1H), 7.07 (dd, J=8.0, 5.0 Hz, 1H), 4.56 (tt, J=12.1, 4.1 Hz, 1H), 3.79 (t, J=6.4 Hz, 2H), 3.63 (t, J=12.8 Hz, 2H), 3.20–3.09 (m, 4H), 2.82 (qd, J=13.3, 3.5 Hz, 2H), 2.09 (d, J=13.4, 2H), 1.88–1.78 (m, 4H).

EXAMPLE 38

1,1-Dioxido-2-(4-(4-(7-carbethoxy-2-oxo-3-benzoxazolinyl)-piperidin-1-yl)-butyl)-1,2-benzisothiazol-3(2H)-one From the hydrochloride salt of 4-(7-carbethoxy-2-oxo-3-benzoxazolinyl)-piperidine and 2-(4-bromobutyl)-1,1-dioxido-1,2-benzothiazol-3(2H)-one using the procedure described for Example 15, Step 5 there was obtained a white solid, HCl salt: $^1$H NMR (400 MHz, CD$_3$OD) 8.01 (td, J=6.4, 1.5 Hz, 2H), 7.94–7.86 (m, 2H), 7.63 (dd, J=8.1, 1.1 Hz, 1H), 7.47 (dd, J=7.9, 1.1 Hz, 1H), 7.26 (t, J=8.1 Hz, 1H), 4.42 (tt, J=12.1, 4.0 Hz, 1H), 3.87 (s, 3H), 3.80 (t, J=6.2, 2H), 3.63 (d, J=12.8 Hz, 2H), 3.16–3.06 (m, 4H), 2.65 (qd, J=13.0, 4.0 Hz, 2H), 2.09 (d, J=13.5 Hz, 2H), 1.89–1.83 (m, 4H).

EXAMPLE 39

1,1-Dioxido-2-(4-(4-(5-tert-butyl-2-oxo-3-benzoxazolinyl)-piperidin-1-yl)-butyl)-1,2-benzisothiazol-3(2H)-one From the hydrochloride salt of 4-(5-tert-butyl-2-oxo-3-benzoxazolinyl)-piperidine and 2-(4-bromobutyl)-1,1- dioxido-1,2-benzothiazol-3(2H)-one using the procedure described for Example 15, Step 5 there was obtained a white solid: $^1$H NMR (300 MHz, CDCl$_3$) 8.07 (dd, J=6.6, 2.25 Hz, 1H), 7.88 (m, 3H), 7.19 (s, 1H), 7.11 (s, 2H), 4.17 (tt, J=12.21, 3.66 Hz, 1H), 3.85 (t, J=7.14 Hz, 2H), 3.09 (d, J=10.85 Hz, 2H), 2.46 (t, J=7.38 Hz, 2H), 2.36 (dt, J=12.15, 3.5 Hz, 2H), 2.13 (dt, J=10.89, 1.27 Hz, 2H), 1.91 (m, 4H), 1.66 (m, 2H), 1.342 (s, 9H).

EXAMPLE 40

1,1-Dioxido-2-(4-(4-(5,7-dimethyl-2-oxo-3-benzoxazolinyl)-piperidin-1-yl)-butyl)-1,2-benzisothiazol-3(2H)-one From the hydrochloride salt of 4-(5,7-dimethyl-2-oxo-3-benzoxazolinyl)-piperidine and 2-(4-bromobutyl)-1,1-dioxido-1,2-benzothiazol-3(2H)-one using the procedure described for Example 15, Step 5 there was obtained a white solid: $^1$H NMR (300 MHz, CDCl$_3$) 8.08 (d, J=7.27 Hz, 1H), 7.90 (m, 3H), 7.65 (br m, 1H), 6.752 (s, 1H), 4.55 (br m, 1H), 3.85 (br t, 2H), 3.70 (br m, 2H), 3.32 (br m, 2H), 3.10 (br m, 2H), 2.87 (br m, 2H), 2.413 (s, 3H), 2.318 (s, 3H), 2.06 (br m, 6H).

EXAMPLE 41

2-(4-Bromobutyl)-1,1-dioxido-1,2-benzothiazol-3(2H)-one

The general procedure of J. D. Commerford and H. B. Donahue *J. Org. Chem.* 1956, 21, 583-4 was modified: A mixture of 6 g of sodium saccharin, 100 mL of 1,4-dibromobutane, and 5 mL of N,N-dimethylformamide was heated at 50° C. overnight. After cooling to ambient temperature, the mixture was diluted with 250 mL of ether and 50 mL of water. The aqueous layer was extracted with two additional 50 mL portions of ether and the combined organic extracts were dried over MgSO$_4$ and concentrated under reduced pressure. The excess 1,4-dibromobutane was removed by short path vacuum distillation and the oily residue purified by crystallization from ether-hexane, mp 71°–2° C.

EXAMPLE 42

2-(4-Bromobutyl)-1,1-dioxido-5-methoxy-1,2-benzothiazol-3(2H)-one

The general procedure of J. D. Commerford and H. B. Donahue *J. Org. Chem.* 1956,21, 583-4 was modified: A mixture of 0.5 g of 3,3-dioxido-5-methoxy-1,2-benzothiazol-3(2H)-one prepared as described by J. G. Lombardino, *J. Org. Chem.* 1971, 36, 1843-5, 1 mL of N,N-dimethylformamide and 0.1 g of sodium hydride 60% oil dispersion was stirred at ambient temperature for 15 min, and 1.4 mL of 1,4-dibromobutane was added. After stirring at ambient temperature overnight, the mixture was diluted with 25 mL of ethyl acetate, washed with 25 mL of sat'd NaHCO$_3$, 25 mL of sat'd brine and dried over MgSO$_4$. Removal of solvents under reduced pressure and vacuum distillation gave 0.8 g of crude product as a viscous oil which was free of 1,4-dibromobutane by $^1$H-NMR and was used without further purification.

EXAMPLE 43

2-(4-Bromobutyl)-1,1-dioxido-5-nitro-1,2-benzothiazol-3(2H)-one

The general procedure of J. D. Commerford and H. B. Donahue *J. Org. Chem.* 1956, 21, 583-4 was modified: A stirred mixture of 1.0 g of 3,3-dioxido-5-nitro-1,2-benzothiazol-3(2H)-one prepared as described by W. S. Saari and J. E. Schwering, *J. Heterocyclic Chem.* 1986, 23, 1253, and 6 mL of 1N NaOH was warmed to dissolution and allowed to cool to ambient temperature for 15 min. The mixture was concentrated to dryness under reduced pressure and the white solid azeotropically dried with 20 mL of toluene. The resulting sodium salt was dissolved in 3 mL of N,N-dimethylformamide and 2.6 mL of 1,4-dibromobutane was added. After stirring at ambient temperature overnight, the mixture was diluted with 25 mL of ethyl acetate, washed with 25 mL of sat'd NaHCO$_3$, 25 mL of sat'd brine and dried over MgSO$_4$. Removal of solvents under reduced pressure and vacuum distillation gave 1.1 g of crude product as a solid which was free of 1,4-dibromobutane by $^1$H-NMR and was used without further purification: $^1$H NMR (300 MHz, 30 CDCl$_3$): 8.87 (d, J=0.5 Hz, 1H), 8.74 (dd, J=8.38, 2.03 Hz, 1H), 8.15 (dd, J =8.41, 2.0 Hz, 1H), 3.88 (t, J=6.8 Hz, 2H), 3.47 (t, J=6.3 Hz, 2H), 2.02 (m, 4H).

EXAMPLE 44

1,1-Dioxido-2-(4-(spiro-1,3-dihydro-1-oxo-2H-indenyl)-2,4'-piperidin-1'-yl)butyl)-1,2-benzisothiazol-3(2H)-one Step 1: To a ice cold, stirred mixture of 55 g of ethyl isonipecotate, 200 mL of ether, 200 mL of saturated sodium carbonate and 200 mL of water was added dropwise 40 mL of benzoyl chloride. The resulting mixture was allowed to warm and stir overnight, diluted with 200 mL of ethyl acetate and separated. The organic layer was washed with 200 mL of 1N hydrochloric acid, dried over MgSO$_4$, and concentrated. Drying the residue under vacuum gave 83.3 g (92%) of ethyl 1-benzoyl-4-piperidinecarboxylate as a white solid.

Step 2: A stirred solution of 176 mL of commercial 1M lithium bistrimethylsilylamide in tetrahydrofuran was diluted with 100 mL of tetrahydrofuran and cooled to −78° C. under inert atmosphere. A solution of 44 g of ethyl 1-benzoyl-4-piperidinecarboxylate in 200 mL of tetrahydrofuran was added dropwise keeping the temperature below −60° C., followed by 21 mL of benzyl bromide. The resulting mixture was allowed to warm and stir overnight, diluted with 200 mL of 1N hydrochloric acid, 200 mL of ethyl acetate and separated. The organic layer was washed with 200 mL of 1N hydrochloric acid, dried over MgSO$_4$, and concentrated. The residue was dissolved in 300 mL of toluene, filtered and concentrated under reduced pressure. Drying under reduced pressure gave 56.3 g of ethyl 1-benzoyl-4-(phenylmethyl)-4-piperidinecarboxylate as a viscous oil homogeneous by thin layer chromatography, eluting with 1:1 ethyl acetate: hexane, $^1$H NMR (300 MHz, CDCl$_3$) 1.20 (t, 3H), 1.40 (m, 1H), 1.60 (m, 1H), 2.07 (m, 1H), 2.22 (m, 1H), 2.85 (d, 2H), 3.08 (m, 1H), 3.65 (m, 1H), 4.12 (q, 2H), 4.65 (m, 1H), 7.04 (m, 2H), 7.24 (m, 3H), 7.38 (m, 5H).

Step 2: A mixture of 65 g of ethyl 1-benzoyl-4-(phenylmethyl)-4-piperidinecarboxylate, 300 g of polyphosphoric acid and 500 mL of xylene was heated at reflux overnight. The xylene layer was decanted off and the residue washed with two additional 100 mL portions of xylene. The residue was dissolved in 1L of water and 1L of ethyl acetate and separated. The aqueous was extracted with two additional 200 mL portions of ethyl acetate and the combined organic extracts were washed with 500 mL of sat'd Na$_2$CO$_3$, water and dried over MgSO$_4$. Removal of solvents under reduced pressure gave 27 g of 1'-benzoyl-1,3-dihydro-1- oxo-spiro(2H-indenyl-2,4'-piperidine) as crystalline solid, mp 149°–154° C.; $^1$H NMR (300 MHz, CDCl$_3$) 1.50 (m, 2H), 2.00 (m, 2H), 3.12 (m, 2H), 3.25 (ddd, 2H), 3.90 (m, 1H), 4.62 (m, 1H), 7.43 (m, 1H), 7.63 (dd, 1H), 7.79 (d, 1H).

Step 3: A mixture of 27 g of 1'-benzoyl-1,3-dihydro-1-oxo-spiro(2H-indenyl-2,4'-piperidine) 400 mL of ethanol and 100 mL of conc. hydrochloric acid was heated at reflux for 48 hrs. The mixture was concentrated to remove ethanol, diluted 200 mL with water and extracted with two additional portions of ethyl acetate. The aqueous layer was basified with 20% NaOH and extracted with three 200 mL portions of ethyl acetate. The combined organic extracts were washed with 50 mL of water and dried over MgSO$_4$. Removal of solvents under reduced pressure gave 18 g of 1,3-dihydro-1-oxo-spiro(2H-indene-2,4'-piperidine) as brown solid product: $^1$H NMR (300 MHz, CDCl$_3$) 1.35 (dd, 2H), 1.62 (br s, 1H), 1.88 (ddd, 2H), 2.81 (ddd, 2H), 3.10 (s, 2H), 3.17 (m, 2H), 7.38 (t, 1H), 7.46 (d, 1H), 7.60 (t, 1H), 7.77 (d, 1H).

Step 4: From 1,3-dihydro-1-oxo-spiro(2H-indenyl-2,4'-piperidine), and 2-(4-bromobutyl)-1,1-dioxido-1,2-benzothiazol-3(2H)-one using the procedure described for Example 15, Step 5 there was obtained 1,1-dioxido-2-(4-(spiro(1,3-dihydro-1-oxo-2H-indene-2,4'-piperidin-1'-yl) butyl)-1,2-benzisothiazol-3(2H)-one as a white solid: $^1$H NMR (400 MHz, CDCl$_3$): 8.06 (d, J=6.8 Hz, 1H), 7.92 (d, J=6.6 Hz, 1H), 7.89–7.83 (m, 2H), 7.75 (d, J=7.7 Hz, 1H), 7.59 (t, J=7.4 Hz, 1H), 7.44 (d, J=6.96 Hz, 1H), 7.37 (t, J=7.4 Hz, 1H), 3.83 (t, J=7.4 Hz, 2H), 3.02 (s, 2H), 2.95 (t, J=1 1.36 Hz, 2H), 2.45 (t, J=7.4 Hz, 2H), 2.17–2.01 (m, 4H), 1.94–1.90 (m, 2H), 1.67–1.64 (m, 2H), 1.38 (br d, J=12 Hz, 2H).

EXAMPLE 45

1,1-Dioxido-2-(4-(4'-(3,4-dihydro-1-oxonapththalene)-2(1H)-spiropiperidin-1'-yl)butyl)-1,2-benzisothiazol-3(2H)-one From 4'-(3,4-dihydro-1-oxonapththalene)-2(1H)-spiropiperidine, prepared as described by P. J. Gilligan, et al., *J. Med. Chem.* 1994, 37, 364–370, and 2-(4-bromobutyl)-1,1-dioxido-1,2-benzothiazol-3(2H)-one using the procedure described for Example 15, Step 5 there was obtained a white solid: mp 226°–8° C.

EXAMPLE 46

4-(3,4-Dihydro-6-methyl-spiro[2H-1-benzopyran-2, 4'-piperidine-4(3H)-one]-1'-yl)-butylphthalimide From 3,4-dihydro-6-methyl-spiro[2H-1-benzopyran-2,4'-piperidine, and 2-(4-bromobutyl)-phthalimide using the procedure described for Example 15, Step 5 there was obtained a white solid:mp>275° C. dec.

EXAMPLE 47

4-(Spiro(piperidine-4,6'-[6H]thieno[2,3-b]thiopyran-4'(5'H)-one-1'-yl)-butylphthalimide From 4-(spiro(piperidine-4,6'-[6H]thieno[2,3-b] thiopyran-4'(5'H)-one, and 2-(4-bromobutyl)-phthalimide using the procedure described for Example 15, Step 5 there was obtained a white solid:mp 261°–3° C. dec.

EXAMPLE 48

4-(Spiro[benzothiazol-2(3H),4'-piperidin-1'-yl)-butylphthalimide

Step 1: A solution of 4-piperidone hydrochloride hydrate (2 gram, 13 mmol), bromobutylphthalimide (3.67 gram, 13 mmol) and triethylamine (3.4 ml, 26 mmol) in Chloroform (25 ml) was refluxed overnight. The reaction mixture was washed with sat. NaHCO$_3$ and was dried over Na$_2$SO$_4$. Purification using flash chromatography gave 4-(4'-ketopiperidinyl)butylphthalimide (0.85 gram).

Step 2: A solution of 4-(4'-ketopiperidinyl) butylphthalimide (200 mg, 0.67 mmol), 2-aminothiophenol (125 ml, 0.73mmol) and tosic acid (30 mg) in benzene (25 ml) was refluxed overnight. The reaction mixture was concentrated and the residue was partitioned between ethyl acetate and sat. NaHCO$_3$. The organic layer was dried over Na$_2$SO$_4$. Chromatography gave a white solid: $^1$H NMR (300 MHz, CDCl$_3$): 8.01–7.95 (m, 2H), 7.88–7.82 (m, 2H), 7.17 (d, J=7.57 Hz, 1H), 7.04 (t, 1H), 6.86 (t, J=3.76 Hz, 1H), 6.78 (d, J=7.63 Hz, 1H), 4.14 (br s, 1H), 3.85 (t, J=7.04 Hz, 2H), 2.89–2.06 (m, 2H), 2.54–2.30 (m, 6H), 2.18–2.06 (m, 2H), 1.90–1.72 (m, 2H), 1.69–1.37 (m, 2H).

EXAMPLE 49

4-(3,4-Dihydro-6-methoxy-spiro[2H-1-benzopyran-2,4'-piperidine-4(3H)-one]-1'-yl)-butylphthalimide From 3,4-dihydro-6-methoxy-spiro[2H-1-benzopyran-2, 4'-piperidine-4(3H)-one and 2-(4-bromobutyl)-phthalimide using the procedure described for Example 15, Step 5 there was obtained a white solid:mp 11°–113° C.

EXAMPLE 50

4-(3,4-Dihydro-6-methanesulfonylamidyl-spiro[2H-1-benzopyran-2,4'-piperidine-4(3H)-one]-1'-yl)-butylphthalimide From 3,4-dihydro-6-methanesulfonylamidyl-spiro [2H-1-benzopyran-2,4'-piperidine-4(3H)-one and 2-(4-bromobutyl)-phthalimide using the procedure described for Example 15, Step 5 there was obtained a white solid: mp 89°–90° C.

EXAMPLE 51

1,1-Dioxido-2-(4-(spiro[benzothiazol-2(3H),4'-piperidin-1'-yl)-butyl)-1,2-benzisothiazol-3(2H)-one From 2-(4-bromobutyl)-1,1-dioxido-1,2-benzothiazol-3 (2H)-one, 4-piperidone and 2-aminothiophenol using the procedure described for Example 48 there was obtained a white solid: mp 178°–80° C.

EXAMPLE 52

4-(6-Trifluoromethyl-spiro[benzothiazol-2(3H),4'-piperidin-1'-yl)-butylphthalimide From 4-(4'-ketopiperidinyl)butylphthalimide and 2-amino-5-trifluoromethylthiophenol using the procedure described for Example 48, Step 2 there was obtained a white solid: mp 157°–8° C.

EXAMPLE 53

1,1-Dioxido-2-(4-(spiro[benzofuran-2(3H),4'-piperidin]-1'-yl)-butyl)-1,2-benzisothiazol-3(2H)-one From spiro[benzofuran-2(3H),4'-piperidine] prepared as described by R. C. Effland, et al. *J. Heterocyclic Chem.* 1981, 18, 811, and 2-(4-bromobutyl)-1,1-dioxido-1,2-benzothiazol-3(2H)-one using the procedure described for Example 15, Step 5 there was obtained a white solid: mp 98°–100° C.

EXAMPLE 54

4-(Spiro[benzofuran-2(3H),4'-piperidin]-1'-yl)-butylphthalimide

From spiro[benzofuran-2(3H),4'-piperidine] prepared as described by R. C. Effland, et al. *J. Heterocyclic Chem.* 1981, 18, 81 1, and 2-(4-bromobutyl)-phthalimide using the procedure described for Example 15, Step 5 there was obtained a white solid: mp 255°–7° C.

EXAMPLE 55

4-(Spiro[2H-1,3-benzoxazine-2,4'-piperidin]-1'-yl)-butylphthalimide

From spiro[2H- 1,3-benzoxazine-2,4'-piperidine] and 2-(4-bromobutyl)-phthalimide using the procedure described for Example 15, Step 5 there was obtained a white solid: mp 165°–7° C.

EXAMPLE 56

3,3-Dioxido-1,2-dehydro-2-(4-(spiro[2H-indenyl-2, 4'-piperidine-1(3H)-one]-1'-yl)-butyl)-naphth[1,2-d] isothiazol-1-one From 1,3-dihydro-1-oxo-spiro(2H-indenyl-2,4'-piperidine) and 2-(4-bromobutyl)-3,3-dioxido-1,2-dehydronaphth[1,2-d]isothiazol-1-one using the procedure described for Example 15, Step 5 there was obtained a white solid: $^1$H NMR (300 MHz, CDCl$_3$): 9.27 (d, J=8.4 Hz, 1H), 8.30 (d, J=8.5 Hz, 1H), 8.00 (d, J=7.6 Hz, 1H), 7.88 (d, J=8.5 Hz, 1H), 7.82–7.73 (m, 3H), 7.56 (t, 1H), 7.43 (d, J=7.6 Hz, 1H), 7.36 (t, 3H), 3.85 (t, J=7.4 Hz, 2H), 3.01 (s, 2H), 2.97 (br d, 2H), 2.14–2.0 (m, 4H), 1.90 (m, 8H), 1.69 (m, 2H), 1.38 (br d, J=12 Hz, 2H); mp (HCl salt) 243°–5° C.

EXAMPLE 57

1,1-Dioxido-2-(4-(spiro[2H-indenyl-2,4'-piperidine-1(3H)-one]-1'-yl)-butyl)-4-methoxy-1,2-benzisothiazol-3(2H)-one From 1,3-dihydro-1-oxo-spiro(2H-indenyl-2,4'-piperidine) and 1,1-dioxido-2-(4-bromobutyl)-4-methoxy-1, 2-benzisothiazol-3(2H)-one using the procedure described for Example 15, Step 5 there was obtained a white solid: $^1$H NMR (300 MHz, CDCl$_3$): 7.83–7.74 (m, 2H), 7.61 (t, J=7.4 Hz, 1H), 7.56 (m, 2H), 7.34 (t, J=7.7 Hz, 1H), 7.29 (m, 1H), 4.05 (s, 3H), 3.78 (t, J=7.3 Hz, 2H), 3.02 (s, 2H), 2.96 (br d, J=11 Hz, 2H), 2.43 (t, J=7.6 Hz, 2H), 2.17–2.0 (m, 4H), 1.87 (m, 2H), 1.65 (m, 2H), 1.31 (br d, J=12 Hz, 2H).

EXAMPLE 58

1,1-Dioxido-2-(4-(spiro[2H-indenyl-2,4'-piperidine-1(3H)-one]-1 '-yl)-butyl)-7-methoxy-1,2-benzisothiazol-3(2H)-one From 1,3-dihydro-1-oxo-spiro(2H-indenyl-2,4'-piperidine) and 1,1-dioxido-2-(4-bromobutyl)-7-methoxy-1, 2-benzisothiazol-3(2H)-one using the procedure described for Example 15, Step 5 there was obtained a white solid: $^1$H NMR (300 MHz, CDCl$_3$): 7.77–7.72 (m, 2H), 7.61–56 (m, 2H), 7.44 (d, J=7.6 Hz, 1H), 7.37 (t, 1H), 7.28 (d, 1H), 4.05 (s, 3H), 3.80 (t, J=7.3 Hz, 2H), 3.02 (s, 2H), 2.96 (m, 2H), 2.44 (t, J=7.5 Hz, 2H), 2.13–2.03 (m, 4H), 1.89 (m, 2H), 1.65 (m, 2H), 1.39 (br d, J=12 Hz, 2H); mp (HCl salt) 130° C. (dec).

EXAMPLE 59

1,1-Dioxido-2-(4-(spiro(1,3-dihydro-1-oxo-2H-indenyl-2,4'-piperidin-1'-yl)butyl)-5-methoxy-1,2-benzisothiazol-3(2H)-one From 1,3-dihydro-1-oxo-spiro(2H-indenyl-2,4'-piperidine) and 1,1-dioxido-2-(4-bromobutyl)-5-methoxy-1, 2-benzisothiazol-3 (2H)-one using the procedure described for Example 15, Step 5 there was obtained a white solid: $^1$H NMR (400 MHz, CDCl$_3$): 7.80 (d, J=8.6 Hz, 1H), 7.75 (d, J=7.6 Hz, 1H), 7.6 (d, J=7.6 Hz, 1H), 7.59 (t, 1H), 7.48–7.37 (m, 2H), 7.32 (t, J=7.8 Hz, 1H), 7.29 (d, 1H), 3.95 (s, 3H), 3.81 (t, J=7.4 Hz, 2H), 3.02 (s, 2H), 2.95 (br d, J=11 Hz, 2H), 2.44 (t, J=7.4 Hz, 2H), 2.14–2.0 (m, 4H), 1.90 (m, 2H), 1.65 (m, 2H), 1.38 (br d, J=12 Hz, 2H); mp (HCl salt) 205°–7° C.

EXAMPLE 60

1,1-Dioxido-2-(4-(spiro(1,3-dihydro-1-oxo-2H-indenyl-2,4'-piperidin-1'-yl)butyl)-6-methoxy-1,2-benzisothiazol-3(2H)-one From 1,3-dihydro-1-oxo-spiro(2H-indenyl-2,4'-piperidine) and 1,1-dioxido-2-(4-bromobutyl)-6-methoxy-1, 2-benzisothiazol-3(2H)-one using the procedure described for Example 15, Step 5 there was obtained a white solid:rom spiro[2H-indene-2,4'-piperidine and 2-(4-bromobutyl)-5-methoxy-1,2-benzisothiazol-3(2H)-one using the procedure described for Example 15, Step 5 there was obtained a white solid: $^1$H NMR (400 MHz, CDCl$_3$): 7.94 (d, J=8.6 Hz, 1H), 7.75 (d, J=7.6 Hz, 1H), 7.6 (t, 1H), 7.44 (d, J=7.6 Hz, 1H), 7.39–7.34 (m, 2H), 7.27–7.25 (m, 1H), 3.97 (s, 3H), 3.79 (t, J=7.3 Hz, 2H), 3.02 (s, 2H), 2.96 (m, 2H), 2.44 (br t, 2H), 2.14–2.0 (m, 4H), 1.89 (m, 2H), 1.65 (m, 2H), 1.38 (br d, 2H); mp (HCl salt) 229°–31° C.

EXAMPLE 61

1,1-Dioxido-2-(4-(spiro(1,3-dihydro-1-oxo-2H-indenyl-2,4'-piperidin-1'-yl)butyl)-5-methyl-1,2-benzisothiazol-3(2H)-one From 1,3-dihydro-1-oxo-spiro(2H-indenyl-2,4'-piperidine) and 1,1-dioxido-2-(4-bromobutyl)-5-methyl-1, 2-benzisothiazol-3(2H)-one using the procedure described for Example 15, Step 5 there was obtained a white solid: $^1$H NMR (300 MHz, CDCl$_3$): 7.86–7.76 (m, 3H), 7.68–7.58 (m, 2H), 7.46 (d, J=6.8 Hz, 1H), 7.39 (t, J=7.4 Hz, 1H), 3.83 (t, J=6.8 Hz, 2H), 3.03 (s, 2H), 2.98 (br d, J=10.6 Hz, 2H), 2.57 (s, 3H), 2.46 (t, J=7.4 Hz, 2H), 2.19–2.05 (m, 4H), 1.92 (m, 2H), 1.66 (m,2H), 1.40 (br d, 11.6 Hz, 2H); mp (HCl salt) 230°–1° C.

EXAMPLE 62

1,1-Dioxido-2-(4-(spiro(1,3-dihydro-1-oxo-2H-indenyl-2,4'-piperidin-1'-yl)butyl)-5-chloro-1,2-benzisothiazol-3(2H)-one From 1,3-dihydro-1-oxo-spiro(2H-indenyl-2,4'-piperidine) and 1,1-dioxido-2-(4-bromobutyl)-5-chloro-1,2-benzisothiazol-3(2H)-one using the procedure described for Example 15, Step 5 there was obtained a white solid: $^1$H NMR (400 MHz, CDCl$_3$): 8.02 (s, 1H), 7.87–7.80 (m, 2H), 7.75 (d, J=7.6 Hz, 1H), 7.59 (t, J=7.6 Hz, 1H), 7.44 (d, J=7 Hz, 1H), 7.37 (t, J=7.5 Hz, 1H), 3.82 (t, J=7.4 Hz, 2H), 3.02 (s, 2H), 2.95 (br d, J=11.5 Hz, 2H), 2.44 (t, 2H), 2.16–2.0 (m, 4H), 1.90 (m, 2H), 1.64 (m, 2H), 1.38 (br d, J=11.5 Hz, 2H); mp (HCl salt) 235°–7° C.

EXAMPLE 63

1,1-Dioxido-2-(4-(spiro(1,3-dihydro-1-oxo-2H-indene-2,4'-piperidin-1'-yl)butyl)-5-fluoro-1,2-benzisothiazol-3(2H)-one From 1,3-dihydro-1-oxo-spiro(2H-indenyl-2,4'-piperidine) and 1,1-dioxido-2-(4-bromobutyl)-5-fluoro-1,2-benzisothiazol-3(2H)-one using the procedure described for Example 15, Step 5 there was obtained a white solid: $^1$H NMR (400 MHz, CDCl$_3$): 7.93 (m, 1H), 7.76–7.71 (m, 2H), 7.61–7.45 (m, 2H), 7.44 (d, J=7.7 Hz, 1H), 7.37 (t, J=7.4 Hz, 1H), 3.82 (t, J=7.4 Hz, 2H), 3.02 (s, 2H), 2.97 (br d, J=11.5 Hz, 2H), 2.45 (t, J=7.4 Hz, 2H), 2.16 (m, 2H), 2.05 (m, 2H), 1.95–1.87 (m, 2H), 1.7–1.6 (m, 2H), 1.38 (br d, J=12.5 Hz, 2H); mp (HCl salt) 238°–40° C.

EXAMPLE 64

1,1-Dioxido-2-(4-(spiro(1,3-dihydro-1-oxo-2H-indenyl-2,4'-piperidin-1'-yl)butyl)-5-nitro-1,2-benzisothiazol-3(2H)-one From 1,3-dihydro-1-oxo-spiro(2H-indenyl-2,4'-piperidine) and 1,1-dioxido-2-(4-bromobutyl)-5-nitro-1,2-benzisothiazol-3(2H)-one using the procedure described for Example 15, Step 5 there was obtained a white solid:$^1$H NMR (400 MHz, CDCl$_3$): 8.84 (s, 1H), 8.70 (d, J=6.38 Hz, 1H), 8.11 (d, J=8.4 Hz, 1H), 7.73 (d, J=7.6 Hz, 1H), 7.56 (d, J=8.4 Hz, 1H), 7.43 (d, J=7.7 Hz, 1H), 7.35 (t, 1H), 3.86 (t, J=7.4 Hz, 2H), 3.00 (s, 2H), 2.95 (br d, 2H), 2.42 (t, J=7.4 Hz, 2H), 2.14 (m, 2H), 2.04 (m, 2H), 1.94 (m, 2H), 1.63 (m, 2H), 1.37 (br d, J=12.5 Hz, 2H); mp (HCl salt) 241°–3° C.

EXAMPLE 65

1,1-Dioxido-2-(4-(spiro(1,3-dihydro-1-oxo-2H-indenyl-2,4'-piperidin-1'-yl)butyl)-6-nitro-1,2-benzisothiazol-3(2H)-one From 1,3-dihydro-1-oxo-spiro(2H-indenyl-2,4'-piperidine) and 1,1-dioxido-2-(4-bromobutyl)-6-nitro-1,2-benzisothiazol-3(2H)-one using the procedure described for Example 15, Step 5 there was obtained a white solid: $^1$H NMR (300 MHz, CDCl$_3$): 8.75 (s, 1H), 8.68 (dd, J=2, 6.4 Hz, 1H), 8.26 (d, J=8.3 Hz, 1H), 7.75 (d, J=7.5 Hz, 1H), 7.59 (t, 1 H), 4.25 (br d, J=12.5 Hz, 2H), 3.88 (t, J=7.4 Hz, 2H), 3.02 (s, 2H), 2.96 (br d, 2H), 2.44 (t, J=7.4 Hz, 2H), 2.13–1.91 (m, 6H), 1.63 (m, 2H); mp (HCl salt) 231°–4° C.

EXAMPLE 66

1,1-Dioxido-2-(4-(spiro(1,3-dihydro-1-oxo-2H-indenyl-2,4'-piperidin-1'-yl)butyl)-isothiazolo[5,4-c]pyridin-3(2H)-one Step 1: A solution of 16 g of pyridine-3-sulfonyl chloride prepared as described by B. I. Alo, O. B. Familoni, F. Marsais and G. Queguiner, *J. Heterocyclic Chem.* 1992,29, 61–4 in 250 mL of chloroform was added to a solution of 8 g of 4-amino-1-butanol and 40 mL of triethylamine in 250 mL of chloroform at 0° C. The mixture was stirred overnight while warming to ambient temperature, the concentrated under reduced pressure to dryness. The residue was stirred with 500 mL of ethyl acetate, filtered and concentrated to dryness. To a solution of the crude N-(4-hydroxybutyl) pyridine-3-sulfonamide (28 g) in 200 mL of dichloromethane was added 30 mL of 3,4-dihydro-2H-pyran and 3 g of p-toluenesulfonic acid monohydrate. The reaction was stirred overnight, shaken with 100 mL of saturated sodium bicarbonate, dried over MgSO4, and concentrated to dryness. Chromatography of the residue over silica gel, eluting with ethyl acetate gave 20 g of N-(4-(2-tetrahydropyranyloxy)butyl)pyridine-3-sulfonamide as a thich amber oil.

Step 2: To a stirred solution of 54 mL of dry diisopropylamine in 200 mL of dry tetrahydrofuran cooled to −78° C. was added 205 mL of commercial 1.6M n-butyllithium in hexane keeping the temperature below −30° C. After aging for 30 min −30° C., the solution was cooled to −78° C. a solution of 23.3 g of N-(4-(2-tetrahydropyranyloxy)butyl) pyridine-3-sulfonamide in 150 mL of dry tetrahydrofuran was added dropwise keeping the internal temperature below −70° C. (ca. 30 min). The resulting solution was aged at −78° C. for 2.5 h and the deep red solution quenched by a stream of carbon dioxide gas with a fritted glass dispersion tube. During the addition, the color dissipated and the temperature rose to −40° C. After 15 min below −40° C., the bath was removed and the solution allowed to warm to room temprature over 1 h under a gentle stream of carbon dioxide. The mixture was partitioned between 400 mL of water and 500 mL of ether. The ether extracts contained unreacted N-(4-(2-tetrahydropyranyloxy)butyl) pyridine-3-sulfonamide. The aqueous layer was carefully acidified to pH=3 with concentrated HCl, and extracted with five 200 mL portions of chloroform. The combined organic extracts were dried over MgSO$_4$ and concentrated under reduced pressure. Drying under vacuum gave 19 g of N-(4-(2-tetrahydropyranyloxy)butyl) 4-carboxypyridine-3-sulfonamide as a amber solid.

Step 3: To a stirred solution of 19 g of N-(4-(2-tetrahydropyranyloxy)butyl) 4-carboxypyridine-3-sulfonamide and 16 mL of triethylamine in 300 mL of dichloromethane at 0° C. was added 6.5 mL of methyl chloroformnate dropwise. After 30 min, the mixture was shaken with 100 mL of saturated sodium bicarbonate, dried over MgSO$_4$ and concentrated under reduced pressure. Chromatography of the dark brown oil over silica gel, eluting with 1:1 ethyl acetate:hexane gave 16 g of homogeneous 1,1-dioxido-2-(4-(2-tetrahydropyranyloxy) butyl)-isothiazolo[5,4-c]pyridin-3(2H)-one as an amber oil.

Step 4: A solution of 1 g of 2-(4-(2-tetrahydropyranyloxy) butyl)-isothiazolo[5,4-c]pyridin-3(2H)-one and 0.1 g of p-toluenesulfonic acid monohydrate in 50 mL of methanol was stirred overnight at ambient temperature and concentrated to dryness under reduced pressure. The residue was dissolved in 200 mL of ethyl acetate, washed with 4 mL of saturated sodium bicarbonate, dried over MgSO4 and concentrated under reduced pressure. Drying under vacuum overnight gave 0.73 g (78%) of 2-(4-hydroxybutyl)-isothiazolo[5,4-c]pyridin-3(2H)-one as an oil: $^1$H NMR (400 MHz, CDCl$_3$): 9.28 (s, 1H), 9.15 (d, J=5 Hz, 1H), 7.98 (d, J=5Hz, 1H), 3.86 (t, J=7.5 Hz, 2H), 3.71 (t, J=6.4 Hz, 2H), 2.36 (br s, 1H), 1.98 (m, 2H), 1.27 (m, 2H).

Step 4: To a stirred solution of 0.73 g of 2-(4-hydroxybutyl)isothiazolo[5,4-c]pyridin-3(2H)-one and 0.8 mL of triethylamine in 50 mL of dry tetrahydrofuran at 0° C. was added 0.63 g of technical grade 4-nitrobenzenesulfonyl chloride. After 4 h, the solution was filtered and concentrated to dryness under reduced pressure. The residue was dissolved in 100 mL of ethyl acetate, washed with 10 mL of saturated sodium carbonate and dried over MgSO$_4$. Concentration under reduced pressure gave 1.4 g of crude 2-(4-(4-nitrobenzenesulfonyloxy)butyl)-isothiazolo[5,4-c] pyridin-3(2H)-one as an oil. The crude product was a mixture of 4-nitrobenzenesulfonate contaminated with a small amount of chloride by NMR, and was used in the next step without further purification.

Step 6: A mixture of 0.60 g of 1,3-dihydro-1-oxo-spiro (2H-indenyl-2,4'-piperidine) and 1.4 g of 1,1-dioxido-2-(4-(4-nitrobenzenesulfonyloxy)butyl)-isothiazolo[5,4-c] pyridin-3(2H)-one in 20 mL of anhydrous acetonitrile were allowed to stir overnight at ambient temperature then concentrated to dryness under reduced pressure. The solid mass was partitioned between 200 mL of ethyl acetate and 20 mnL of saturated sodium carbonate. The organic extract was dried over MgSO4 and concentrated under reduced pressure. Chromatography of the residue on silica gel, eluting with 10% methanol in ethyl acetate gave 0.5 g of a white solid: $^1$H NMR (400 MHz, CDCl$_3$): 9.26 (s, 1H), 9.15 (m, 1H), 7.95 (d, J=4.9 Hz, 1H), 7.75 (d, J=7.5 Hz, 1H), 7.59 (t, J=8.1 Hz, 1H), 7.44 (d, J=7.7 Hz, 1H), 3.85 (t, J=7.4 Hz, 2H), 3.02 (s, 2H), 2.95 (br d, J=12 Hz, 2H), 2.44 (t, J=7.4 Hz, 2H), 2.17–2.03 (m, 4H), 1.92 (m, 2H), 1.64 (m, 2H), 1.4 (br d, J=12 Hz, 2H); mp (HCl salt) 228°–30° C.

EXAMPLE 67

1,1-Dioxido-2-(4-(spiro(1,3-dihydro-1-oxo-2H-indenyl-2,4'-piperidin-1'-yl)butyl)-isothiazolo[5,4-b] pyridin-3(2H)-one Step 1: Chlorine gas was dispersed through a mixture of 4.3 g of methyl 2-mercaptonicotinate, prepared as described by L. Katz, W. Schroeder and M. Cohen, *J. Org. Chem.* 1954,19, 711–17, 10 mL of dichloromethane, 60 mL of glacial acetic acid and 150 mL of water at 0°–3° C. for 1.5 h. The resulting solution was extracted with four 200 mL portions of chloroform and the combined extracts dried over MgSO$_4$ and concentrated under reduced pressure in a fume hood. The oily methyl 2-chlorosulfonylnicotinate, 3.5 g, was dissolved in 20 mL of dichloromethane and added to a solution of 2 g of 4-amino-1-butanol and 3 mL of triethylamine in 200 mL of dichloromethane at 0° C. The mixture was stirred overnight while warming to ambient temperature, the decanted and the residue extracted with three 100 mL portions of dichloromethane. The combined extracts were concentrated under reduced pressure to dryness. To a solution of the resulting crude N-(4-hydroxybutyl) 3-methoxycarbonylpyridine-2-sulfonamide (5 g) in 100 mL of dichloromethane was added 10 mL of 3,4-dihydro-2H-pyran and 1 g of p-toluenesulfonic acid monohydrate. The reaction was stirred overnight, shaken with 50 mL of saturated sodium bicarbonate, dried over MgSO$_4$, and concentrated to dryness. To a stirred solution of the resulting crude N-(4-(2-tetrahydropyranyloxy)butyl) 3-methoxycarbonylpyridine-2-sulfonamide (7 g) in 100 mL of 100 mL of methanol and 30 mL of water was added 2 g of lithium hydroxide monohydrate. The reaction mixture was stirred overnight at ambient temperature, concentrated to dryness under reduced pressure to remove methanol, acidified to pH=3 with concentrated HCl and extracted with five 50 mL portions of chloroform. The combined extracts were dried over MgSO4 and concentrated to dryness. The residue, N-(4-(2-tetrahydropyranyloxy)butyl) 3-carboxycarbonylpyridine-2-sulfonamide weighed 5 g and was used without further purification.

Step 2: To a stirred solution of 3 g of N-(4-(2-tetrahydropyranyloxy)butyl) 3-carboxycarbonylpyridine-2-sulfonamide and 2.3 mL of triethylamine in 100 mL of dichloromethane at 0° C. was added 0.8 mL of methyl chloroformate dropwise. After 2 h, the mixture was shaken with 10 mL of saturated sodium bicarbonate, dried over MgSO$_4$ and concentrated under reduced pressure. Chromatography of the dark brown oil over silica gel, eluting with 1:1 ethyl acetate: hexane gave 3 g of homogeneous 1,1-dioxido-2-(4-(2-tetrahydropyranyloxy)butyl)-isothiazolo[5,4-b]pyridin-3(2H)-one as an amber oil.

Step 3: A solution of 1 g of 2-(4-(2-tetrahydropyranyloxy)butyl)-isothiazolo[5,4-blpyridin-3(2H)-one and 0.1 g of p-toluenesulfonic acid monohydrate in 50 mL of methanol was stirred overnight at ambient temperature and concentrated to dryness under reduced pressure. The residue was dissolved in 200 mL of ethyl acetate, washed with 4 mL of saturated sodium bicarbonate, dried over MgSO4 and concentrated under reduced pressure. Drying under vacuum overnight gave 0.73 g of 1,1-dioxido-2-(4-hydroxybutyl) isothiazolo[5,4-b]pyridin-3(2H)-one as an oil: 1H NMR (400 MHz, CDCl$_3$): 9.00 (d, J=1.5 Hz, 1H), 8.40 (d, J=7.7 Hz, 1H), 7.80 (dd, J=1.5 , 7.7 Hz, 1H), 3.86 (t, J=7.5 Hz, 2H), 3.71 (t, J=6.4 Hz, 2H), 2.31 (br s, 1H), 1.98 (m, 2H), 1.26 (m, 2H).

Step 4: To a stirred solution of 0.73 g of 1,1-dioxido-2-(4-hydroxybutyl)-isothiazolo[5,4-b]pyridin-3(2H)-one and 0.8 mL of triethylamine in 50 mL of dry tetrahydrofuran at 0° C. was added 0.63 g of technical grade 4-nitrobenzenesulfonyl chloride. After 4 h, the solution was filtered and concentrated to dryness under reduced pressure. The residue was dissolved in 100 mL of ethyl acetate, washed with 10 mL of saturated sodium carbonate and dried over MgSO$_4$. Concentration under reduced pressure gave 1.4 g of crude 1,1-dioxido-2-(4-(4-nitrobenzenesulfonyloxy)butyl)-isothiazolo[5,4-b]pyridin-3 (2H)-one as an oil. The crude product was a mixture of 4-nitrobenzenesulfonate contaminated with a small amount of chloride by NMR, and was used in the next step without further purification.

Step 5: A mixture of 0.60 g of 1,3-dihydro-1-oxo-spiro (2H-indenyl-2,4'-piperidine) and 1.4 g of 1,1-dioxido-2-(4-(4-nitrobenzenesulfonyloxy)butyl)-isothiazolo[5,4-b] pyridin-3(2H)-one in 20 mL of anhydrous acetonitrile were allowed to stir overnight at ambient temperature then concentrated to dryness under reduced pressure. The solid mass was partitioned between 200 mL of ethyl acetate and 20 mL of saturated sodium carbonate. The organic extract was dried over MgSO4 and concentrated under reduced pressure. Chromatography of the residue on silica gel, eluting with 10% methanol in ethyl acetate gave 0.5 g of a white solid: $^1$H NMR (400 MHz, CDCl$_3$): 9.00(d, J=4.8 Hz, 1H), 8.38 (d, J=7.7 Hz, 1H), 7.81–7.74 (m, 2H), 7.59 (t, J=7.4 Hz, 1H), 7.45 (d, J=7 Hz, 1H), 7.37 (t, J=7.4 Hz, 1H), 3.87 (t, J=7.23 Hz, 1H), 3.02 (s, 2H), 2.97 (br d, J=11.35 Hz, 2H), 2.46 (t, J=7.33 Hz, 2H), 2.20–2.03 (m, 4H), 2.07–2.20 (m, 2H), 1.97–1.90 (m, 2H), 1.70–1.61 (m, 2H), 1.61 (br d, J=12.08 Hz, 2H).

EXAMPLE 68

1,1-Dioxido-2-(4-(4-(6-methyl-2-oxo-3-benzoxazolinyl)-piperidin-1-yl)-butyl)-5-nitro-1,2-benzisothiazol-3(2H)-one From 4-(6-methyl-2-oxo-3-benzoxazolinyl)-piperidine and 2-(4-bromobutyl)-1,1-dioxido-5-nitro-1,2-benzisothiazol-3(2H)-one using the procedure described for Example 15, Step 5 there was obtained a white solid:1H NMR, HCl salt, (400 MHz, CDCl$_3$): 8.87 (d, J=2.0 Hz, 1H), 8.74 (d, J=2.18 Hz, 1H), 8.72 (d, J=1.8 Hz, 1H), 8.14 (d, J=8.4 Hz, 1H), 7.11 (d, J=6.54 Hz, 1H), 7.03 (s, 1H), 6.94 (d, J=8.06 Hz, 1H), 4.18 (m, 1H), 3.89 (t, J=7.39 Hz, 2H), 3.06 (d, J=10.07 Hz, 2H), 2.46 (m, 2H), 2.38 (s, 3H), 2.34 (m, 2H), 2.14 (t, J=11.5 Hz, 2H), 1.94 (m, 2H), 1.85 (d, J=11.4 Hz, 2H), 1.65 (m, 2H).

EXAMPLE 69

2-(4-(Spiro(1,3-dihydro-1-oxo-2H-indenyl-2,4'-piperidin-1'-yl)butyl)-pyrrolo[3,4b]pyridin-5,7(1H)-dione From 1,3-dihydro-1-oxo-spiro(2H-indenyl-2,4'-piperidine) and 2-(4-bromobutyl)-pyrrolo[3,4b]pyridin-5,7(1H)-dione using the procedure described for Example 15, Step 5 there was obtained a white solid: $^1$H NMR, (400 MHz, CDCl$_3$): 9.15 (s, 1H), 9.06 (s, 1H), 9.06 (d, J=4.76 Hz, 1H), 7.75 (d, J=4.76 Hz, 1H), 7.59 (t, J=7.42 Hz, 1H), 7.44 (d, J=8.0 Hz, 1H), 7.37 (t, J=7.33 Hz, 1H), 3.76 (t, J=7.14 Hz, 2H), 3.02 (s, 2H), 2.41 (br t, J=7.33 Hz, 2H), 2.12–1.99 (m, 4H), 1.77–1.72 (m, 2H), 1.56 (br m, 2H), 1.38 (m, 2H).

EXAMPLE 70

1,1-Dioxido-2,3-dihydro-2-(4-(spiro[2H-indenyl-2,4'-piperidine-1(3H)-one]-1'-yl)-butyl)-naphth[1,8-de]isothiazin-3-one From 1,3-dihydro-1-oxo-spiro(2H-indenyl-2,4'-piperidine) and 2-(4-bromobutyl)-1,1-dioxido-2,3-dihydronaphth[1,8-de]isothiazin-3-one using the procedure described for Example 15, Step 5 there was obtained a white solid: $^1$H NMR (300 MHz, CDCl$_3$): 8.37 (d, J=7.92 Hz, 1H), 8.26 (d, 1H), 8.08 (m, 2H), 7.86–7.74 (m, 3H), 7.58 (t, 1H), 7.44 (d, J=7.7 Hz, 1H), 7.38 (t, 1H), 3.90 (t, J=7.3 Hz, 2H), 3.02 (s, 2H), 2.98 (br d, 2H), 2.46 (t, J=7.4 Hz, 2H), 2.14–1.94 (m, 6H), 1.69 (m, 2H), 1.40 (br d, 2H); mp (HCl salt) 248°–50° C.

EXAMPLE 71

2-(4-Bromobutyl)-1,1-dioxido-4-methoxy-1,2-benzothiazol-3(2H)-one

The general procedure of J. D. Commerford and H. B. Donahue *J. Org. Chem.* 1956,21, 583–4 was modified: A mixture of 0.5 g of 3,3-dioxido-4-methoxy-1,2-benzothiazol-3(2H)-one prepared as described by D. J. Hlasta, J. J. Court and R. C. Desai, *Tetrahedron Lett.* 1991, 32, 7179–82, 1 mL of N,N-dimethylformamide and 0.1 g of sodium hydride 60% oil dispersion was stirred at ambient temperature for 15 min, and 1.4 mL of 1,4-dibromobutane was added. After stirring at ambient temperature overnight, the mixture was diluted with 25 mL of ethyl acetate, washed with 25 mL of sat'd NaHCO$_3$, 25 mL of sat'd brine and dried over MgSO$_4$. Removal of solvents under reduced pressure and vacuum distillation gave a crude product as a viscous oil which was free of 1,4-dibromobutane by $^1$H-NMR and was used without further purification.

EXAMPLE 72

2-(4-Bromobutyl)-1,1-dioxido-6-methoxy-1,2-benzothiazol-3(2H)-one

The general procedure of J. D. Commerford and H. B. Donahue *J. Org. Chem.* 1956, 21, 583–4 was modified: A mixture of 0.5 g of 3,3-dioxido-6-methoxy-1,2-benzothiazol-3(2H)-one prepared from N,N-diethyl-4-methoxybenzamide using the general procedure described by D. J. Hlasta, J. J. Court and R. C. Desai, *Tetrahedron Lett.* 1991, 32, 7179–82, 1 mL of N,N-dimethylformamide and 0.1 g of sodium hydride 60% oil dispersion was stirred at ambient temperature for 15 min, and 1.4 mL of 1,4-dibromobutane was added. After stirring at ambient temperature overnight, the mixture was diluted with 25 mL of ethyl acetate, washed with 25 mL of sat'd NaHCO$_3$, 25 mL of sat'd brine and dried over MgSO$_4$. Removal of solvents under reduced pressure and vacuum distillation gave a crude product as a viscous oil which was free of 1,4-dibromobutane by $^1$H-NMR and was used without further purification.

EXAMPLE 73

2-(4-Bromobutyl)-1,1-dioxido-7-methoxy-1,2-benzothiazol-3(2H)-one

The general procedure of J. D. Commerford and H. B. Donahue *J. Org. Chem.* 1956,21, 583–4 was modified: A mixture of 0.5 g of 3,3-dioxido-7-methoxy-1,2-benzothiazol-3(2H)-one prepared from N,N-diethyl-3-methoxybenzamide using the general procedure described by D. J. Hlasta, J. J. Court and R. C. Desai, *Tetrahedron Lett.* 1991, 32, 7179–82, 1 mL of N,N-dimethylformamide and 0.1 g of sodium hydride 60% oil dispersion was stirred at ambient temperature for 15 min, and 1.4 mL of 1,4-dibromobutane was added. After stirring at ambient temperature overnight, the mixture was diluted with 25 mL of ethyl acetate, washed with 25 mL of sat'd NaHCO$_3$, 25 mL of sat'd brine and dried over MgSO$_4$. Removal of solvents under reduced pressure and vacuum distillation gave a crude product as a viscous oil which was free of 1,4-dibromobutane by $^1$H-NMR and was used without further purification.

EXAMPLE 74

2-(4-Bromobutyl)-1,1-dioxido-5-methyl-1,2-benzothiazol-3(2H)-one

The general procedure of J. D. Commerford and H. B. Donahue *J. Org. Chem.* 1956,21, 583–4 was modified: A mixture of 0.5 g of 3,3-dioxido-5-methyl-1,2-benzothiazol-3(2H)-one prepared as described by J. G. Lombardino, *J. Org. Chem.* 1971, 36, 1843–5, 1 mL of N,N-dimethylformamide and 0.1 g of sodium hydride 60% oil dispersion was stirred at ambient temperature for 15 min, and 1.4 mL of 1,4-dibromobutane was added. After stirring at ambient temperature overnight, the mixture was diluted with 25 mL of ethyl acetate, washed with 25 mL of sat'd NaHCO$_3$, 25 mL of sat'd brine and dried over MgSO$_4$. Removal of solvents under reduced pressure and vacuum distillation gave a crude product as a viscous oil which was free of 1,4-dibromobutane by $^1$H-NMR and was used without further purification.

EXAMPLE 75

2-(4-Bromobutyl)-1,1-dioxido-5-fluoro-1,2-benzothiazol-3(2H)-one

The general procedure of J. D. Commerford and H. B. Donahue *J. Org. Chem.* 1956, 21, 583–4 was modified: A mixture of 0.5 g of 3,3-dioxido-5-fluoro-1,2-benzothiazol-3(2H)-one prepared as described by J. G. Lombardino, *J. Org. Chem.* 1971, 36, 1843–5, 1 mL of N,N-dimethylformamide and 0.1 g of sodium hydride 60% oil dispersion was stirred at ambient temperature for 15 min, and 1.4 mL of 1,4-dibromobutane was added. After stirring at ambient temperature overnight, the mixture was diluted with 25 mL of ethyl acetate, washed with 25 mL of sat'd NaHCO$_3$, 25 mL of sat'd brine and dried over MgSO$_4$. Removal of solvents under reduced pressure and vacuum distillation gave a crude product as a viscous oil which was free of 1,4-dibromobutane by $^1$H-NMR and was used without further purification.

EXAMPLE 76

2-(4-Bromobutyl)-1,1-dioxido-5-chloro-1,2-benzothiazol-3(2H)-one

The general procedure of J. D. Commerford and H. B. Donahue *J. Org. Chem.* 1956, 21, 583–4 was modified: A mixture of 0.5 g of 3,3-dioxido-5-chloro-1,2-benzothiazol-3 (2H)-one prepared as described by J. G. Lombardino, *J. Org. Chem.* 1971, 36, 1843–5, 1 mL of N,N-dimethylformamide and 0.1 g of sodium hydride 60% oil dispersion was stirred at ambient temperature for 15 min, and 1.4 mL of 1,4-dibromobutane was added. After stirring at ambient temperature overnight, the mixture was diluted with 25 ml of ethyl acetate, washed with 25 mL of sat'd NaHCO$_3$, 25 mL of sat'd brine and dried over MgSO$_4$. Removal of solvents under reduced pressure and vacuum distillation gave a crude product as a viscous oil which was free of 1,4-dibromobutane by $^1$H-NMR and was used without further purification.

EXAMPLE 77

2-(4-Bromobutyl)-1,1-dioxido-6-nitro-1,2-benzothiazol-3(2H)-one

The general procedure of J. D. Commerford and H. B. Donahue *J. Org. Chem.* 1956, 21, 583–4 was modified: A stirred mixture of 1.0 g of 3,3-dioxido-6-nitro-1,2-benzothiazol-3(2H)-one prepared as described by H. Kamogawa, S. Yamamoto and M. Nanasawa, *Bull. Chem. Soc. Japan*, 1982, 55, 3824–7, and 6 mL of 1N NaOH was warmed to dissolution and allowed to cool to ambient temperature for 15 min. The mixture was concentrated to dryness under reduced pressure and the white solid azeotropically dried with 20 nL of toluene. The resulting sodium salt was dissolved in 3 mL of N,N-dimethylformamide and 2.6 mL of 1,4-dibromobutane was added.

After stirring at ambient temperature overnight, the mixture was diluted with 25 mL of ethyl acetate, washed with 25 mL of sat'd NaHCO$_3$, 25 mL of sat'd brine and dried over MgSO$_4$. Removal of solvents under reduced pressure and vacuum distillation gave a crude product as a solid which was free of 1,4-dibromobutane by $^1$H-NMR and was used without further purification.

EXAMPLE 78

2-(4-Bromobutyl)-1,1-dioxido-2,3-dihydronaphth[1,8-de]isothiazin-3-one

The general procedure of J. D. Commerford and H. B. Donahue *J. Org. Chem.* 1956, 21, 583–4 was modified: A mixture of 0.5 g of 1,1-dioxido-2,3-dihydronaphth[1,8-de] isothiazin-3-one prepared as described by J. G. Lombardino, *J. Org. Chem.* 1971, 36, 1843–5, 1 mL of N,N-dimethylformamide and 0.1 g of sodium hydride 60% oil dispersion was stirred at ambient temperature for 15 min, and 1.4 mL of 1,4-dibromobutane was added. After stirring at ambient temperature overnight, the mixture was diluted with 25 mL of ethyl acetate, washed with 25 mL of sat'd NaHCO$_3$, 25 mL of sat'd brine and dried over MgSO$_4$. Removal of solvents under reduced pressure and vacuum distillation gave a crude product as a viscous oil which was free of 1,4-dibromobutane by $^1$H-NMR and was used without further purification.

EXAMPLE 79

2-(4-Bromobutyl)-3,3-dioxido-1,2-dehydronaphth[1,2-d]isothiazol-1-one

The general procedure of J. D. Commerford and H. B. Donahue *J. Org. Chem.* 1956, 21, 583–4 was modified: A mixture of 0.5 g of 3,3-dioxido-1,2-dehydronaphth[1,2-d] isothiazol-1-one prepared as described by J. G. Lombardino, *J. Org. Chem.* 1971, 36, 1843–5, 1 mL of N,N-dimethylformamide and 0.1 g of sodium hydride 60% oil dispersion was stirred at ambient temperature for 15 min, and 1.4 TnL of 1,4-dibromobutane was added. After stirring at ambient temperature overnight, the mixture was diluted with 25 mL of ethyl acetate, washed with 25 mL of sat'd NaHCO$_3$, 25 mL of sat'd brine and dried over MgSO$_4$. Removal of solvents under reduced pressure and vacuum distillation gave a crude product as a viscous oil which was free of 1,4-dibromobutane by $^1$H-NMR and was used without further purification.

EXAMPLE 80

2-(4-Bromobutyl)-pyrrolo[3,4b]pyridin-5,7(1H)-dione

The general procedure of J. D. Commerford and H. B. Donahue *J. Org. Chem.* 1956,21, 583–4 was modified: A mixture of 0.5 g of commercial pyrrolo[3,4b]pyridin-5,7 (1H)-dione (Aldrich Chemical Co.), 1 mL of N,N-dimethylformamide and 0.1 g of sodium hydride 60% oil dispersion was stirred at ambient temperature for 15 min, and 1.4 mL of 1,4-dibromobutane was added. After stirring at ambient temperature overnight, the mixture was diluted with 25 ml of ethyl acetate, washed with 25 mL of sat'd NaHCO$_3$, 25 mL of sat'd brine and dried over MgSO$_4$. Removal of solvents under reduced pressure and vacuum distillation gave a crude product as a viscous oil which was free of 1,4-dibromobutane by $^1$H-NMR and was used without further purification.

EXAMPLE 81

1,1-Dioxido-2-(4-(spiro[3-oxo-phthalan-1,4'-piperidin-1'-yl)butyl)-1,2-benzisothiazol-3(2H)-one From spiro[phthalan-1,4'-piperidine]-3-one, prepared as described in U.S. Pat. No. 3,686,186, and 2-(4-bromobutyl) -1,1-dioxido-1,2-benzothiazol-3(2H)-one using the procedure described for Example 15, Step 5 there was obtained a white solid: mp 226°–8° C.

EXAMPLE 82

5-chloro-1-(4-piperidinyl)-3-benzoxazolin-2-one

From the reaction of 2-amino-4-chlorophenol and N-t-butyloxycarbonyl-4-piperidone according to Example 15 Steps 2–4 was obtained a white solid.

EXAMPLE 83

4-(3a-(R)-8a-(S)-2-oxo-3,3a,8,8a-tetrahydro-2H-indeno[1,2-d]oxazolinyl)-piperidine From the reaction of (–)-1(S)-amino-2(R)-hydroxyindan, prepared according to W. J. Thompson et. al. *J. Med. Chem.* 1992, 35, 1685–1701, and N-t-butyloxycarbonyl-4-piperidone according to Example 15 Steps 2–4 was obtained a white solid.

EXAMPLE 84

4-(2-oxonaphth[2,3-d]oxazolinyl)-piperidine

From the reaction of 3-amino-2-naphthol and N-t-butyloxycarbonyl-4-piperidone according to Example 15 Steps 2–4 was obtained a white solid.

EXAMPLE 85

4-(6-methyl-2-oxo-3-benzoxazolinyl)-piperidine

From the reaction of 6-amino-m-cresol and N-t-butyloxycarbonyl-4-piperidone according to Example 15 Steps 2–4 was obtained a white solid.

EXAMPLE 86

4-(2-oxo-5-phenyl-3-benzoxazolinyl)-piperidine

From the reaction of 2-amino-4-phenylphenol and N-t-butyloxycarbonyl-4-piperidone according to Example 15 Steps 2–4 was obtained a white solid.

EXAMPLE 87

4-(6-methoxy-2-oxo-3-benzoxazolinyl)-piperidine

From the reaction of 2-amino-5-methoxyphenol and N-t-butyloxycarbonyl-4-piperidone according to Example 15 Steps 2–4 was obtained a white solid.

EXAMPLE 88

4-(6-carbomethoxy-2-oxo-3-benzoxazolinyl)-piperidine

From the reaction of methyl 4-amino-3-hydroxybenzoate and N-t-butyloxycarbonyl-4-piperidone according to Example 15 Steps 2–4 was obtained a white solid.

EXAMPLE 89

4-(5-ethylsulfonyl-2-oxo-3-benzoxazolinyl)-piperidine

From the reaction of 2-amino-4-(ethylsulfonyl)phenol and N-t-butyloxycarbonyl-4-piperidone according to Example 15 Steps 2–4 was obtained a white solid.

EXAMPLE 90

4-(2-oxo-3-oxazolo[4,5-b]pyridyl)-piperidine

From the reaction of 2-amino-3-hydroxypyridine and N-t-butyloxycarbonyl-4-piperidone according to Example 15 Steps 2–4 was obtained a white solid.

EXAMPLE 91

4-(7-carbethoxy-2-oxo-3-benzoxazolinyl)-piperidine

From the reaction of methyl 3-amino-2-hydroxybenzoate and N-t-butyloxycarbonyl-4-piperidone according to Example 15 Steps 2–4 was obtained a white solid.

EXAMPLE 92

4-(5-tert-butyl-2-oxo-3-benzoxazolinyl)-piperidine

From the reaction of 2-amino-4-tert-butylphenol and N-t-butyloxycarbonyl-4-piperidone according to Example 15 Steps 2–4 was obtained a white solid.

EXAMPLE 93

4-(5,7-dimethyl-2-oxo-3-benzoxazolinyl)-piperidine

From the reaction of 6-amino-2,4-dimethylphenol and N-t-butyloxycarbonyl-4-piperidone according to Example 15 Steps 2–4 was obtained a white solid.

EXAMPLE 94

1,1-Dioxido-2-(4-(4-(1,3-dihydro-2-oxo-2H-benzimidazolin-1-yl)-piperidin-1-yl)-butyl)-1,2-benzisothiazol-3(2H)-one From 1,3-dihydro-1-(4-piperidinyl)-2H-benzimidazol-2-one and 2-(4-bromobutyl)-1,1-dioxido-1,2-benzisothiazol-3 (2H)-one using the procedure described for Example 15, Step 5 there was obtained a white solid: mp 193°–5° C.; Analysis calculated for $C_{23}H_{26}N_4O_4S$•0.5 $CHCl_3$ C: 54.89 H: 5.19, N: 10.90 found C: 54.60, H: 5.24, N: 10.84. $^1H$ NMR (300 MHz, $CDCl_3$) 10.0 (s, 1H), 8.2 (d, 1H), 8.1–7.9 (m, 3H), 7.4 (dd, 1H), 7.25 (m, 1H), 7.18 (m, 3H), 4.5 (m, 1H), 3.95 (t, 2H), 3.2 (d, J=12 Hz, 2H), 2.6 (m, 4H), 2.3 (t, J 12 Hz, 2H), 2.1 (m, 4H), 1.95 (m, 2H), 1.8(m, 2H).

EXAMPLE 95

1,1-Dioxido-2-(4-(4-(1,3-dihydro-2-oxo-3-methyl-2H-benzimidazolin-1-yl)-piperidin-1-yl)-butyl)-1,2-benzisothiazol-3(2H)-one Step 1: A mixture of 1 g of 1,3-dihydro-1-(4-piperidinyl)-2H-benzimidazol-2-one, 25 mL of tetrahydrofuran, 10 mL of saturated $Na_2CO_3$, 20 mL of water and 1.05 g of di-tert-butyl-dicarbonate was stirred for 6 h. The mixture was extracted with 100 mL of chloroform and the organic extracts concentrated to dryness under reduced pressure. Drying under vacuum gave 1.6 g of 1,3-dihydro-1-(1-tert-butyloxycarbonylpiperidin-4-yl)-2H-benzimidazol-2-one as a white crystalline solid.

Step 2: A mixture of 0.060 g of sodium hydride, 60% oil dispersion, 10 mL of DMF, 0.086 mL of iodomethane, and 0.4 g of 1,3-dihydro-1-(1-tert-butyloxycarbonylpiperidin-4-yl)-2H-benzimidazol-2-one was stirred for 12 h, then partitioned between 100 mL of chloroform and 50 mL of water. The chloroform extracts dried over $MgSO_4$, and concentrated under reduced pressure. Trituration with hexane gave 0.38 g of 1,3-dihydro-1-(1-tert-butyloxycarbonylpiperidin-4-yl)-3-methyl-2H-benzimidazol-2-one as a crystalline solid: $^1H$ NMR (300 MHz, $CDCl_3$) 7.13–7.03 (m, 3H), 6.98 (d, 1H), 4.5 (m, 1H), 4.3 (br m, 2H), 3.4 (s, 3H), 2.85 (m, 4H), 2.3 (m, 2H), 1.8 (d, 2H), 1.5 (s, 91H).

Step 3: A stream of hydrogen chloride gas was dispersed through a stirred, ice cold solution of 0.383 g of 1,3-dihydro-1-(1-tert-butyloxycarbonylpiperidin-4-yl)-3-methyl-2H-benzimidazol-2-one in 500 mL of ethyl acetate for 30 min. Stirring was continued at 0° C. for 1 h, then at ambient temperature for 1 h. The suspension was partitioned between 250 mL of chloroform and 50 mL of saturated $Na_2CO_3$. Drying under reduced pressure gave 0.296 of 1,3-dihydro-1-(4-piperidinyl)-2H-benzimidazol-2-one as an off-white solid.

Step 4: From 1,3-dihydro-1-(4-piperidinyl)-3-methyl-2H-benzimidazol-2-one and 2-(4-bromobutyl)-1,1-dioxido-1,2-benzothiazol-3(2H)-one using the procedure described for Example 15, Step 5 there was obtained a white solid: mp 161°–163° C. Analysis calculated for $C_{24}H_{28}N_4O_4S$ C: 61.52, H: 6.02, N: 11.96 found C: 61.44, H: 6.06, N: 11.84. $^1H$ NMR (300 MHz, $CDCl_3$) 8.2 (d, 1H), 8.1–7.9 (m, 3H), 7.13–7.03 (m, 3H), 6.98 (d, 1H), 4.5 (m, 1H), 3.95 (t, 2H), 3.4 (s, 3H), 3.2 (d, J=12 Hz, 2H), 2.6 (m, 4H), 2.3 (t, J=12 Hz, 2H), 2.1 (m, 4H), 1.95 (m, 2H), 1.8(m, 2H).

EXAMPLE 96

1,1-Dioxido-2-(4-(4-(1,3-dihydro-2-oxo-5-methyl-2H-benzimidazolin-1-yl)-piperidin-1-yl)-butyl)-1,2-benzisothiazol-3(2H)-one Step 1: A mixture of 69 g of 4-chloro-3-nitro-toluene, 50 g of ethyl 4-amino-1-piperidinecarboxylate, 24 g of sodium carbonate, 0.1 g of sodium iodide and 120 ml of cyclohexanol was heated to 150° C. for 72 h. After cooling the cyclohexanol was distilled off under reduced pressure and the residue partitioned between 1 L of ethyl acetate and 1 L of water. The organic extract was dried over $MgSO_4$ and concentrated under reduced pressure. Chromatography over silica gel, eluting with 20% ethyl acetate in cyclohexane gave 38.5 g (42.3%) of ethyl 4-(4-methyl-2-nitroanilino)-1-piperidinecarboxylate as an orange crystalline solid. $^1$H NMR (400 MHz, $CDCl_3$) 8.0 (s, 1H), 7.27 (t, J=9 Hz, 1H), 6.8 (d, J=9 Hz, 1H), 4.15 (q, J=7 Hz, 2H), 4.05 (br m, 2H), 3.67 (br m, 1H), 3.10 (br t, J=11 Hz, 2H), 2.27 (s, 3H), 2.06 (br d, J=11 Hz, 2H), 1.6 (m, 2H), 1.27 (t, J=7 Hz, 4H).

Step 2: A mixture of 8.23 g of ethyl 4-(4-methyl-2-nitroanilino)-1-piperidinecarboxylate, 200 mL of tetrahydrofuran , 225 mL of ethanol and 2 g of 5% platinum on carbon was stirred under an atmosphere of hydrogen for 7 h. The catalyst was filtered off and the filtrate concentrated to to a thick oil. To an ice cold, vigorously stirred solution of the resulting crude ethyl 4-(4-methyl-2-aminoanilino)-1-piperidinecarboxylate in 500 mL of ethyl acetate was added 500 mL of saturated sodium carbonate followed by 20 mL of 1.9M phosgene in toluene dropwise over 30 min. After stirring overnight at room temperature, the layers were separated and the organic layer dried over $MgSO_4$ and concentrated to dryness. Trituration of the residue with ether-hexane gave 8 g of ethyl 4-(5-methyl-2-oxo-1-benzimidazolinyl)piperidine-1-carboxylate as a white crystalline solid.

Step 3: A mixture of 5 g of ethyl 4-(5-methyl-2-oxo-1-benzimidazolinyl)piperidine-1-carboxylate and 20 mL of 2N NaOH was heated under reflux for 12 h. The resulting solution is cooled and stirred for for 30 minutes with 5 g of ammonium chloride and extracted with three 200 mL portions of chloroform. The combined organic extracts were dried over $MgSO_4$, concentrated under reduced pressure and triturated with ether. The solid product 1,3-dihydro-1-(4-piperidinyl)-5-methyl-2H-benzimidazol-2-one weighed 3.5 g after drying.

Step 4: From 1,3-dihydro-1-(4-piperidinyl)-5-methyl-2H-benzimidazol-2-one and 2-(4-bromobutyl)-1,1-dioxido-1,2-benzothiazol-3(2H)-one using the procedure described for Example 15, Step 5 there was obtained a white solid: mp 104°–6° C.; Analysis calculated for $C_{24}H_{28}N_4O_4S \cdot 0.35$ $CH_3OH \cdot 0.35$ $CH_2Cl_2$ C: 58.22, H: 5.95, N: 11.00 found C: 58.43, H: 5.91, N: 10.60.

EXAMPLE 97

1,1-Dioxido-2-(4-(4-(1,3-dihydro-2-oxo-4-methyl-2H-benzimidazolin-1-yl)-piperidin-1-yl)-butyl)-1,2-benzisothiazol-3(2H)-one From 1,3-dihydro-1-(4-piperidinyl)-4-methyl-2H-benzimidazol-2-one and 2-(4-bromobutyl)-1,1-dioxido-1,2-benzothiazol-3(2H)-one using the procedure described for Example 15, Step 5 there was obtained a white solid: mp 90°–2° C.; Analysis calculated for $C_{24}H_{28}N_4O_4S \cdot 0.5$ $CH_2Cl_2$ C: 57.58, H: 5.72, N: 10.96 found C: 57.41, H: 5.74, N: 10.96.

EXAMPLE 98

1,1-Dioxido-2-(4-(4-(1,3-dihydro-2-oxo-5-methoxy-2H-benzimidazolin-1-yl)-piperidin-1-yl)-butyl)-1,2-benzisothiazol-3(2H)-one From 4-chloro-3-nitro-anisole using the procedures described for Example 96, Steps 1 through 4, there was obtained a white solid: mp 162°–4° C.; Analysis calculated for $C_{24}H_{28}N_4O_5S \cdot 0.5$ $CH_3OH$ C: 58.78, H: 6.04, N: 11.19 found C: 58.99, H: 5.88, N: 10.87.

EXAMPLE 99

1,1-Dioxido-2-(4-(4-(1,3-dihydro-2-oxo-5-chloro-2H-benzimidazolin-1-yl)-piperidin-1-yl)-butyl)-1,2-benzisothiazol-3(2H)-one From 2,5-dichloronitrobenzene using the procedures described for Example 96, Steps 1 through 4, there was obtained a white solid: mp 206°–8° C.; Analysis calculated for $C_{23}H_{25}ClN_4O_4S \cdot 0.8$ $CH_2Cl_2$ C: 54.46, H: 5.11, N: 10.68 found C: 54.34, H: 4.87, N: 10.81.

EXAMPLE 100

1,1-Dioxido-2-(4-(4-(1,3-dihydro-2-oxo-5-fluoro-2H-benzimidazolin-1-yl)-piperidin-1-yl)-butyl)-5-chloro-1,2-benzisothiazol-3(2H)-one From 2-chloro-5-fluoronitrobenzene using the procedures described for Example 96, Steps 1 through 4, and 2-(4-bromobutyl)-1,1-dioxido-5-chloro-1,2-benzisothiazol-3(2H)-one there was obtained a white solid: mp 259°–61 ° C.; Analysis calculated for $C_{23}H_{24}FClN_4O_4S \cdot HCl$ C: 50.83, H: 4.64, N: 10.31 found C: 50.74, H: 4.60, N: 10.18.

EXAMPLE 101

1,1-Dioxido-2-(4-(4-(1,3-dihydro-2-oxo-5-methyl-2H-benzimidazolin-1-yl)-piperidin-1-yl)-butyl)-5-chloro-1,2-benzisothiazol-3(2H)-one From 1,3-dihydro-1-(4-piperidinyl)-5-methyl-2H-benzimidazol-2-one and 2-(4-bromobutyl)-1,1-dioxido-5-chloro-1,2-benzisothiazol-3(2H)-one using the procedure described for Example 15, Step 5 there was obtained a white solid: mp 258°–60° C.; Analysis calculated for $C_{23}H_{27}ClN_4O_4S \cdot HCl \cdot 0.4$ $H_2O$ C: 52.72, H: 5.31, N: 10.25 found C: 52.75, H: 5.23, N: 10.25.

EXAMPLE 102

1,1-Dioxido-2-(4-(4-(1,3-dihydro-2-oxo-6-methyl-2H-benzimidazolin-1-yl)-piperidin-1-yl)-butyl)-5-chloro-1,2-benzisothiazol-3(2H)-one From 1,3-dihydro-1-(4-piperidinyl)-5-methyl-2H-benzimidazol-2-one and 2-(4-bromobutyl)-1,1-dioxido-5-chloro-1,2-benzisothiazol-3(2H)-one using the procedure described for Example 15, Step 5 there was obtained a white solid: mp 273°–75° C.; Analysis calculated for $C_{23}H_{27}ClN_4O_4S \cdot HCl \cdot 0.5$ $H_2O$ C: 52.55, H: 5.33, N: 10.22 found C: 52.52, H: 5.05, N: 10.16.

EXAMPLE 103

1,1-Dioxido-2-(4-(4-(5-methyl-2-oxo-3-benzoxazolinyl)-piperidin-1-yl)-butyl)-5,6-dihydro-[1,4]dioxino[2,3-e]benzisothiazol-3(2H)-one From 4-(5-methyl-2-oxo-3-benzoxazolinyl)-piperidine and 2-(4-hydroxybutyl)-1,1-dioxido-5,6-dihydro-[1,4]

dioxino[2,3-d]benzisothiazol-3(2H)-one using the procedure described for Example 66. Steps 4–6 there was obtained a white solid: mp 98°–101° C. Analysis calculated for $C_{26}H_{29}N_3O_7S \cdot 0.3$ CHCl$_3$ C: 56.06, H: 5.24, N: 7.46 found C: 56.11, H: 5.30, N: 7.45. $^1$H NMR (300 MHz, CDCl$_3$) 7.4 (d, H), 7.27 (d, 1H), 7.18 (d, 1H), 7.05 (s, 1H), 6.95 (d, 1H), 4.5 (m, 2H), 4.4 (m, 2H), 4.2 (m, 1H), 3.8 (t, 2H), 3.08 (d, 2H), 2.44 (t, 2H), 2.39 (s, 3H), 2.1 (t, 2H), 1.85 (m, 4H), 1.71 (m, 2H), 1.65 (m, 2H).

EXAMPLE 104

1,1-Dioxido-2-(4-(4-(2-oxo-3-benzoxazolinyl)-piperidin-1-yl)-butyl)-5,6-dihydro-[1,4]dioxino[2,3-e]benzisothiazol-3(2H)-one From 4-(2-oxo-3-benzoxazolinyl)-piperidine and 2-(4-hydroxybutyl)-1,1-dioxido-5,6-dihydro-[1,4]dioxino[2,3-d]benzisothiazol-3(2H)-one using the procedure described for Example 66, Steps 4–6 there was obtained a white solid: mp 79°–82° C. $^1$H NMR (400 MHz, CDCl$_3$) 7.4 (d, 1H), 7.3 (m, 2H), 7.2–7.0 (br m, 3H), 4.5 (m, 2H), 4.4 (m, 2H), 4.2 (m, 1H), 3.8 (m, 2H), 3.1 (br d, 2H), 2.5–2.4 (br m, 2H), 2.2 (m, 2H), 2.0–1.85 (br m, 4H), 1.80 (m, 2H), 1.7 (m, 2H) Analysis calculated for $C_{25}H_{27}N_3O_7S \cdot 0.3$ CHCl$_3$ C: 55.31, H: 5.01, N: 7.65 found C: 55.20, H: 5.08, N: 7.39.

EXAMPLE 105

1,1-Dioxido-2-(4-(4-(spiro-1,3-dihydro-1-oxo-2H-indenyl)-2,4'-piperidin-1'-yl)-butyl)-5,6-dihydro-[1,4]dioxino[2,3-e]benzisothiazol-3(2H)-one From 1,3-dihydro-1-oxo-spiro(2H-indenyl-2,4'-piperidine) and 2-(4-hydroxybutyl)-1,1-dioxido-5,6-dihydro-[1,4]dioxino[2,3-d]benzisothiazol-3(2H)-one using the procedure described for Example 66, Steps 4–6 there was obtained a white solid: Analysis calculated for $C_{26}H_{29.8}N_2O_6S \cdot 0.4$ CHCl$_3$ C: 58.25, H: 5.26, N: 5.15 found C: 58.36, H: 5.40, N: 5.20.

EXAMPLE 106

1,1-Dioxido-2-(4-(4-(1,3-dihydro-2-oxo-1H-3,4-dihydroquinazolin-1-yl)-piperidin-1-yl)-butyl)-1,2-benzisothiazol-3(2H)-one Step 1: A mixture of 45 g of 2-aminomethylaniline, 60 g of di-tert-butyldicarbonate, 1000 mL of dichloromethane was stirred for 18 h and washed with 500 mL of 2N NaOH. The organic extract was dried over MgSO$_4$ and concentrated under reduced pressure. Drying under vacuum gave 47 g of 2-(tert-butoxycarbonylaminomethyl)aniline as a white crystalline solid. $^1$H NMR (400 MHz, CDCl$_3$) 7.1 (t, 1H), 7.05 (d, 1H), 6.65 (dd, 2H), 4.8 (br s, 1H), 4.2 (br m, 4H), 1.44 (s, 9H).

Step 2: A mixture of 15.5 g of 2-(tert-butoxycarbonyl aminomethyl)aniline, 15 g of N-t-butyloxycarbonyl-4-piperidone, 250 mL of 1,2-dichloroethane, 4.2 mL of glacial acetic acid and 25 g of sodium triacetoxyborohydride was stirred at room temperature for 48 h. The reaction mixture was poured into 500 mL chloroform and 500 mL saturated aqueous Na$_2$CO$_3$ and the layers separated. The aqueous layer was extracted with 2×250 mL of chloroform and the combined organic layers dried over MgSO$_4$ and concentrated under reduced pressure. Drying overnight under vacuum gave 30.1 g of tert-butyl (2-(tert-butoxycarbonyl aminomethyl)anilino)piperidine carboxylate as a solid: $^1$H NMR (400 MHz, CDCl$_3$) 7.19 (t, 1H), 7.0 (d, 1H), 6.6 (dd, 2H), 4.94 (br s, 1H), 4.75 (br s, 1H), 4.23 (br m, 2H), 4.0 (br m, 2H), 3.45 (br m, 1H), 3.0 (br m, 2H), 2.0 (br m, 2H), 1.82 (br m, 1H), 1.46 (s, 9H), 1.44 (s, 9H).

Step 3: To a stirred solution of 27.1 g of tert-butyl 4-(2-tert-butoxycarbonylaminomethylanilino)-1-piperidinecarboxylate and 30 mL of triethylamine in 400 mL of dichloromethane was added dropwise 60 mL of a 1.93M solution of phosgene in toluene. After stirring for 12 h, 200 mL of 1N NaOH was added. The mixture was shaken, and the organic layer separated, dried over MgSO$_4$ and concentrated under reduced pressure. Chromatography on silica gel, eluting with 25% ethyl acetate in hexane gave, after drying overnight under vacuum, 25 g of 1,3-dihydro-1-[1-tert-butoxycarbonylpiperidin-4-yl]-3-tert-butoxycarbonyl-1H-3,4-dihydroquinazolin-2-one carboxylate as a clear glass: $^1$H NMR (400 MHz, CDCl$_3$) 7.52 (d, 1H), 7.45 (t, 1H), 7.36 (m, 1H), 7.10 (d, 1H), 4.2–4.0 (br m, 5H), 3.65–3.25 (br m, 2H), 2.75 (br m, 2H), 2.28 (br d, 1H), 1.8 (br d, 1H), 1.5 (s, 9H), 1.49 (s, 9H).

Step 4: A stirred solution of 25 g of 1,3-dihydro-1-[1-tert-butoxycarbonylpiperidin-4-yl]-3-tert -butoxycarbonyl-1H-3,4-dihydroquinazolin-2-one carboxylate in 1 L of ethyl acetate cooled to −50° C. was saturated with hydrogen chloride gas for 15 min. The resulting mixture was allowed to warm to room temperature and stir for 4 h. The white solid precipitate was collected by filtration. Drying under vacuum gave 13.1 of 1,3-dihydro-1-[piperidin-4-yl]-3-tert-butoxycarbonyl-1H-3,4-dihydroquinazolin-2-one hydrochloride salt as a white solid. The salt (0.8 g) was converted to the free base by partitioning between chloroform and saturated sodium carbonate. Drying under vacuum gave 0.68 g of 1,3-dihydro-1-[piperidin-4-yl]-1H-3,4-dihydroquinazolin-2-one as a white solid: $^1$H NMR (400 MHz, CDCl$_3$) 7.25 (dd, 1H), 7.12 (d, 1H), 7.06 (d, 1H), 6.98 (t, 1H), 5.2 (br s, 1H), 4.28 (s, 2H), 4.10 (m, 1H), 3.22 (d, 2H), 2.73 (m, 2H), 2.59 (m, 2H), 2.05 (br s, 1H), 1.82 (br d, 2H).

Step 5:

From 1,3-dihydro-1-[piperidin-4-yl] -1 H-3,4-dihydroquinazolin-2-one and 2-(4-bromobutyl)-1,1-dioxido-1,2-benzothiazol-3(2H)-one using the procedure described for Example 15, Step 5 there was obtained a white solid: Analysis calculated for $C_{24}H_{28}N_4O_4S \cdot 0.35$ CHCl$_3 \cdot 0.45$ H$_2$O C: 52.70 H: 5.49, N: 10.10 found C: 52.71, H: 5.49, N: 10.33.

EXAMPLE 107

2-(4-Hydroxybutyl)-1,1-dioxido-5,6-dihydro-[1,4]dioxino[2,3-d]benzisothiazol-3(2H)-one Step 1: To a stirred solution of 12 g of 1,4-benzodioxane in 40 mL of chloroform cooled to −10° C. under calcium sulfate drying tube was added dropwise over 15 min, 6 mL of chlorosulfonic acid. The mixture was allowed to warm to 20C over 15 min, poured onto 400 mL of ice and extracted into 1 L of chloroform. Drying over MgSO$_4$ and concentration under reduced pressure gave 21.5 g of 1,4-benzodioxane-6-sulfonylchloride as a white crystalline solid.

Step 2: To an ice cold, stirred solution of 10 g of 4-aminobutanol and 25 mL of triethylamine in 250 mL of dichloromethane was added a solution of 21.5 g of 1,4-benzodioxane-6-sulfonylchloride in 100 mL of chloroform over 30 min. The mixture was allowed to warm and stir overnight, washed with 100 mL of 6N HCl and dried over MgSO$_4$. To this solution was added 300 mL of dichloromethane, 20 mL of dihydropyran and 100 mg of p-toluenesulfonic acid monohydrate. After stirring for 12 h, the mixture was washed with 100 mL of saturated $Na_2CO_3$, dried over $MgSO_4$ and concentrated under reduced pressure. Chromatography on silica gel, eluting with 30% ethyl acetate in hexane gave, after drying overnight under vacuum, 13 g of N-(4-(2-tetrahydropyranyloxy)butyl)-1,4-benzodioxane-6-sulfonamide as a resin.

Step 3: To a stirred solution of 13 g of N-(4-(2-tetrahydropyranyloxy)butyl)-1,4-benzodioxane-6-sulfonamide in 250 mL of dry tetrahydrofuran cooled to −78° C. was added 50 mL of commercial 1.6M n-butyllithium in hexane over 10 min. After aging for 60 min with warming to 0° C., the solution was cooled to −78° C. and quenched by a stream of carbon dioxide gas with a fritted glass dispersion tube, keepiing the temperature below −40° C. for 30 min. The solution was allowed to warm to room temprature over 1 h and partitioned between 200 mL of water, 200 mL of saturated $Na_2CO_3$ and 3×200 mL of ether. The aqueous layer was carefully acidified to pH=3 with concentrated HCl, and extracted with 3×200 mL portions of ether. The combined organic extracts were dried over $MgSO_4$ and concentrated under reduced pressure. Drying under vacuum gave 10.1 g of N-(4-(2-tetrahydropyranyloxy)butyl) 5-carboxy-1,4-benzodioxane-6-sulfonamide as a foam.

Step 4: To a stirred solution of 10 g of N-(4-(2-tetrahydropyranyloxy)butyl)-carboxy-1,4-benzodioxane-6-sulfonamide and 7 mL of triethylamine in 200 mL of dichloromethane cooled to 0° C. was added 2 mL of methyl chloroformate dropwise. After 3 h at 20° C., the mixture was shaken with 50 mL of saturated sodium carbonate, dried over $MgSO_4$ and concentrated under reduced pressure. The residue was disolved in 200 mL of methanol containing 1 g of p-toluenesulfonic acid monohydrate, stirred overnight at ambient temperature, and concentrated to dryness under reduced pressure. The residue was dissolved in 200 mL of ethyl acetate, washed with 5 mL of saturated sodium carbonate, dried over $MgSO4$ and concentrated under reduced pressure. Trituration with ether gave 4 g of 2-(4-hydroxybutyl)-1,1-dioxido-5,6-dihydro-[1,4]dioxino[2,3-d]benzisothiazol-3(2H)-one as a white crystalline solid: mp °C.; $^1H$ NMR (400 MHz, $CDCl_3$): 7.4 (d, 1H), 7.25 (d, 1H), 4.5 (m, 2H), 4.4 (m, 2H), 3.8 (t, 2H), 3.7 (t, 2H), 1.95 (m, 2H), 1.7 (m, 2H), 1.55 (br s, 1H).

EXAMPLES 108

2-(4-Hydroxybutyl)-1,1-dioxido-5-ethoxy-1,2-benzothiazol-3(2H)-one

From ethoxybenzene using the procedures described for Example 107, Steps 1–4 there was obtained a thick oil.

EXAMPLE 109

2-(4-Hydroxybutyl)-1,1-dioxido-5-ethyl-1,2-benzothiazol-3(2H)-one

From 4-ethylbenzenesulfonylchloride using the procedures described for Example 107, Steps 2–4 there was obtained a thick oil.

EXAMPLE 110

2-(4-Hydroxybutyl)-1,1-dioxido-5-isopropyl-1,2-benzothiazol-3(2H)-one

From 4-isopropylbenzenesulfonylchloride using the procedures described for Example 107, Steps 2–4 there was obtained a thick oil.

EXAMPLE 111

1,1-Dioxido-2-(4-(4-(2-oxo-3-benzoxazolinyl)-piperidin-1-yl)-butyl)-5-ethoxy-1,2-benzothiazol-3(2H)-one From 4-(2-oxo-3-benzoxazolinyl)-piperidine and 2-(4-hydroxybutyl)-1,1-dioxido-5-ethoxy-1,2-benzothiazol-3(2H)-one using the procedure described for Example 66, Steps 4–6 there was obtained a white solid: $^1H$ NMR (400 MHz, $CDCl_3$) 7.79 (d, J=8.57 Hz, 1H), 7.44 (s, 1H), 7.29–7.26 (m, 2H), 7.21 (d, J=6.89 Hz, 1H), 7.16–7.06 (m, 2H), 4.24–4.11 (m, 1H), 3.81 (t, J=7.3 Hz, 2H), 3.06 (br d, J=11.76 Hz, 2H), 2.45 (t, J=7.39 Hz, 2H), 2.36 (m, 2H), 2.11 (bt, J=11.08 Hz, 2H), 1.93–1.80 (br m, 6H), 1.65 (br m, 2H), 1.48 (t, J=6.97, 3H) Analysis calculated for $C_{25}H_{30}N_3O_6S \cdot HCl \cdot 1.2\ H_2O$ C: 53.75, H: 6.03, N: 7.52 found C: 53.72, H: 5.65 N: 7.52.

EXAMPLE 112

1,1-Dioxido-2-(4-(4-(spiro-1,3-dihydro-1-oxo-2H-indenyl)-2,4'-piperidin-1'-yl)-butyl)-5-ethoxy-1,2-benzothiazol-3(2H)-one From 1,3-dihydro-1-oxo-spiro(2H-indenyl-2,4'-piperidine) and 2-(4-hydroxybutyl)-1,1-dioxido-5-ethoxy-1,2-benzothiazol-3(2H)-one using the procedure described for Example 66, Steps 4–6 there was obtained a white solid: Analysis calculated for $C_{26}H_{30}N_2O_5S \cdot HCl \cdot 0.45\ H_2O\ 0.3\ CHCl_3$ C: 56.11, H: 5.77, N: 4.98 found C: 56.14, H: 5.74, N: 5.18.

EXAMPLE 113

1,1-Dioxido-2-(4-(4-(spiro-1,3-dihydro-1-oxo-2H-indenyl)-2,4'-piperidin-1'-yl)-butyl)-5-ethyl-1,2-benzothiazol-3(2H)-one From 1,3-dihydro-1-oxo-spiro(2H-indenyl-2,4'-piperidine) and 2-(4-hydroxybutyl)-1,1-dioxido-5-ethyl-1,2-benzothiazol-3(2H)-one using the procedure described for Example 66, Steps 4–6 there was obtained a white solid: Analysis calculated for $C_{26}H_{30}N_2O_4S \cdot HCl \cdot 0.2\ CHCl_3$ C: 59.71, H: 5.97, N: 5.32 found C: 59.66, H: 6.16, N: 5.35.

EXAMPLE 114

1,1-Dioxido-2-(4-(4-(2-oxo-3-benzoxazolinyl)-piperidin-1-yl)-butyl)-5-ethyl-1,2-benzothiazol-3(2H)-one From 4-(2-oxo-3-benzoxazolinyl)-piperidine and 2-(4-hydroxybutyl)-1,1-dioxido-5-ethyl-1,2-benzothiazol-3(2H)-one using the procedure described for Example 66, Steps 4–6 there was obtained a white solid: mp 165°–168 ° C. $^1H$ NMR (400 MHz, $CDCl_3$) 7.9 (s, 1H), 7.8 (m, 1H), 7.66 (m, 1H), 7.3 (m, 1H), 7.2–7.05 (m, 3H), 4.2 (m, 1H), 3.8 (m, 2H), 3.1 (m, 2H), 2.82 (m, 2H), 2.4 (m, 2H), 2.1 (m, 2H), 2.0–1.8 (br m, 4H), 1.8–1.6 (br m, 4H), 1.3 (t, 3H) Analysis calculated for $C_{25}H_{30}N_3O_6S \cdot HCl \cdot 1.4\ H_2O$ C: 55.66, H: 6.06, N: 7.01 found C: 55.82, H: 5.81, N: 6.91.

EXAMPLE 115

1,1-Dioxido-2-(4-(4-(spiro-1,3-dihydro-1-oxo-2H-indenyl)-2,4'-piperidin-1'-yl)-butyl)-5-(2-propyl)-1,2-benzothiazol-3(2H)-one From 1,3-dihydro-1-oxo-spiro(2H-indenyl-2,4'-piperidine) and 2-(4-hydroxybutyl)-1,1-dioxido-5-(2- propyl)-1,2-benzothiazol-3(2H)-one using the procedure described for Example 66, Steps 4–6 there was obtained a white solid: Analysis calculated for $C_{27}H_{32}N_2O_4S \cdot HCl \cdot 1.00$ $H_2O$ C: 60.60, H: 6.59, N: 5.24 found C: 60.62, H: 6.36, N: 5.28.

EXAMPLE 116

1,1-Dioxido-2-(4-(4-(2-oxo-3-benzoxazolinyl)-piperidin-1-yl)-butyl)-5-(2-propyl)-1,2-benzothiazol-3(2H)-one From 4-(2-oxo-3-benzoxazolinyl)-piperidine and 2-(4-hydroxybutyl)-1,1-dioxido-5-(2-propyl)-1,2-benzothiazol-3(2H)-one using the procedure described for Example 66, Steps 4–6 there was obtained a white solid: $^1$H NMR (400 MHz, CDCl$_3$) 7.9 (s, 1H), 7.8 (d, 1H), 7.7 (d, 1H), 7.3 (m, 1H), 7.2–7.0 (br m, 3H), 4.2 (m, 1H), 3.8 (m, 2H), 3.1 (m, 3H), 2.7–2.5 (br m, 2H), 2.1 (m, 2H), 2.0–1.8 (br m, 4H), 1.7–1.6 (m, 4H), 1.35 (d, 6H) Analysis calculated for $C_{25}H_{30}N_3O_6S \cdot HCl \cdot 1.6\ CH_3CO_2CH_2CH_3C$: 57.64, H: 6.69, N: 6.23 found C: 57.06, H: 6.12, N: 6.56.

The following Examples 117–144 were made in the same manner as described in detail above using readily available starting materials.

EXAMPLE 117

1,1-Dioxido-2-(4-(4-(2-oxo-3-benzoxazolinyl)-piperidin-1-yl)-butyl)-6-nitro-1,2-benzisothiazol-3(2H)-one $^1$H NMR (400 MHz, CDCl$_3$) 8.78 (d, J=1.46 Hz, 1H), 8.70 (dd, J=8.39 Hz, 2.01 Hz, 1H), 8.29 (dd, J=8.39 Hz, 0.4 Hz, 1H), 7.26–7.08 (m, 4H), 4.21 (dt, J=12.43 Hz, 4.2 Hz, 1H), 3.91 (t, J=7.40 Hz, 2H), 3.08 (d, J=11.58 Hz, 2H), 2.47 (t, J=7.22 Hz, 2H), 2.39 (dq, J=12.43 Hz, 3.80 Hz, 2H), 2.12 (t, J=10.24 Hz, 2H), 1.95 (q, J=7.56 Hz, 2H), 1.87 (dd, J=11.92 Hz, 2.01 Hz, 2H), 1.65 (q, J=7.89 Hz, 2H).

EXAMPLE 118

1,1-Dioxido-2-(4-(4-(2-oxo-3-benzoxazolinyl)-piperidin-1-yl)-butyl)-5-fluoro-1,2-benzisothiazol-3(2H)-one $^1$H NMR (400 MHz, CDCl$_3$) 7.95 (dd, J=4.37 Hz, 4.20 Hz, 1H), 7.73 (dd, J=7.05 Hz, 2.35 Hz, 1H), 7.56 (dt, J=8.39 Hz, 2.52 Hz, 1H), 7.25 (s, 1H), 7.20 (d, J=7.89 Hz, 1H), 7.14 (dt, J=7.55 Hz, 1.18 Hz, 1H), 7.09 (dq, J=7.72 Hz, 1.18 Hz, 1H), 4.22 (tt, J=12.42 Hz, 4.2 Hz, 1H), 3.84 (t, J=7.39 Hz, 2H), 3.07 (d, J=11.75 Hz, 2H), 2.45 (t, J=7.22 Hz, 2H), 2.38 (dq, J=8.70 Hz, 3.90 Hz, 2H), 2.12 (dt, J=11.75 Hz, 1.51 Hz, 2H), 1.82–1.60 (m, 4H), 1.64 (q, J=7.56 Hz, 2H).

EXAMPLE 119

1,1-Dioxido-2-(4-(4-(2-oxo-3-benzoxazolinyl)-piperidin-1-yl)-butyl)-5-methyl-1,2-benzisothiazol-3(2H)-one $^1$H NMR (400 MHz, CDCl$_3$) 7.86 (s, 1H), 7.81 (d, J=7.89 Hz, 1H), 7.66 (d, J=8.06 Hz, 1H), 7.21 (d, J=7.55 Hz, 1H), 7.15 (t, J=6.21 Hz, 1.51 Hz, 7H), 4.2 (m, 1H), 3.83 (t, J=7.39 Hz, 2H), 3.08 (d, J=11.75 Hz, 2H), 2.56 (s, 3H), 2.45 (t, J=6.88 Hz, 2H), 2.37 (dt, J=8.22 Hz, 3.86 Hz, 2H), 2.11 (t, J=12.26 Hz, 2H), 1.94H–1.85 (r, 4H), 1.63 (m, 2H).

EXAMPLE 120

1,1-Dioxido-2-(4-(4-(2-oxo-3-benzoxazolinyl)-piperidin-1-yl)-butyl)-5-bromo-1,2-benzisothiazol-3(2H)-one mp 158°–162° C. $^1$H NMR (400 MHz, CDCl$_3$) 8.20 (m, 1H), 7.99 (dd, 1H), 7.79 (d, 1H), 7.22–7.06 (m, 4H), 4.21 (m, 2H), 3.83 (t, 2H), 3.07 (d, 2H), 2.55 (t, 2H), 2.42–2.30 (m, 2H), 2.10 (t, 2H), 1.94–1.82 (m, 4H), 1.61 (m, 2H).

EXAMPLE 121

1,1-Dioxido-2-(4-(4-(2-oxo-3-benzoxazolinyl)-piperidin-1-yl)-butyl)-5-trifluoromethyl-1,2-benzisothiazol-3(2H)-one mp 177°–179 ° C. $^1$H NMR (400 MHz, CDCl$_3$) 8.38 (s, 1H), 8.18 (d, 1H), 8.10 (d, 1H), 7.25 (m, 1H), 7.2 (d, 1H), 7.1–7.2 (m, 2H), 4.2 (m, 2H), 3.88 (m, 2H), 3.05 (br d, 2H), 2.45 (m, 2H), 2.4 (m, 2H), 2.1 (m, 2H), 1.82–2.0 (br m, 4H), 1.75–1.6 (m, 2H).

EXAMPLE 122

1,1-Dioxido-2-(4-(4-(2-oxo-3-benzoxazolinyl)-piperidin-1-yl)-butyl)-5-trifluoromethoxy-1,2-benzisothiazol-3(2H)-one mp 230°–233 ° C. $^1$H NMR (400 MHz, CDCl$_3$) 8.0 (d, 1H), 7.9 (s, 1H), 7.68 (d, 1H), 7.25 (d, 1H), 7.20 (d, 1H), 7.1–7.19 (m, 2H), 4.2 (m, 1H), 3.83 (m, 2H), 3.05 (br d, 2H), 2.42 (m, 2H), 2.4 (m, 2H), 2.1 (m, 2H), 2.8–1.8 (br m, 4H), 1.6 (m, 2H).

EXAMPLE 123

1,1-Dioxido-2-(4-(4-(2-oxo-1-naphth[1,2-d]oxazolinyl)-piperidin-1-yl)-butyl)-1,2-benzisothiazol-3(2H)-one $^1$H NMR (400 MHz, CD$_3$OD) 7.46 (d, J=8.61 Hz, 1H), 7.24 (dd, J=6.77, 0.73 Hz, 1H), 7.21 (d, J=7.32 Hz, 1H), 7.16–7.09 (m, 3H), 6.90 (d, J=8.79 Hz, 1H), 6.79 (t, J=7.30 Hz, 1H), 6.66 (t, J=7.51 Hz, 1H), 6.64 (d, J=8.79 Hz, 1H), 4.35 (m, 1H), 3.03 (t, J=6.22 Hz, 2H), 2.89 (d, J=12.63 Hz, 2H), 2.63 (q, J=6.96 Hz, 1H), 2.53 (br t, J=12.45 Hz, 1H), 2.41 (br m, 2H), 2.17 (br m, 2H), 1.48 (br d, J=13.55 Hz, 2H), 1.10(br m, 4H).

EXAMPLE 124

1,1-Dioxido-2-(4-(4-(5,6,7,8-tetrahydro-2-oxo-3-naphth[2,3-d]oxazolinyl)-piperidin-1-yl)-butyl)-1,2-benzisothiazol-3(2H)-one $^1$H NMR (300 MHz, CD$_3$OD) 8.09 (m, 2H), 7.98 (m, 2H), 7.08 (s, 1H), 6.93 (s, 1H), 3.87 (m, 2H), 3.74 (d, J=12.21 Hz, 2H), 3.24 (br m, 4H), 2.79 (br m, 6H), 2.13 (br d, J=13.54 Hz, 2H), 1.95 (br d, J=3.47 Hz, 4H), 1.89 (s, 4H).

EXAMPLE 125

1,1-Dioxido-2-(4-(4-(5-methyl-2-oxo-3-benzoxazolinyl)-piperidin-1-yl)-butyl)-1,2-benzisothiazol-3(2H)-one $^1$H NMR (400 MHz, CDCl$_3$) 8.08 (d, J=7.05 Hz, 1H), 7.95–7.85 (m, 4H), 7.06 (d, J=8.23 Hz, 1H), 6.92 (d, J=8.22 Hz, 1H), 4.58 (br t, J=11.92 Hz, 1H), 3.86 (t, J=6.55 Hz, 2H), 3.72 (d, J=10.58 Hz, 2H), 3.34 (q, J=11.25 Hz, 2H), 3.13 (br m, 2H), 2.93 (br m, 2H), 2.45 (s, 3H), 2.11–1.99 (m, 6H).

EXAMPLE 126

1,1-Dioxido-2-(4-(4-(5-carbomethoxy-2-oxo-3-benzoxazolinyl)-piperidin-1-yl)-butyl)-1,2-benzisothiazol-3(2H)-one $^1$H NMR (400 MHz, CDCl$_3$) 8.63 (s, 1H), 8.09 (d, J=7.05 Hz, 1H),7.96–7.86 (m, 5H), 4.61 (br t, J=13.09 Hz, 1H), 4.00

(s, 3H), 3.87 (t, J=6.72 Hz, 2H), 3.75 (d, J=10.91, 2H), 3.41 (q, J=12.26, 2H), 3.13 (m, 2H), 2.93 (m, 2H), 2.13–2.00 (m, 6H).

EXAMPLE 127

1,1-Dioxido-2-(4-(4-(6-fluoro-2-oxo-3-benzoxazolinyl)-piperidin-1-yl)-butyl)-1,2-benzisothiazol-3(2H)-one mp 154°–155 ° C. $^1$H NMR (400 MHz, CDCl$_3$) 8.06 (dd, 1H), 7.96–7.82 (m, 3H), 7.18 (br q, 1H), 6.99 (dd, 1H), 6.88 (td, 1H), 4.19 (m, 1H), 3.84 (t, 2H), 3.06 (d, 2H), 2.44 (t, 2H), 2.40–2.25 (m, 2H), 2.10 (t, 2H), 1.96–1.81 (m, 4H), 1.61 (bs, 2H).

EXAMPLE 128

1,1-Dioxido-2-(4-(4-(4-methyl-2-oxo-3-benzoxazolinyl)-piperidin-1-yl)-butyl)-1,2-benzisothiazol-3(2H)-one $^1$H NMR (400 MHz, CDCl$_3$) 8.07 (dd, J=6.72, 1.52 Hz, 1H), 7.93 (d, J=6.55 Hz, 1H), 7.85 (m, 2H), 7.03 (d, J=7.05 Hz, 1H), 6.97 (t, J=7.72 Hz, 1H), 6.89 (d, J=7.72 Hz, 1H), 4.21 (dt, J=8.23, 3.86 Hz, 1H), 3.86 (t, J=7.21 Hz, 2H), 3.09 (d, J=11.92 Hz, 2H), 2.71 (dq, J=8.72, 3.7 Hz, 2H), 2.55 (s, 3H), 2.43 (t, J=7.56 Hz, 2H), 2.03 (t, J=12.08 Hz, 2H), 1.91 (m, 2H), 1.65 (d, J=7.72 Hz, 2H), 1.63–1.59 (m, 2H).

EXAMPLE 129

1,1-Dioxido-2-(4-(4-(4-methoxy-2-oxo-3-benzoxazolinyl)-piperidin-1-yl)-butyl)-1,2-benzisothiazol-3(2H)-one $^1$H NMR (400 MHz, CDCl$_3$) 8.07 (dd, J=5.37, 1.01 Hz, 1H), 7.94–7.82 (m, 3H), 7.04 (t, J=8.22 Hz, 1H), 6.85 (dd, J=7.21, 0.84 Hz, 1H), 6.73 (d, J=8.56 Hz, 1H), 4.45 (tt, J=12.25, 4.2 Hz, 1H), 3.94 (s, 3H), 3.84 (t, J=7.39 Hz, 2H), 3.04 (br d, J=11.58 Hz, 2H), 2.54 (qd, J=8.73, 3.69 Hz, 2H), 2.43 (t, J=7.22, 2H), 2.07 (dt, J=10.24, 1.68 Hz, 2H), 1.93 (m, 2H), 1.77 (br d, J=9.74 Hz, 2H), 1.63 (m, 2H).

EXAMPLE 130

5-Chloro-1,1-dioxido-2-(4-(4-(6-methyl-2-oxo-3-benzoxazolinyl)-piperidin-1-yl)-butyl)-1,2-benzisothiazol-3(2H)-one $^1$H NMR (400 MHz, CDCl$_3$) 8.04 (d, J=1.68 Hz, 1H), 7.85 (overlapping t and dt, 2H), 7.13 (d, J=8.05 Hz, 1H), 7.04 (s, 1H), 6.95 (d, J=8.05 Hz, 1H), 4.19 (dt, J=12.42, 4.02 Hz, 1H), 3.84 (t, J=7.39 Hz, 2H), 3.07 (d, J=11.59 Hz, 2H), 2.45 (t, J=7.39 Hz, 2H), 2.38 (s, 3H), 2.33 (dq, J=12.25, 3.52 Hz, 2H), 2.11 (t, J=11.58 Hz, 2H), 1.95–1.84 (m, 4H), 1.63 (m, 2H).

EXAMPLE 131

5-Methylthio-1,1-dioxido-2-(4-(4-(6-methyl-2-oxo-3-benzoxazolinyl)-piperidin-1-yl)-butyl)-1,2-benzisothiazol-3(2H)-one $^1$H NMR (400 MHz, CDCl$_3$) 7.78 (t, J=1.68 Hz, 1H), 7.75 (s, 1H), 7.62 (dd, J=8.23, 1.85 Hz, 1H), 7.15 (br d, J=7.39 Hz, 1H), 7.02 (s, 1H), 6.94 (d, J=8.06 Hz, 1H), 4.19 (m, 1H), 3.82 (t, J=7.22 Hz, 2H), 3.08 (br d, J=9.56 Hz, 2H), 2.60 (s, 3H), 2.46 (br m, 2H), 2.37 (s, 3H), 2.42–2.37 (br m, 2H), 2.15–2.11 (br m, 2H), 1.94–1.83 (br m, 4H), 1.66–1.64 (br m, 2H).

EXAMPLE 132

5-Ethoxy-1,1-dioxido-2-(4-(4-(6-methyl-2-oxo-3-benzoxazolinyl)-piperidin-1-yl)-butyl)-1,2-benzisothiazol-3(2H)-one $^1$H NMR (400 MHz, CDCl$_3$) 7.79 (dd, J=8.56, 3.53 Hz, 1H), 7.44 (dd, J=4.36, 2.35 Hz, 1H), 7.29 (m, 1H), 7.14 (d, J=8.06 Hz, 1H), 7.02 (s, 1H), 6.94 (br d, J=7.22 Hz, 1H), 4.18 (m, 3H), 3.81 (t, J=7.38 Hz, 2H), 3.71 (t, J=6.38 Hz, 1H), 3.06 (d, J=11.75 Hz, 2H), 2.44 (t, J=7.38 Hz, 2H), 2.37 (s, 3H), 2.31 (dt, J=12.26, 3.53 Hz, 1H), 2.10 (dt, J=11.92, 2.02 Hz, 2H), 1.97–1.82 (m, 4H), 1.73–1.61 (m, 2H), 1.48 (dt, J=7.06, 1.18 Hz, 3H).

EXAMPLE 133

5-Chloro-1,1-dioxido-2-(4-(4-(6-fluoro-2-oxo-3-benzoxazolinyl)-piperidin-1-yl)-butyl)-1,2-benzisothiazol-3(2H)-one mp 155°–156 ° C. $^1$H NMR (400 MHz, CDCl$_3$) 8.04 (dd, 1H), 7.89–7.82 (m, 2H), 7.18 (q, 1H), 7.00 (dd, 1H), 6.89 (td, 1H), 4.19 (m, 1H), 3.82 (t, 2H), 3.07 (d, 2H), 2.45 (t, 2H), 2.40–2.27 (m, 2H), 2.11 (td, 2H), 1.97–1.82 (m, 4H), 1.64 (m, 2H).

EXAMPLE 134

4-Methyl-1,1-dioxido-2-(4-(4-(2-oxo-3-benzoxazolinyl)-piperidin-1-yl)-butyl)-1,2-benzisothiazol-3(2H)-one mp 137°–138 ° C. $^1$H NMR (400 MHz, CDCl$_3$) 7.78–7.69 (m, 2H), 7.58 (d, J=7.5 Hz, 1H), 7.27 (d, J=4.7 Hz, 11H), 7.20 (dd, J=6.9 Hz, 1.4 Hz, 1H), 7.17–7.06 (m, 2H), 4.21 (m, 1H), 3.81 (t, J=14.8 Hz, 2H), 3.07 (d, J=11.6 Hz, 2H), 2.79 (s, 3H), 2.46 (t, J=14.8 Hz, 2H), 2.41–2.31 (m, 2H), 2.12 (t, J=23.8 Hz, 2H), 1.97–1.81 (m, 4H), 1.69–1.59 (m, 2H).

EXAMPLE 135

4-Chloro-1,1-dioxido-2-(4-(4-(2-oxo-3-benzoxazolinyl)-piperidin-1-yl)-butyl)-1,2-benzisothiazol-3(2H)-one mp 178°–180 ° C. $^1$H NMR (400 MHz, CDCl$_3$) 7.88–7.84 (m, 1H), 7.82–7.76 (m, 2H), 7.31–7.26 (m, 1H), 7.24–7.08 (m, 3H), 4.21 (m, 1H), 3.84 (t, J=14.6 Hz, 2H), 3.09 (d, J=9.6 Hz, 2H), 2.46 ( t, J=14.5 Hz, 2H), 2.43–2.33 (m, 2H), 2.12 (t, J=23.8 Hz, 2H), 1.99–1.83 (m, 4H), 1.71–1.59 (m, 2H).

EXAMPLE 136

4-Ethoxy-1,1-dioxido-2-(4-(4-(2-oxo-3-benzoxazolinyl)-piperidin-1-yl)-butyl)-1,2-benzisothiazol-3(2H)-one $^1$H NMR (400 MHz, CDCl$_3$), 7.77 (t, J=7.6 Hz, 1H), 7.45 (d, J=8.0 30 Hz, 1H), 7.28–7.27 (m, 2H), 7.19 (d, J=7.6 Hz, 1H), 7.15 (t, J=7.6 Hz, 1H), 7.08 (td, J=7.6, 1.4 Hz, 1H), 4.28 (q, J=7.0 Hz, 2H), 4.26 (tt, J=12.6, 4.2 Hz, 1H), 3.78 (t, J=7.4 Hz, 2H), 3.07 (d, J=11.6 Hz, 2H), 2.44 (t, J=7.2 Hz, 2H), 2.36 (td, J=12.5, 3.7 Hz, 2H), 2.11 (td, J=12.0, 1.6 Hz, 2H), 1.93–1.83 (m, 4H), 1.63 (qn, J=7.6 Hz, 2H), 1.55 (t, J=7.0 Hz, 3H).

EXAMPLE 137

4-(2-Propyloxy)-1,1-dioxido-2-(4-(4-(2-oxo-3-benzoxazolinyl)-piperidin-1-yl)-butyl)-1,2-benzisothiazol-3(2H)-one $^1$H NMR (400 MHz, CDCl$_3$) 7.75 (dd, J=8.4, 7.7 Hz, 1H), 7.43 (d, J=7.5 Hz, 1H), 7.27 (d, J=7.9 Hz, 1H), 7.26 (d, J=8.6

Hz, 1H), 7.19 (dd, J=7.8, 1.2 Hz, 1H), 7.14 (td, J=7.7, 1.3 Hz, 1H), 7.08 (td, J=7.8, 1.2 Hz, 1H), 4.77 (sept., J=6.0 Hz, 1H), 4.21 (tt, J=12.5, 4.3 Hz, 1H), 3.77 (t, J=7.4 Hz, 2H), 3.07 (d, J=11.7 Hz, 2H), 2.44 (t, J=7.3 Hz, 2H), 2.36 (td, J=12.6, 3.8 Hz, 2H), 2.11 (td, J=11.9, 1.8 Hz, 2H), 1.94–1.83 (m, 4H), 1.63 (qn, J=7.5 Hz, 2H), 1.47 (d, J=6.0 Hz, 6H).

EXAMPLE 138

5-Methoxy-1,1-dioxido-2-(4-(4-(6-methyl-2-oxo-3-benzoxazolinyl)-piperidin-1-yl)-butyl)-1,2-benzisothiazol-3(2H)-one $^1$H NMR (400 MHz, CDCl$_3$) 7.81 (d, J=8.6 Hz, 1H), 7.77 (d, J=8.1 Hz, 1H), 7.48 (d, J=2.2 Hz, 1H), 7.33 (dd, J=8.6, 2.4 Hz, 1H), 7.07 (d, J=7.9 Hz, 1H), 7.03 (s, 1H), 4.56 (t, J=12.6 Hz, 1H), 3.97 (s, 3H), 3.83 (t, J=6.6 Hz, 2H), 3.72 (d, J=11.0 Hz, 2H), 3.25 (m, 2H), 3.11 (m, 2H), 2.90 (m, 2H), 2.37 (s, 3H), 2.09–1.96 (m, 6H).

EXAMPLE 139

1,1-Dioxido-2-(4-(4-(2-oxo-3-benzoxazolinyl)-piperidin-1-yl)-butyl)-6-methylsulfonyl-1,2-benzisothiazol-3(2H)-one $^1$H NMR (400 MHz, CDCl$_3$) 8.51 (s, 1H), 8.40 (d, J=9.57 Hz, 1H), 8.27 (d, J=7.89 Hz, 1H), 7.20 (d, J=7.73 Hz, 1H), 7.16–7.08 (m, 3H), 4.21 (m, 1H), 3.89 (t, J=7.39 Hz, 2H), 3.17 (s, 3H), 3.12 (bd, 2H), 2.40 (s, 2H), 2.37 (d, 2H), 1.93 (t, J=7.73 Hz, 2H), 1.87 (bd, 2H), 1.60 (bm, 4H).

EXAMPLE 140

5-Methoxy-1,1-dioxido-2-(4-(4-(2-oxo-3-benzoxazolinyl)-piperidin-1-yl)-butyl)-1,2-benzisothiazol-3(2H)-one $^1$H NMR (400 MHz, CDCl$_3$) 7.93 (d, J=7.87 Hz, 1H), 7.82 (d, J=8.60 Hz, 1H), 7.48 (d, J=2.38 Hz, 1H), 7.34 (dd, J=6.22, 2.38 Hz, 1H), 7.27 (m, 1H), 7.20 (d, J=7.14 Hz, 1H), 7.13 (t, J=7.69 Hz, 1H), 4.60 (tt, J=12.81, 4.03 Hz, 1H), 3.97 (s, 3H), 3.83 (t, J=6.59 Hz, 2H), 3.74 (d, J=12.09 Hz, 2H), 3.32 (dq, J=12.82, 4.03 Hz, 2H), 3.12 (br t, J=4.58 Hz, 2H), 2.92 (br q, J=10.07 Hz, 2H), 2.14–1.95 (m, 6H).

EXAMPLE 141

1,1-Dioxido-2-(4-(4-(2-oxo-3-benzoxazolinyl)-piperidin-1-yl)-butyl)-5-methylsulfonyl-1,2-benzisothiazol-3(2H)-one $^1$H NMR (400 MHz, DMSO-d$_6$) 8.67 (d, J=8.06 Hz, 1H), 8.57 (dd, J=8.06, 1.51 Hz, 1H), 8.54 (s, 1H), 7.39 (m, 2H), 7.26 (t, J=7.88 Hz, 1H), 7.17 (t, J=7.72 Hz, 1H), 4.49 (dt, J=11.92, 4.01 Hz, 1H), 3.85 (bm, 2H), 3.64 (br d, J=11.92 Hz, 2H), 3.44 (s, 3H), 3.20–3.10 (m, 2H), 2.54 (m, 2H), 2.08 (br d, J=12.59 Hz, 2H).

EXAMPLE 142

5-Methylthio-1,1-dioxido-2-(4-(4-(2-oxo-3-benzoxazolinyl)-piperidin-1-yl)-butyl)-1,2-benzisothiazol-3(2H)-one $^1$H NMR (400 MHz, CDCl3) 7.93 (d, J=7.87 Hz, 1H), 7.77 (m, 2H), 7.63 (dd, J=8.24, 1.83 Hz, 1H), 7.27 (m, 1H), 7.20 (dd, J=8.05, 1.10 Hz, 1H), 7.13 (t, J=8.42, 0.92 Hz, 1H), 4.60 (dt, J=12.81, 4.22 Hz, 1H), 3.84 (t, J=6.59 Hz, 2H), 3.74 (br d, J=11.54 Hz, 2H), 3.33 (dq, J=13.55, 3.84 Hz, 2H), 3.13 (m, 2H), 2.93 (q, J=10.07 Hz, 2H), 2.60 (s, 3H), 2.14–1.93 (m, 6H).

EXAMPLE 143

5-Methylsulfonyl-1,1-dioxido-2-(4-(4-(6-methyl-2-oxo-3-benzoxazolinyl)-piperidin-1-yl)-butyl)-1,2-benzisothiazol-3(2H)-one $^1$H NMR (400 MHz, CDCl$_3$) 8.63 (s, 1H), 8.46 (dd, J=8.05, 1.65 Hz, 1H), 8.15 (dd, J=8.05, 0.55 Hz, 1H), 7.13 (d, J=8.06 Hz, 1H), 7.03 (s, 1H), 6.95 (d, J=8.05 Hz, 1H), 4.18 (dt, J=12.01, 4.21 Hz, 1H), 3.89 (t, J=7.33 Hz, 2H), 3.16 (s, 3H), 3.07 (br d, J=10.99 Hz, 2H), 2.46 (t, J=7.14 Hz, 2H), 2.38 (s, 3H), 2.34 (m, 2H), 2.11 (t, J=11.17 Hz, 2H), 1.97–1.84 (m, 6H).

EXAMPLE 144

1,1-Dioxido-2-(4-(4-(2-oxo-1-oxazolo[5,4-b]pyridyl)-piperidin-1-yl)-butyl)-1,2-benzisothiazol-3(2H)-one $^1$H NMR (400 MHz, CDCl$_3$) 8.38 (d, J=7.51 Hz, 1H), 8.07 (m, 2H), 7.91 (m, 3H), 7.25 (m, 1H), 4.64 (m, 1H), 3.86 (t, J=3.20 Hz, 2H), 3.74 (br d, J=10.99 Hz, 2H), 3.29 (m, 2H), 3.13 (bs, 2H), 2.92 (m, 2H), 2.18–1.99 (m, 6H).

---

What is claimed is:

1. A compound of the formula

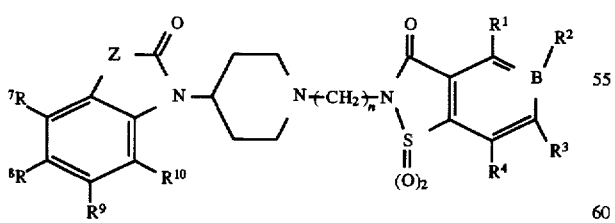

and a pharmaceutically acceptable salt, prodrug, polymorph, or metabolite thereof wherein:

n is an integer from 3 to 5;

B is carbon or nitrogen;

$R^1$, $R^2$, $R^3$ and $R^4$ are each independently selected from the group consisting of hydrogen; halogen; nitro; amino; substituted or unsubstituted lower alkyl; perhalogenated lower alkyl; substituted or unsubstituted lower alkoxy; sulfonyl alkyl; and substituted or unsubstituted aryl or heteroaryl, with the proviso that if B is a nitrogen, then the substituent $R^2$ group is not present;

$R^7$, $R^8$, $R^9$ and $R^{10}$ are each independently selected from the group consisting of hydrogen, lower alkyl, lower alkenyl, and lower alkoxy; and Z is O, S, $CH_2$, NH, or NMe.

2. The compound of claim 1, of the formula

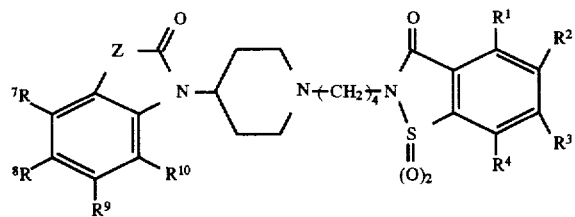

and a pharmaceutically acceptable salt, prodrug, polymorph, or metabolite thereof.

3. The compound of claim 2, of the formula

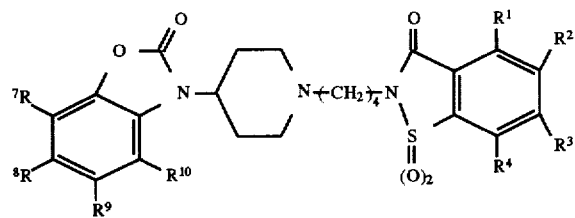

and a pharmaceutically acceptable salt, prodrug, polymorph, or metabolite thereof.

4. The compound of claim 1, selected from:

1,1-Dioxido-2-(4-(4-(2-oxo-3-benzoxazolinyl)-piperidin-1-yl)-butyl)-1,2-benzisothiazol-3(2H)-one;

1,1-Dioxido-2-(4-(4-(2-oxo-3,1,4-benzoxazinyl)-piperidin-1-yl)-butyl)-1,2-benzisothiazol-3(2H)-one;

1,1-Dioxido-2-(4-(4-(2-oxo-3-benzoxazolinyl)-piperidin-1-yl)-butyl)-5-nitro-1,2-benzisothiazol-3(2H)-one;

6-Chloro-1,1-dioxido-2-(4-(4-(2-oxo-3-benzoxazolinyl)-piperidin-1-yl)-butyl)-1,2-benzisothiazol-3(2H)-one;

5-Chloro-1,1-dioxido-2-(4-(4-(2-oxo-3-benzoxazolinyl)-piperidin-1-yl)-butyl)-1,2-benzisothiazol-3(2H)-one;

1,1-Dioxido-2-(4-(4-(2-oxo-3-benzoxazolinyl)-piperidin-1-yl)-butyl)-7-nitro-1,2-benzisothiazol-3(2H)-one;

1,1-Dioxido-2-(4-(4-(2-oxo-3-benzoxazolinyl)-piperidin-1-yl)-butyl)-4-methoxy-1,2-benzisothiazol-3(2H)-one;

1,1-Dioxido-2-(4-(4-(5-chloro-2-oxo-3-benzoxazolinyl)-piperidin-1-yl)-butyl)-1,2-benzisothiazol-3(2H)-one;

1,1-Dioxido-2-(4-(4-(3a-(R)-8a-(S)-2-oxo-3,3a,8,8a-tetrahydro-2H-indeno[1,2-d]oxazolinyl)-piperidin-1-yl)-butyl)-1,2-benzisothiazol-3(2H)-one;

1,1-Dioxido-2-(4-(4-(2-oxonaphth[2,3-d]oxazolinyl)-piperidin-1-yl)-butyl)-1,2-benzisothiazol-3(2H)-one;

1,1-Dioxido-2-(4-(4-(6-methyl-2-oxo-3-benzoxazolinyl)-piperidin-1-yl)-butyl)-1,2-benzisothiazol-3(2H)-one;

1,1-Dioxido-2-(4-(4-(2-oxo-5-phenyl-3-benzoxazolinyl)-piperidin-1-yl)-butyl)-1,2-benzisothiazol-3(2H)-one;

1,1-Dioxido-2-(4-(4-(6-methoxy-2-oxo-3-benzoxazolinyl)-piperidin-1-yl)-butyl)-1,2-benzisothiazol-3(2H)-one;

1,1-Dioxido-2-(4-(4-(6-carbomethoxy-2-oxo-3-benzoxazolinyl)-piperidin-1-yl)-butyl)-1,2-benzisothiazol-3(2H)-one;

1,1-Dioxido-2-(4-(4-(5-ethylsulfonyl-2-oxo-3-benzoxazolinyl)-piperidin-1-yl)-butyl)-1,2-benzisothiazol-3(2H)-one;

1,1-Dioxido-2-(4-(4-(2-oxo-3-oxazolo[4,5-b]pyridyl)-piperidin-1-yl)-butyl)-1,2-benzisothiazol-3(2H)-one;

1,1-Dioxido-2-(4-(4-(7-carbethoxy-2-oxo-3-benzoxazolinyl)-piperidin-1-yl)-butyl)-1,2-benzisothiazol-3(2H)-one;

1,1-Dioxido-2-(4-(4-(5-tert-butyl-2-oxo-3-benzoxazolinyl)-piperidin-1-yl)-butyl)-1,2-benzisothiazol-3(2H)-one;

1,1-Dioxido-2-(4-(4-(5,7-dimethyl-2-oxo-3-benzoxazolinyl)-piperidin-1-yl)-butyl)-1,2-benzisothiazol-3(2H)-one;

1,1-Dioxido-2-(4-(spiro(1,3-dihydro-1-oxo-2H-indene-2,4'-piperidin-1'-yl)butyl)-1,2-benzisothiazol-3(2H)-one; or 1,1-Dioxido-2-(4-(4-(6-methyl-2-oxo-3-benzoxazolinyl)-piperidin-1-yl)-butyl)-5-nitro-1,2-benzisothiazol-3(2H)-one;

and a pharmaceutically acceptable salt, prodrug, polymorph, or metabolite thereof.

5. The compound of claim 4 selected from:

5-Chloro-1,1-dioxido-2-(4-(4-(2-oxo-3-benzoxazolinyl)-piperidin-1-yl)-butyl)-1,2-benzisothiazol-3(2H)-one; or 1,1-Dioxido-2-(4-(4-(6-methyl-2-oxo-3-benzoxazolinyl)-piperidin-1-yl)-butyl)-5-nitro-1,2-benzisothiazol-3(2H)-one;

and a pharmaceutically acceptable salt, prodrug, polymorph, or metabolite thereof.

6. A pharmaceutical composition comprising the compound of claim 1 and a pharmaceutically acceptable carrier.

7. A method of treating benign prostatic hyperplasia in a subject in need thereof which comprises administering to the subject a therapeutically effective amount of the compound of claim 1.

8. The method of claim 7, wherein the compound additionally does not cause a fall in blood pressure at dosages effective for treating benign prostatic hyperplasia.

9. A method of treating benign prostatic hyperplasia in a subject in need thereof which comprises administering to the subject a therapeutically effective amount of the composition of claim 6.

10. A method of inhibiting contraction of prosate tissue in a subject in need thereof which comprises administering to the subject a therapeutically effective amount of the compound of claim 1.

11. The method of claim 10, wherein the compound additionally does not cause a fall in blood pressure at dosages effective for inhibiting contraction of prostate tissue.

12. A method of inhibiting contraction of prosate tissue in a subject in need thereof which comprises administering to the subject a therapeutically effective amount of the composition of claim 6.

13. A method of using the compound of claim 1 to selectively antagonize the human alpha 1C adrenergic receptor which comprises exposing the human alpha 1C adrenergic receptor to an antagonistically effective amount of said compound.

* * * * *